(12) United States Patent
Liao et al.

(10) Patent No.: US 10,688,193 B2
(45) Date of Patent: Jun. 23, 2020

(54) PH-SENSITIVE LINKERS FOR DELIVERING A THERAPEUTIC AGENT

(71) Applicant: GNT BIOTECH & MEDICALS CORPORATION, Taipei (TW)

(72) Inventors: Yu-Jung Liao, Taipei (TW); Wei-Jan Huang, Taipei (TW); Chia-Nan Chen, Taipei (TW); Huan-Yu Lin, Taipei (TW); Ching-Yi Lin, Taipei (TW); Meng-Ju Tsai, Taipei (TW); Wan-Yi Hsu, Taipei (TW); Li-Ling Chi, Taipei (TW); Ye-Su Chao, Taipei (TW); Yi-Hong Wu, Taipei (TW)

(73) Assignee: GNT BIOTECH & MEDICALS CORPORATION, Taipei (TW)

( * ) Notice: Subject to any disclaimer, the term of this patent is extended or adjusted under 35 U.S.C. 154(b) by 0 days.

(21) Appl. No.: 15/746,544

(22) PCT Filed: Jul. 21, 2016

(86) PCT No.: PCT/CN2016/090893
§ 371 (c)(1),
(2) Date: Jan. 22, 2018

(87) PCT Pub. No.: WO2017/012568
PCT Pub. Date: Jan. 26, 2017

(65) Prior Publication Data
US 2018/0221498 A1  Aug. 9, 2018

Related U.S. Application Data

(60) Provisional application No. 62/195,654, filed on Jul. 22, 2015.

(51) Int. Cl.
| | | |
|---|---|---|
| A61K 47/64 | (2017.01) | |
| A61K 47/60 | (2017.01) | |
| A61K 47/69 | (2017.01) | |
| C07C 243/26 | (2006.01) | |
| C07C 271/22 | (2006.01) | |
| C07C 323/60 | (2006.01) | |
| C07K 5/062 | (2006.01) | |
| A61K 9/14 | (2006.01) | |
| C07C 323/52 | (2006.01) | |
| C07D 339/04 | (2006.01) | |
| C07K 5/103 | (2006.01) | |
| A61P 35/00 | (2006.01) | |
| A61K 47/20 | (2006.01) | |
| A61K 31/351 | (2006.01) | |
| A61K 31/437 | (2006.01) | |
| A61K 33/24 | (2019.01) | |
| A61K 47/22 | (2006.01) | |

(52) U.S. Cl.
CPC .............. *A61K 47/64* (2017.08); *A61K 9/143* (2013.01); *A61K 47/20* (2013.01); *A61K 47/60* (2017.08); *A61K 47/6923* (2017.08); *A61K 47/6929* (2017.08); *A61P 35/00* (2018.01); *C07C 243/26* (2013.01); *C07C 271/22* (2013.01); *C07C 323/52* (2013.01); *C07C 323/60* (2013.01); *C07D 339/04* (2013.01); *C07K 5/06026* (2013.01); *C07K 5/1008* (2013.01); *A61K 31/351* (2013.01); *A61K 31/437* (2013.01); *A61K 33/24* (2013.01); *A61K 47/22* (2013.01); *A61K 2300/00* (2013.01)

(58) Field of Classification Search
CPC ................................................. A61K 47/6929
See application file for complete search history.

(56) References Cited

U.S. PATENT DOCUMENTS

2013/0138032 A1  5/2013  Kim et al.
2013/0331764 A9  12/2013  Kim

FOREIGN PATENT DOCUMENTS

WO  WO 2013/139942        9/2013
WO  WO 2017/012568 A1   1/2017

OTHER PUBLICATIONS

Kawano et al. J. Drug. Deliv. 2011, 1-6.*
Hyun Jin Lee & Younsoo Bae, "Brushed Block Copolymer Micelles with pH-Sensitive Pendant Groups for Controlled Drug Delivery," Pharm Res., vol. 30, No. 8, Aug. 31, 2013 (Aug. 31, 2013), ISSN: 1573-904X, pp. 2077-2086.
Feng Wang et al., "Doxorubicin-Tethered Responsive Gold Nanoparticles Facilitate Intracellular Drug Delivery for Overcoming Multidrug Resistance in Cancer Cells," ACS Nano, vol. 5, No. 5, May 24, 2011 (May 24, 2011), ISSN: 1936-0851, pp. 3679-3692.
Steven M. Ansell et al., "3-(2-Pyridyldithio)propionic Acid Hydrazide as a Cross-Linker in the Formation of Liposome-Antibody Conjugates," Bioconjugate Chem., vol. 7, No. 4, Jul. 25, 1996 (Jul. 25, 1996), ISSN: 1043-1802, pp. 490-496.
Tian-Meng Sun et al., "Cancer stem cell therapy using doxorubicin conjugated to gold nanoparticles via hydrazone bonds," Biomaterials, vol. 35, No. 2, Oct. 18, 2013 (Oct. 18, 2013), ISSN: 1878-5905, pp. 836-845.
Extended European Search Report dated Dec. 21, 2018, from corresponding European Patent Application No. 16827259.9, 7 pages.
Hyejin Park et al.; "Cell-selective intracellular drug delivery using doxorubicin and a-helical peptides conjugated to gold nanoparticles"; Biomaterials 35 (2014) 3480-3487.

(Continued)

*Primary Examiner* — Ana Z Muresan
(74) *Attorney, Agent, or Firm* — Duane Morris

(57) ABSTRACT

The invention provides a pH-sensitive linker that can simultaneously bind metallic nanoparticles and one or more agents with various molecular size. The linker of the invention can deliver the agents into cells involved in disease processes or close to cells so that the agents can selectively target and effect on the cells. The target delivery provided by the linker of the invention can be used for example for disease sensing, imaging, drug delivery, and therapy.

32 Claims, 8 Drawing Sheets

(56) References Cited

OTHER PUBLICATIONS

Tian-Meng Sun et al., "Cancer stem cell therapy using doxorubicin conjugated to gold nanoparticles via hydrazone bonds", Biomaterials, 2014, vol. 35, No. 2, pp. 836-845.
Feng Wang et al., "Doxorubicin-Tethered Responsive Gold Nanoparticles Facilitate Intracellular Drug Delivery for Overcoming Multidrug Resistance in Cancer Cells", ACS Nano, 2011, vol. 5, No. 5, pp. 3679-3692.

* cited by examiner (A)

(B)

(A)

(B)

(C)

PH-SENSITIVE LINKERS FOR DELIVERING A THERAPEUTIC AGENT

FIELD OF THE INVENTION

The invention relates to a linker that can link with an agent and a nanoparticle. Particularly, the linker of the invention is pH-sensitive and can binds to nanoparticles and same or different species of agents simultaneously.

BACKGROUND OF THE INVENTION

Specific, efficient delivery of therapeutic and diagnostic compounds to cells, especially to the cytosol, is a major goal of many pharmaceutical companies. A number of different approaches have been utilized to increase specificity and uptake. For example, nanotechnology has been widely used in the development of new strategies for drug delivery and cancer therapy. PH-sensitive nano-systems have been developed in which drug release is specifically triggered by the acidic tumor environment and such systems can improve the efficiency of cancer treatment. Feng Wnang et al. develop a drug delivery system by tethering doxorubicin onto the surface of AuNPs with a poly(ethylene glycol) space via an acid-labile linkage (*American Chemical Society,* 2011, Vol. 5, No. 5, pp. 3679-3692). Tian-Meng Sun et al., discloses a cancer stem cell therapy using doxorubicin conjugated to gold nanoparticles via hydrazone bonds (*Biomaterials* 35, 2014, pp. 836-845). US 2013/0331764 relates to a method for delivering an anticancer drug into cancer cells by binding the anticancer drug to pH-sensitive metal nanoparticles so as to be separated from cancer cells. WO 2013/139942 provides a nanoparticle comprising a metal nanoparticle and at least one linker.

However, there is still a need to develop a pH-sensitive delivery system having better efficacy.

SUMMARY OF THE INVENTION

The provides a pH-sensitive linker having the following Formula (I),

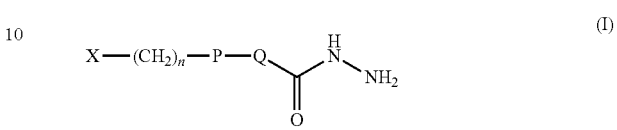

wherein
X is

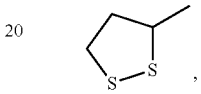

—SH, —NH$_2$ (Boc-NH—; Fmoc-NH—), —COOH;
n is 1 to 6;
P is —C(O)NH— or —C(O)O—;
Q is —R(CH$_2$CH$_2$O)m-, R(—C(O)NH-)z or —R[—C(O)CH$_2$CH$_2$—C(O)NH—(CH$_2$CH$_2$O)m]Y;
R is a bond, —C$_{1-12}$alkyl or C$_{1-10}$alkoxy;
m is 1 to 12;
z is 1 to 4; and
Y is 1 to 12.

In some embodiments, the linker has the following formula:

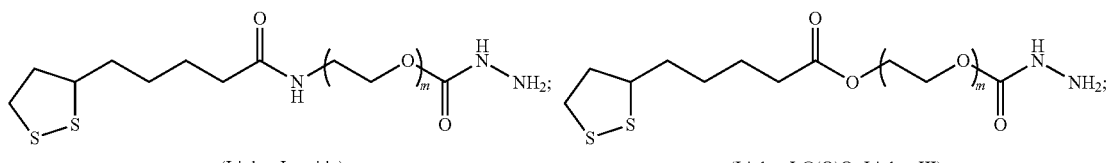

(Linker I-amide)     (Linker I-C(O)O; Linker III)

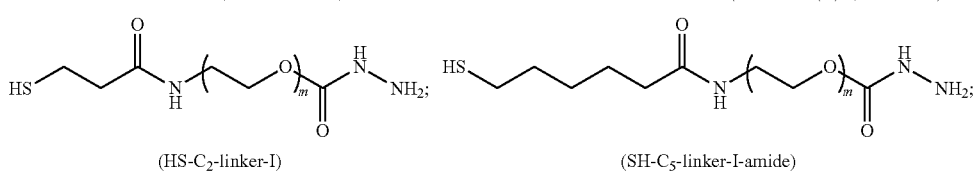

(HS-C$_2$-linker-I)     (SH-C$_5$-linker-I-amide)

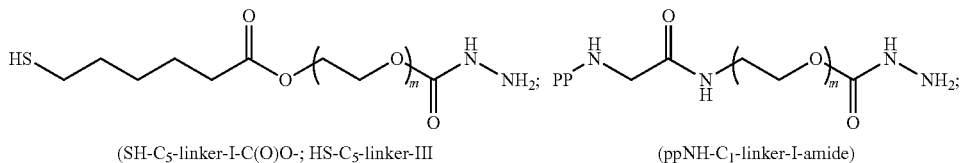

(SH-C$_5$-linker-I-C(O)O-; HS-C$_5$-linker-III)     (ppNH-C$_1$-linker-I-amide)

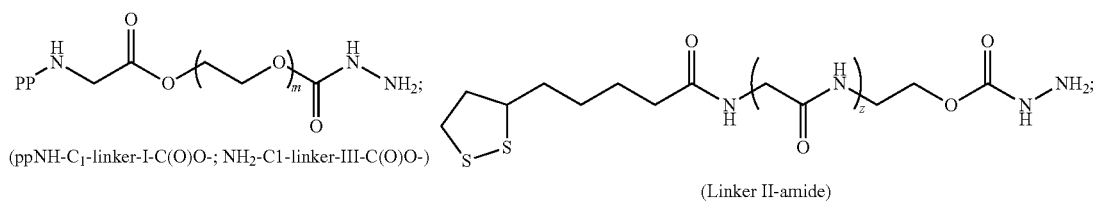

(ppNH-C$_1$-linker-I-C(O)O-; NH$_2$-C1-linker-III-C(O)O-)     (Linker II-amide)

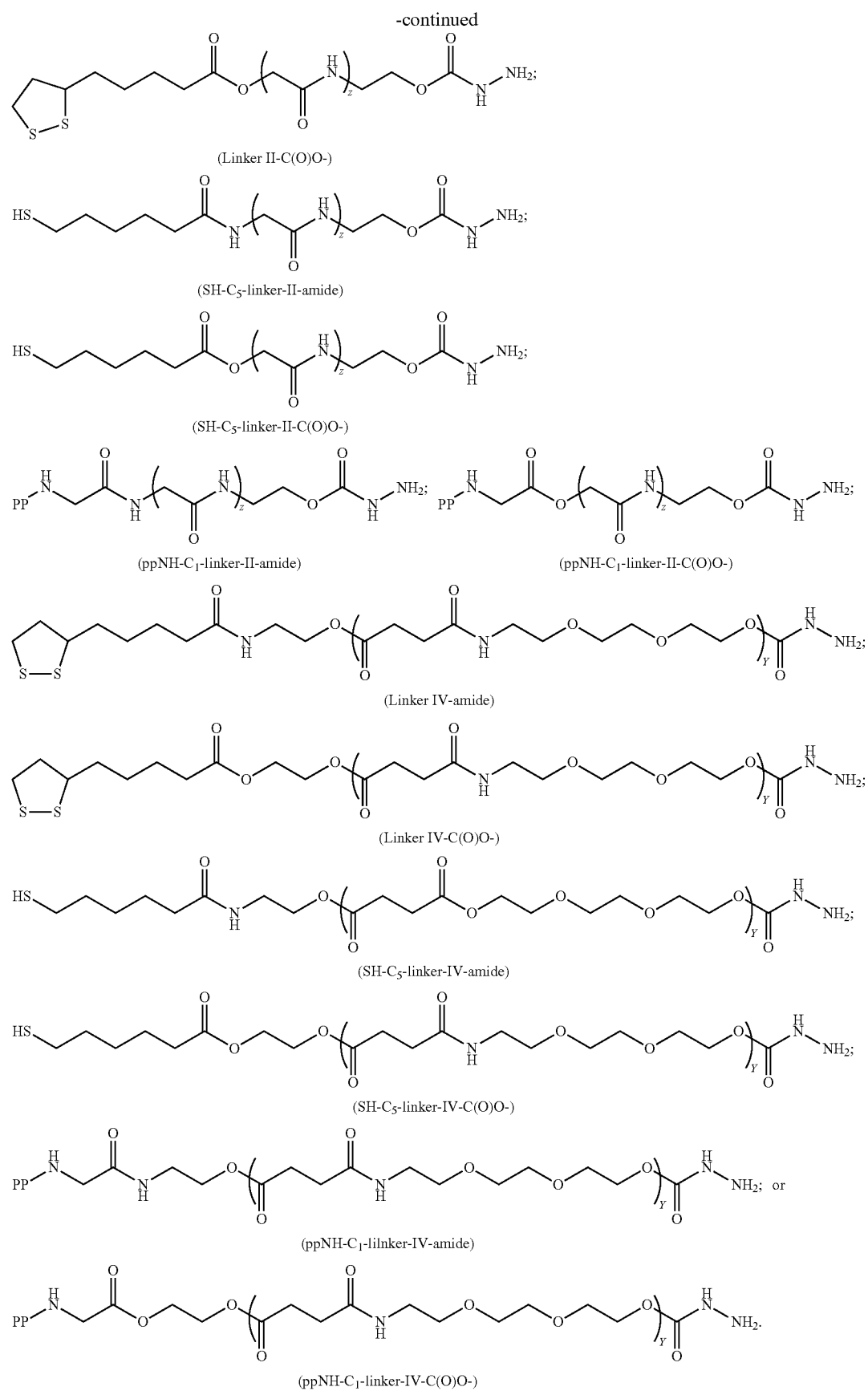

The invention also provides a metallic nanoparticle complex, comprising a metallic nanoparticle complexed with one or more linkers of the invention, optionally complexed with one or more PEGs. In one embodiment, the metallic nanoparticle is Au, Pd, Pt or Ag nanoparticle. In one embodiment, the linker is same or different. More preferably, the metallic nanoparticle complex comprises plural linkers with different molecular length.

The invention also provides a composition comprising one or more metallic nanoparticle complex linking one or more same of different therapeutic or diagnostic agents and a pharmaceutically acceptable carrier.

The invention also provides a drug delivery system, comprising one or more metallic nanoparticle complex linking one or more same of different therapeutic or diagnostic agents.

DETAILED DESCRIPTION OF THE INVENTION

Figure 1A:
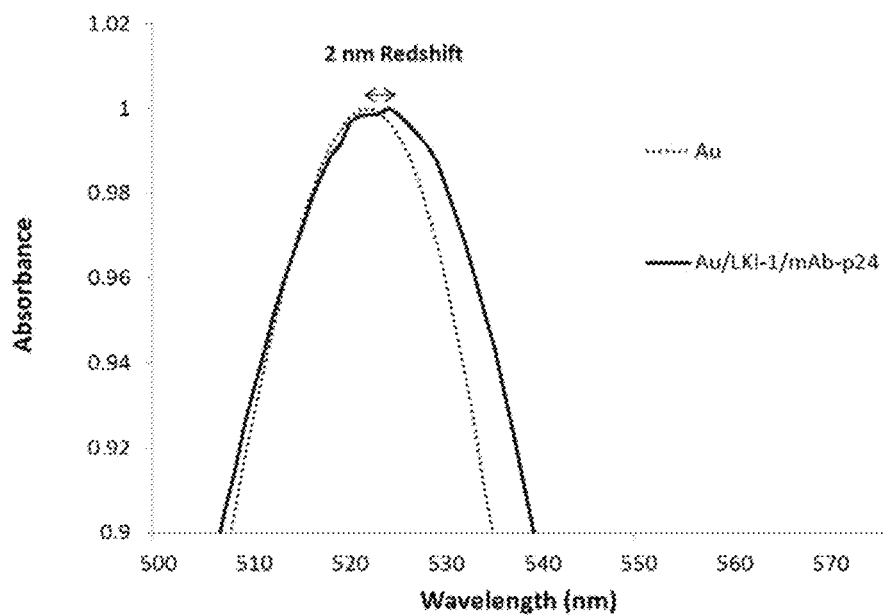
FIGS. 1 (A) to (C) show anti-HIV-1 p24 antibody (mAb3) conjugated onto gold nanoparticles (Au/LKI-1/mAb-p24) still showed the binding affinity. (A) The absorption spectrum of Au/LKI-1/mAb-p24 complex and Au. The Au/LKI-1/mAb-p24 complex shows a 2 nm red shift in the plasmon peak. (B) The Au/LKI-1/mAb-p24 complexes showed fluorescence by detected with Alexa Fluor 568 secondary antibodies. (C) The ELISA assay was used to demonstrate the formation of Au/LKI-1/mAb-p24 complex, and the binding activity of p24 antigen to compare with that of mAb-p24.

The invention is based on at least a discovery of a pH-sensitive linker that can simultaneously bind metallic nanoparticles and one or more agents with various molecular sizes. The linker of the invention can deliver the agents into cells involved in disease processes or close to cells so that the agents can selectively target and effect on the cells. The target delivery provided by the linker of the invention can be used for example for disease sensing, imaging, drug delivery, and therapy.

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are pluralities of definitions for a term herein, those in this section prevail unless stated otherwise.

The term "antibody" is used in the broadest sense and includes monoclonal antibodies (e.g., full length or intact monoclonal antibodies), polyclonal antibodies, monovalent, multivalent antibodies, multispecific antibodies (e.g., bispecific antibodies so long as they exhibit the desired biological activity) and may also include certain antibody fragments (as described in greater detail herein). An antibody can be chimeric, human, humanized and/or affinity matured.

The term "tumor," as used herein, refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein.

The term "cancer," as used herein, refers to the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia, squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

As used herein, the terms "treating," "treatment," "therapeutic," or "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the patient's overall feeling of well-being or appearance.

An "effective amount" refers to an amount effective, at dosages and for periods of time necessary, to achieve the desired therapeutic or prophylactic result.

A "therapeutically effective amount" of a substance/molecule of the invention may vary according to factors such as the disease state, age, sex, and weight of the individual, and the ability of the substance/molecule, to elicit a desired response in the individual. A therapeutically effective amount is also one in which any toxic or detrimental effects of the substance/molecule are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount would be less than the therapeutically effective amount.

The term "pharmaceutically acceptable salt" refers to a salt of a compound that does not cause significant irritation to an organism to which it is administered and does not abrogate the biological activity and properties of the compound.

In one aspect, the invention provides a pH-sensitive linker having the following Formula (I),

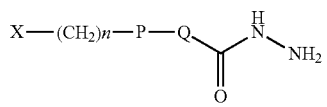
(I)

wherein
X is

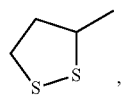,

—SH, —NH$_2$ (Boc-NH—; Fmoc-NH—), —COOH;
n is 1 to 6;
P is —C(O)NH— or —C(O)O—;
Q is —R(CH$_2$CH$_2$O)m-, R(—C(O)NH-)z or —R[—C(O)CH$_2$CH$_2$—C(O)NH—(CH$_2$CH$_2$O)m]Y;
R is a bond, —C$_{1-12}$alkyl or C$_{1-10}$alkoxy;
m is 1 to 12;
z is 1 to 4; and
Y is 1 to 12.

In some embodiments, the linker of the invention has the following formula:

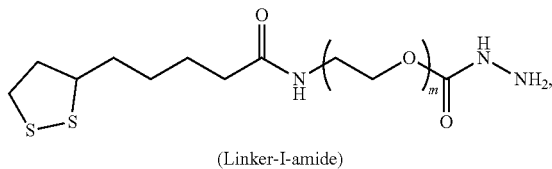

(Linker-I-amide)

wherein m is 1 to 12.

Linker I-amide has formula (I) wherein X is

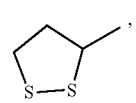, n is 4, P is C(O)NH, R is a bond and Q is —R(CH$_2$CH$_2$O)$_m$—. Preferably, m is an integer of 1 to 6. More preferably, m is an integer of 2.

The linkers of Linker I-amide of the present invention can be prepared using methods known to those skilled in the art in view of this disclosure. For example, the preferred linkers of the invention can be prepared as shown in the following scheme.

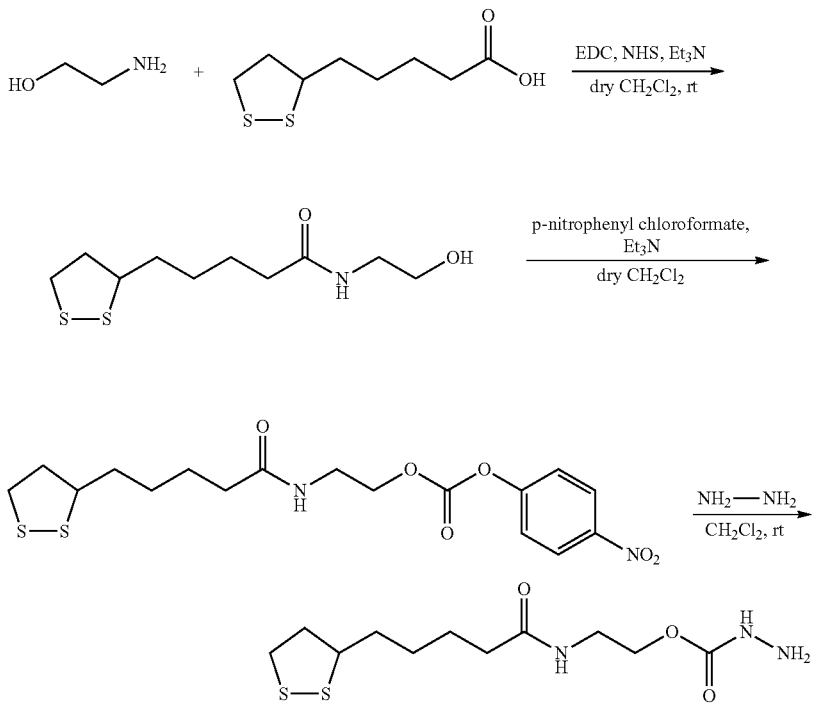

In some embodiments, the linker of the invention has the following formula:

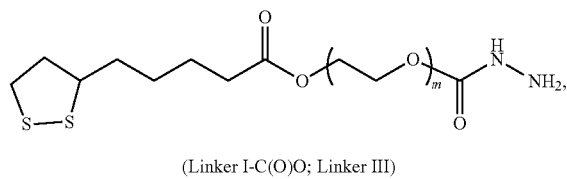

(Linker I-C(O)O; Linker III)

wherein m is 1 to 12.

Linker I-C(O)O (Linker III) has formula (I) wherein X is

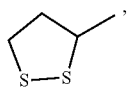

n is 4, P is —C(O)O—, R is a bond, Q is —R(CH$_2$CH$_2$O)$_m$—, and m is 1 to 12. More preferably, m is an integer of 2.

The linkers of Linker I-C(O)O (Linker III) of the present invention can be prepared using methods known to those skilled in the art in view of this disclosure. For example, the preferred linkers of the invention can be prepared as shown in the following scheme.

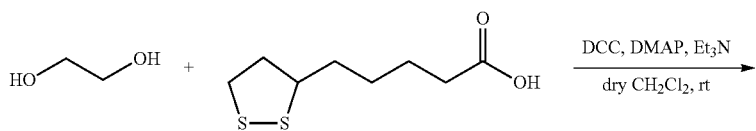

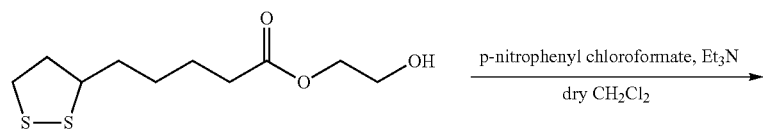

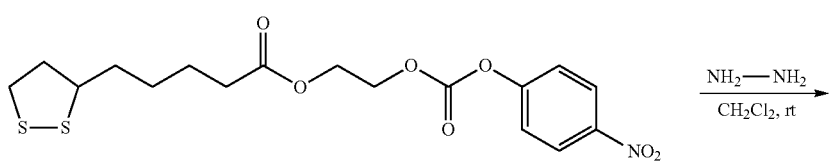

In some embodiments, the linker of the invention has the following formula:

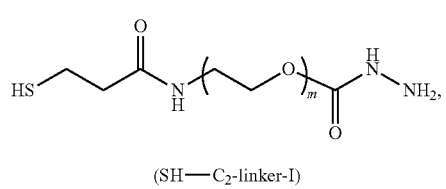

(SH—C$_2$-linker-I)

wherein m is 1 to 12.

Linker SH—C$_2$-linker-I has formula (I) wherein X is —SH, n is 2, P is —C(O)NH—, R is a bond, Q is —R(CH$_2$CH$_2$O)m-, and m is 1 to 12. More preferably, m is an integer of 2.

The linkers of SH—C$_2$-linker-I of the present invention can be prepared using methods known to those skilled in the art in view of this disclosure. For example, the preferred linkers of the invention can be prepared as shown in the following scheme.

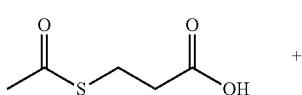

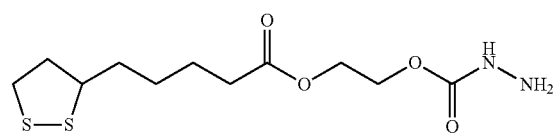

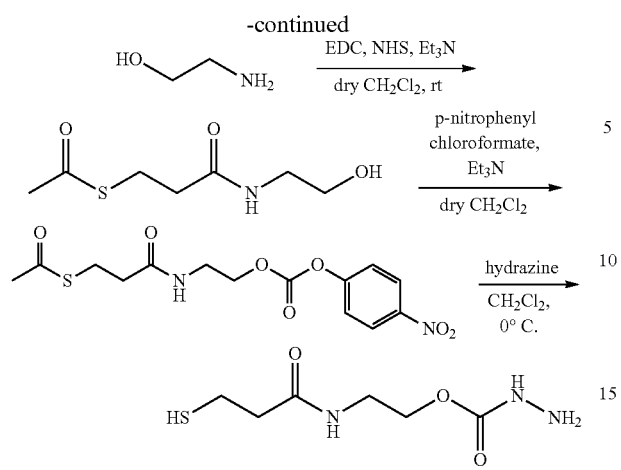

In some embodiments, the linker of the invention has the following formula:

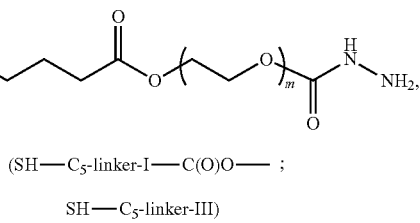

(SH—C$_5$-linker-I—C(O)O— ;
SH—C$_5$-linker-III)

wherein m is 1 to 12.

In some embodiments, the linker of the invention has the following formula:

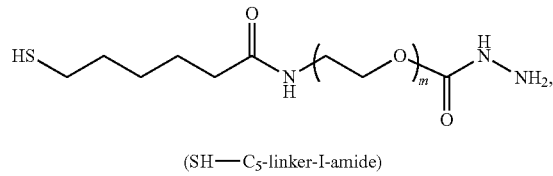

(SH—C$_5$-linker-I-amide)

wherein m is 1 to 12.

Linker SH—C$_5$-linker-I-amide has formula (I) wherein X is —SH, n is 5, P is —C(O)NH—, R is a bond, Q is —R(CH$_2$CH$_2$O)$_m$—, and m is 1 to 12. More preferably, m is an integer of 2.

The linkers of SH—C$_5$-linker-I-amide of the present invention can be prepared using methods known to those skilled in the art in view of this disclosure. For example, the preferred linkers of the invention can be prepared as shown in the following scheme.

SH—C$_5$-linker-I-C(O)O— (SH—C$_5$-linker-III) has formula (I) wherein X is —SH, n is 5, P is —C(O)O—, R is a bond, Q is —R(CH$_2$CH$_2$O)$_m$—, and m is 1 to 12. Preferably, m is an integer of 1 to 6. More preferably, m is an integer of 2.

The linkers of SH—C$_5$-linker-I-C(O)O— (SH—C$_5$-linker-III) of the present invention can be prepared using methods known to those skilled in the art in view of this disclosure. For example, the preferred linkers of the invention can be prepared as shown in the following scheme.

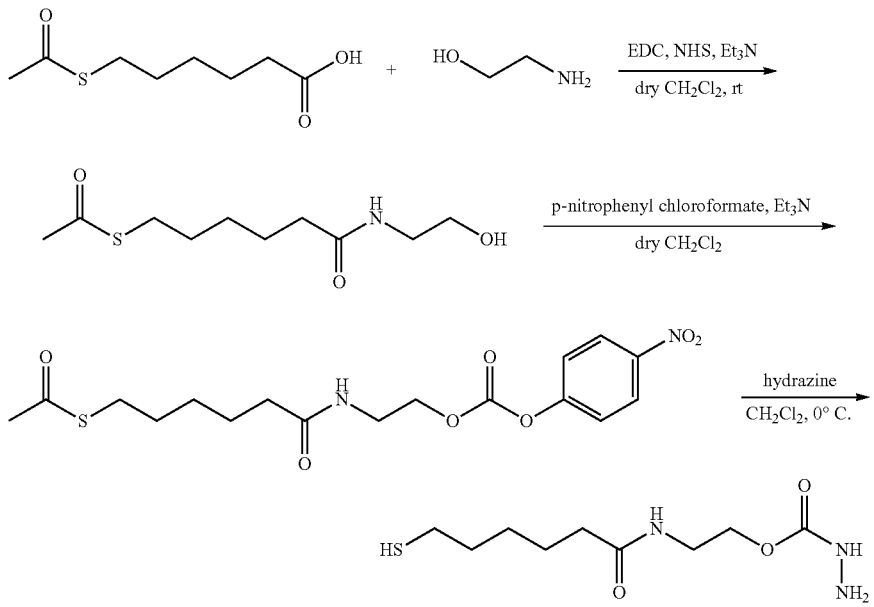

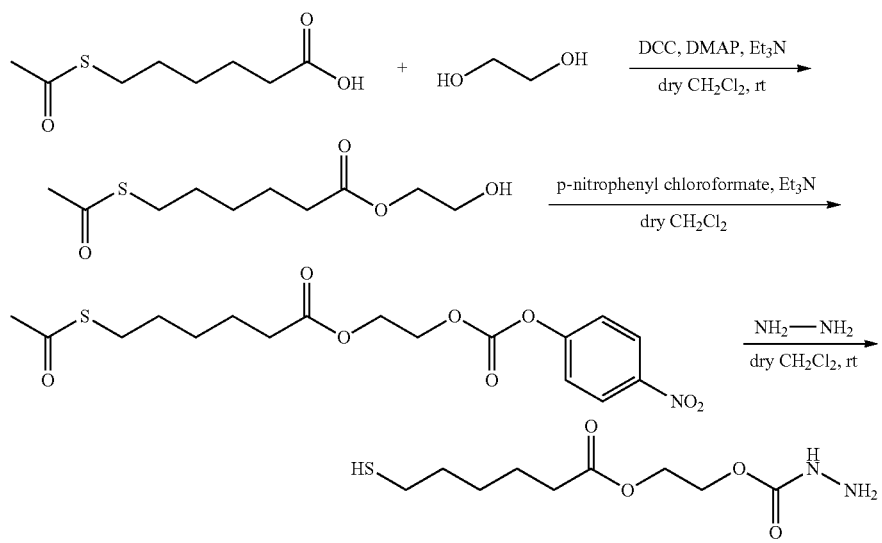

In some embodiments, the linker of the invention has the following formula:

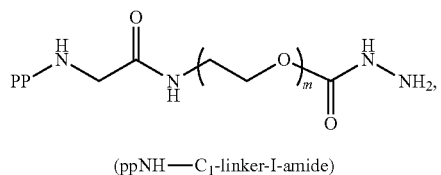

(ppNH—C$_1$-linker-I-amide)

wherein pp is a protecting group (such as Boc or Fmoc); and m is 1 to 12.

NH$_2$—C$_1$-linker-I-amide has formula (I) wherein X is pp-NH—; pp is a protecting group (such as Boc or Fmoc), n is 1, P is —C(O)NH—, R is a bond, Q is —R(CH$_2$CH$_2$O)$_m$—, and m is 1 to 12. Preferably, m is an integer of 1 to 6. More preferably, m is an integer of 2.

The linkers of NH$_2$—C$_1$-linker-I-amide of the present invention can be prepared using methods known to those skilled in the art in view of this disclosure. For example, the preferred linkers of the invention can be prepared as shown in the following scheme.

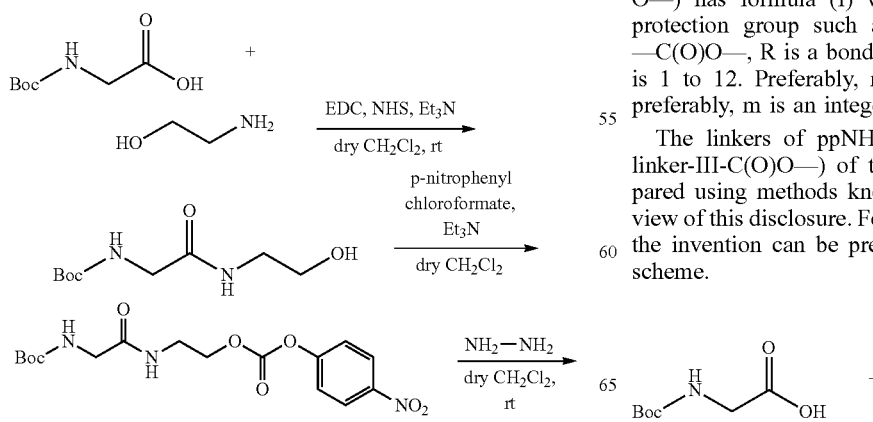

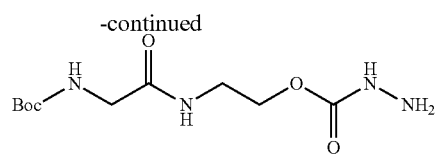

In some embodiments, the linker of the invention has the following formula:

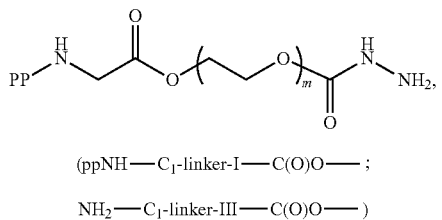

(ppNH—C$_1$-linker-I—C(O)O—;

NH$_2$—C$_1$-linker-III—C(O)O—)

wherein
PP is a protecting group (such as Boc or Fmoc); and m is 1 to 12.

ppNH-C$_1$-linker-I-C(O)O— (ppNH-C$_1$-linker-III-C(O)O—) has formula (I) wherein X is pp-NH— (pp is a protection group such as Boc or Fmoc), n is 1, P is —C(O)O—, R is a bond, Q is —R(CH$_2$CH$_2$O)$_m$—, and m is 1 to 12. Preferably, m is an integer of 1 to 6. More preferably, m is an integer of 2.

The linkers of ppNH-C$_1$-linker-I-C(O)O— (ppNH-C$_1$-linker-III-C(O)O—) of the present invention can be prepared using methods known to those skilled in the art in view of this disclosure. For example, the preferred linkers of the invention can be prepared as shown in the following scheme.

-continued

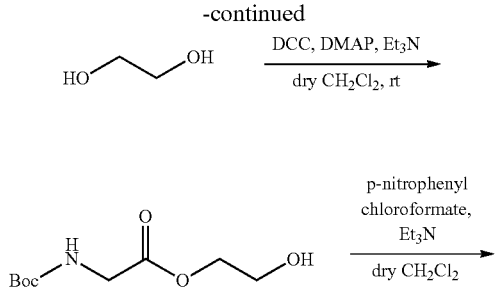

In some embodiments, the linker of the invention has the following formula:

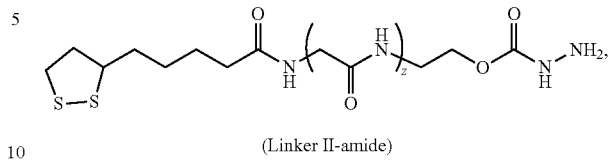

(Linker II-amide)

wherein z is 1 to 4.

Linker II-amide has formula (I) wherein X is

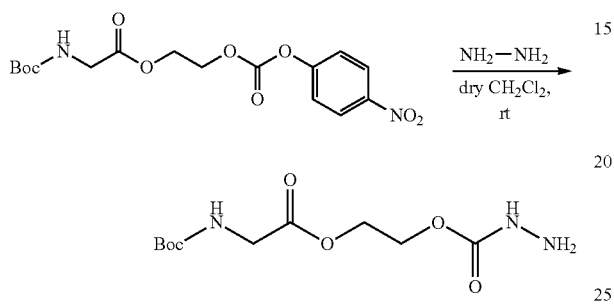

n is 4, P is —C(O)NH—, R is a bond, Q is R(—CH$_2$C(O)NH-)z, and z is 1 to 4. More preferably, z is an integer of 3.

The linkers of Linker II-amide of the present invention can be prepared using methods known to those skilled in the art in view of this disclosure. For example, the preferred linkers of the invention can be prepared as shown in the following scheme.

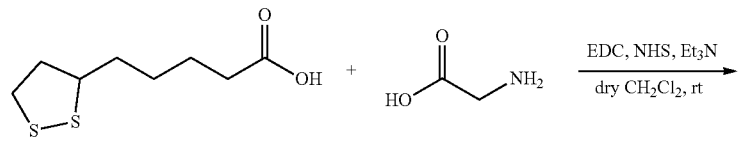

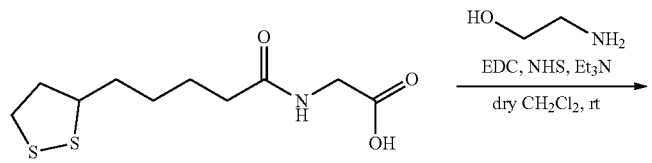

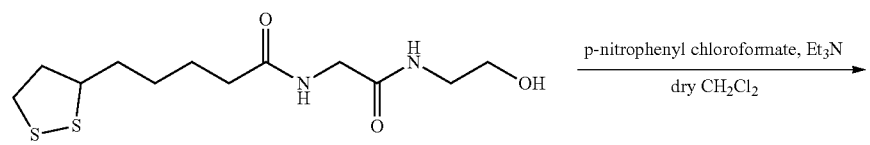

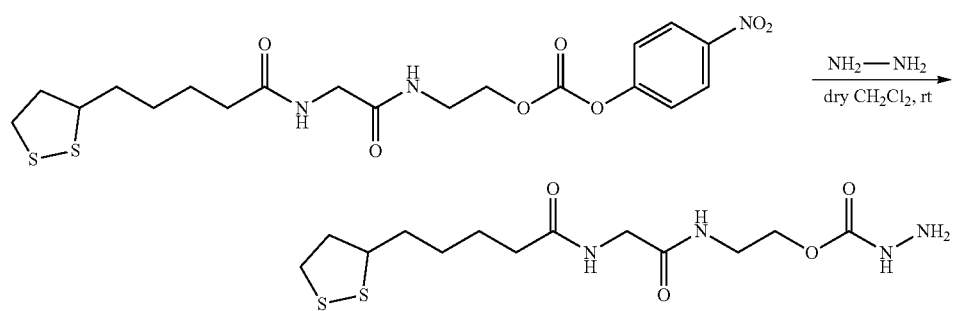

In some embodiments, the linker of the invention has the following formula:

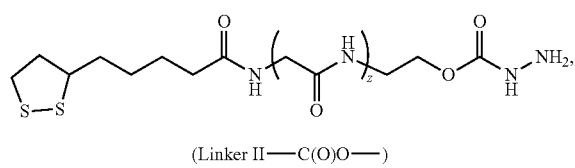

(Linker II—C(O)O—)

wherein z is 1 to 4.

Linker II-C(O)O— has formula (I) wherein X is

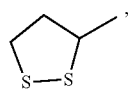

n is 4, P is —C(O)O—, R is a bond, Q is R(—CH$_2$C(O)NH-)z, and z is 1 to 4. More preferably, z is an integer of 3.

The linkers of Linker II-C(O)O— of the present invention can be prepared using methods known to those skilled in the art in view of this disclosure. For example, the preferred linkers of the invention can be prepared as shown in the following scheme.

In some embodiments, the linker of the invention has the following formula:

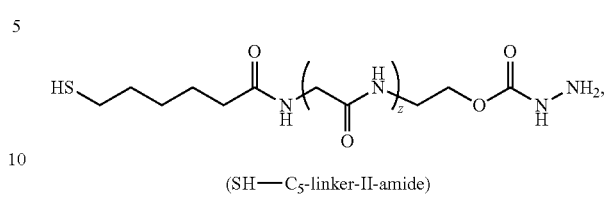

(SH—C$_5$-linker-II-amide)

wherein z is 1 to 4.

SH—C$_5$-linker-II-amide has formula (I) wherein X is —SH, n is 5, P is —C(O)NH—, R is a bond, Q is R(—CH$_2$C(O)NH-)z, and z is 1 to 4. More preferably, z is an integer of 3.

In other embodiment, n is 2. The linkers of SH—C$_{2-5}$-linker-II-amide of the present invention can be prepared using methods known to those skilled in the art in view of this disclosure. For example, the preferred linkers of the invention can be prepared as shown in the following scheme.

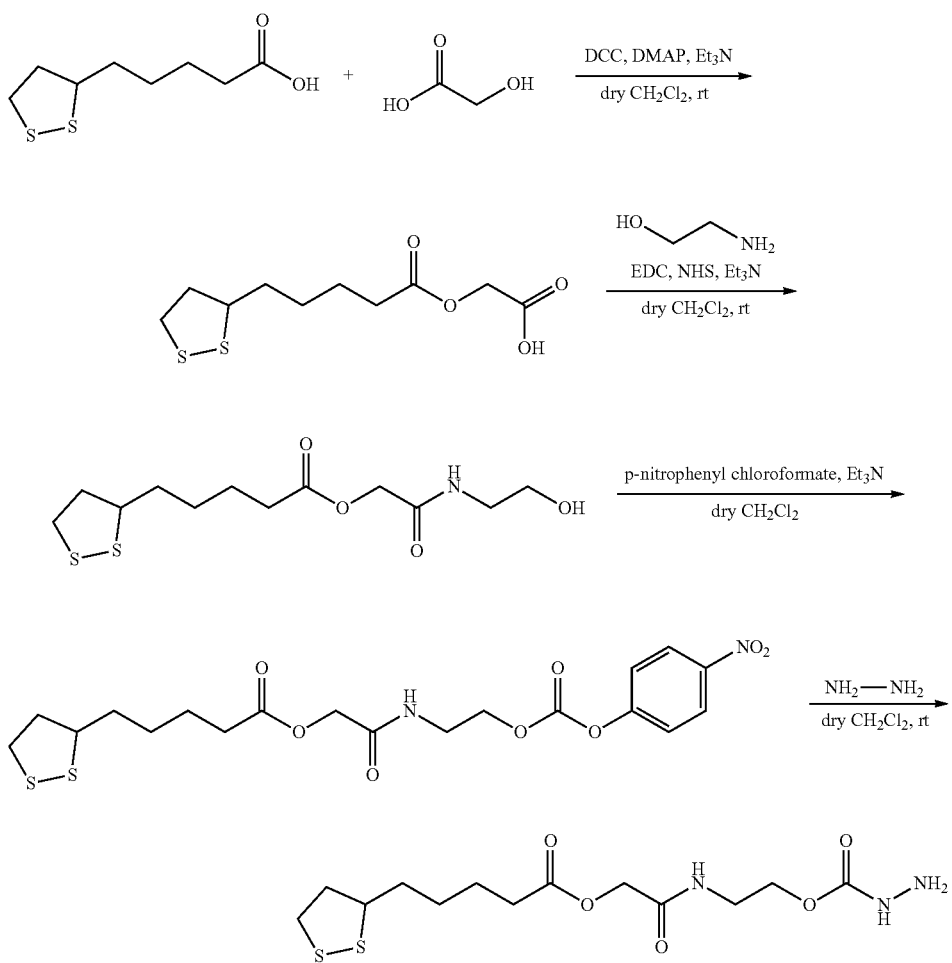

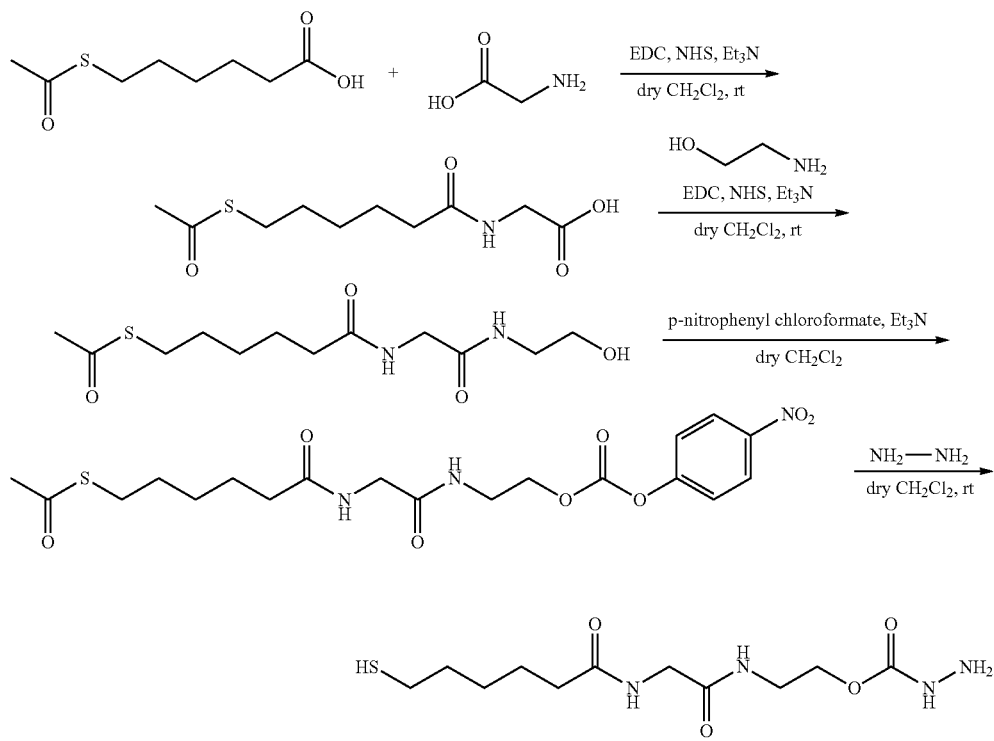

In some embodiments, the linker of the invention has the following formula:

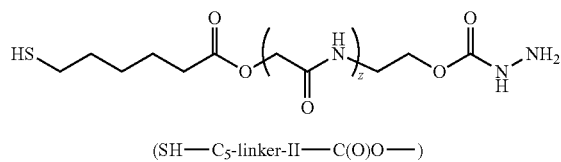

(SH—C$_5$-linker-II—C(O)O—)

wherein z is 1 to 4.

SH—C$_5$-linker-II-C(O)O— has formula (I) wherein X is CH$_3$C(O)S—, n is 5, P is —C(O)O—, R is a bond, Q is R(—CH$_2$C(O)NH-)z, and z is 1 to 4. More preferably, z is an integer of 3.

In other embodiment, n is 2. The linkers of SH—C$_{2-5}$-linker-II-C(O)O— of the present invention can be prepared using methods known to those skilled in the art in view of this disclosure. For example, the preferred linkers of the invention can be prepared as shown in the following scheme.

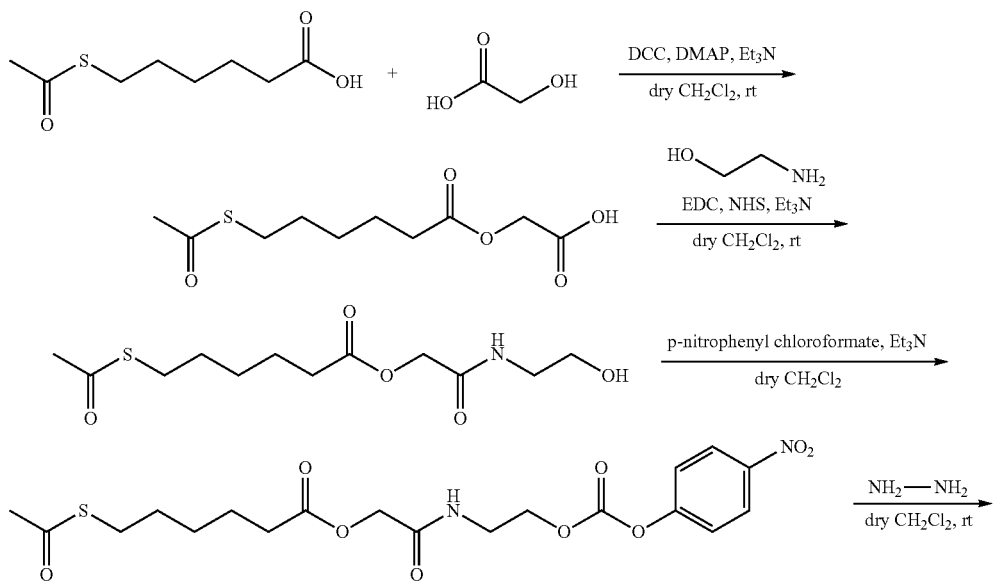

-continued

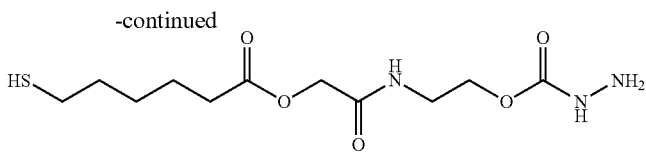

In some embodiments, the linker of the invention has the following formula:

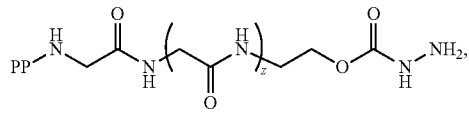

(ppNH—C$_1$-linker-II-amide)

wherein pp is a protection group (such as Boc or Fmoc); and z is 1 to 4.

ppNH-C$_1$-linker-II-amide has formula (I) wherein X is pp-NH—; pp is a protection group (such as Boc or Fmoc), n is 1, P is —C(O)NH—, R is a bond, Q is R(—C(O)NH-)z, and z is 1 to 4. More preferably, z is an integer of 3.

The linkers of ppNH-C$_1$-linker-II-amide of the present invention can be prepared using methods known to those skilled in the art in view of this disclosure. For example, the preferred linkers of the invention can be prepared as shown in the following scheme.

In some embodiments, the linker of the invention has the following formula:

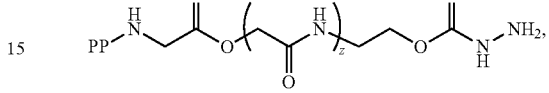

(ppNH—C$_1$-linker-II—C(O)O—)

wherein pp is a protection group (such as Boc or Fmoc); and z is 1 to 4.

ppNH-C$_1$-linker-II-C(O)O— has formula (I) wherein X is pp-NH—; pp is a protection group (such as Boc or Fmoc), n is 1, P is —C(O)O—, R is a bond, Q is R(—C(O)NH-)z, and z is 1 to 4. More preferably, z is an integer of 3.

The linkers of ppNH-C$_1$-linker-II-C(O)O— of the present invention can be prepared using methods known to those skilled in the art in view of this disclosure. For example, the preferred linkers of the invention can be prepared as shown in the following scheme.

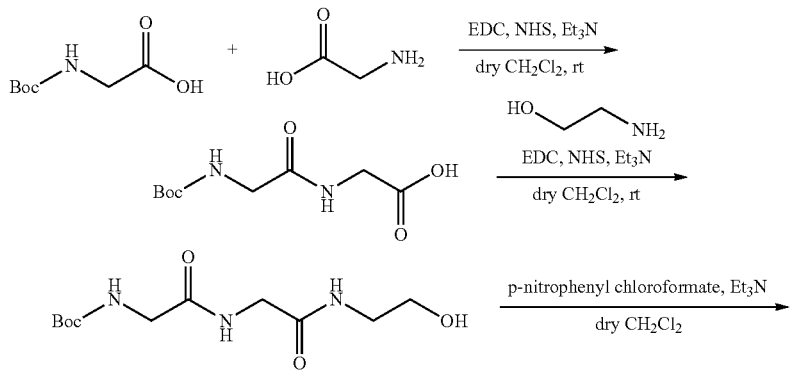

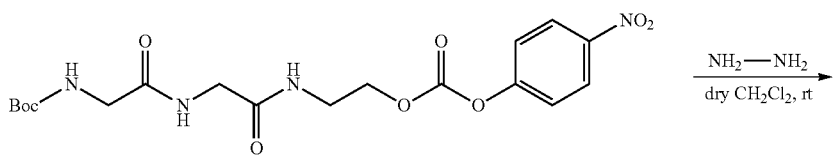

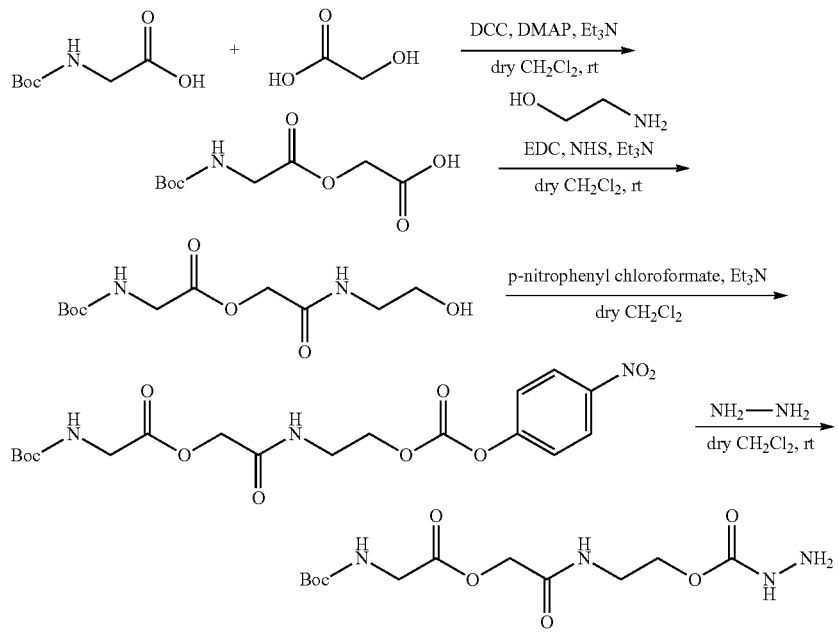

In some embodiments, the linker of the invention has the following formula:

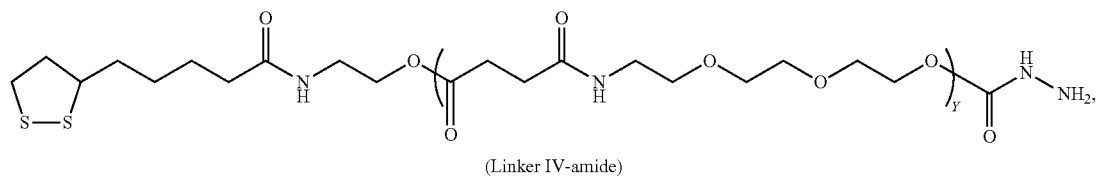

(Linker IV-amide)

wherein Y is 1 to 12.

Linker IV-amide has formula (I) wherein X is

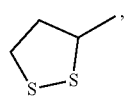

n is 4, P is —C(O)NH—, R is —CH$_2$CH$_2$O—, Q is —R[—C(O)CH$_2$CH$_2$—C(O)NH—(CH$_2$CH$_2$O)m]Y, m is 3 and Y is 1 to 12. Preferably, m is 2 and Y is 2.

In other embodiment, m is 1-12. The linkers of Linker IV-amide of the present invention can be prepared using methods known to those skilled in the art in view of this disclosure. For example, the preferred linkers of the invention can be prepared as shown in the following scheme.

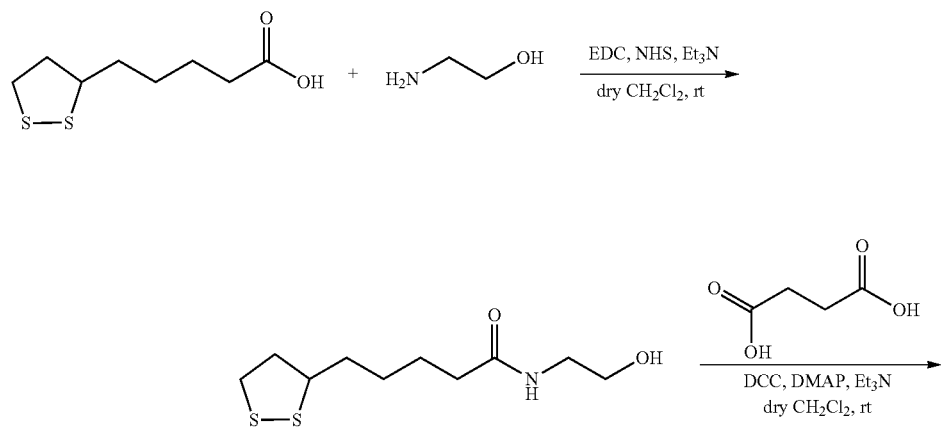

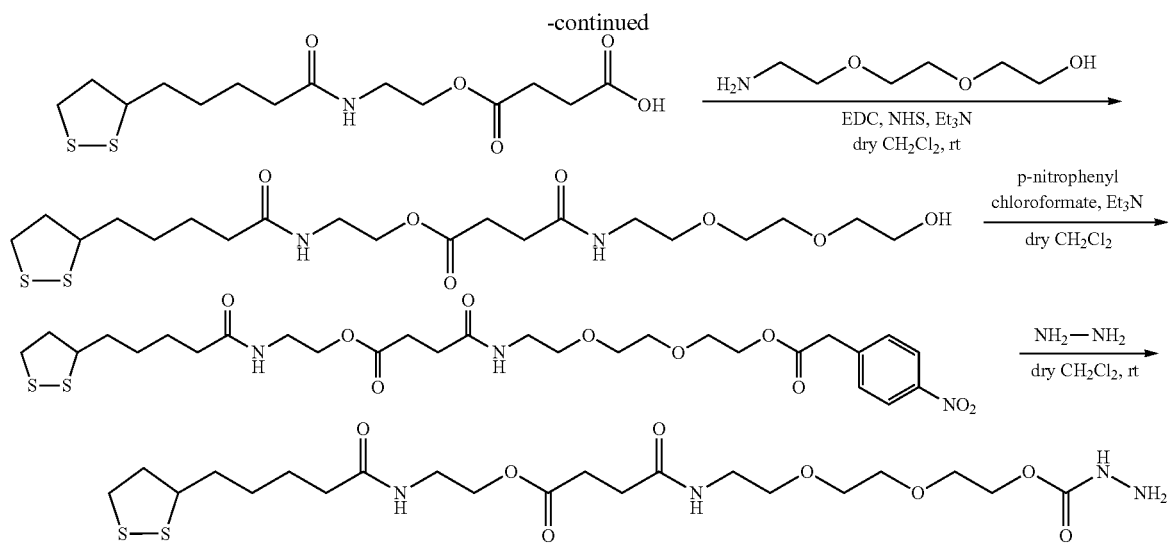

In some embodiments, the linker of the invention has the following formula:

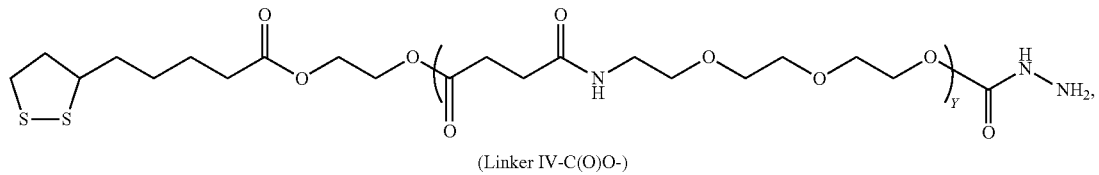
(Linker IV-C(O)O-)

wherein Y is 1 to 12.
Linker IV-C(O)O— has formula (I) wherein X is

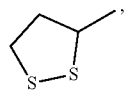

n is 4, P is —C(O)O—, R is —CH$_2$CH$_2$O—, Q is —R[—C(O)CH$_2$CH$_2$—C(O)NH—(CH$_2$CH$_2$O)$_m$]Y, m is 3 and Y is 1 to 12. More preferably, Y is an integer of 2.

In other embodiment, m is 1-12. The linkers of Linker IV-C(O)O— of the present invention can be prepared using methods known to those skilled in the art in view of this disclosure. For example, the preferred linkers of the invention can be prepared as shown in the following scheme.

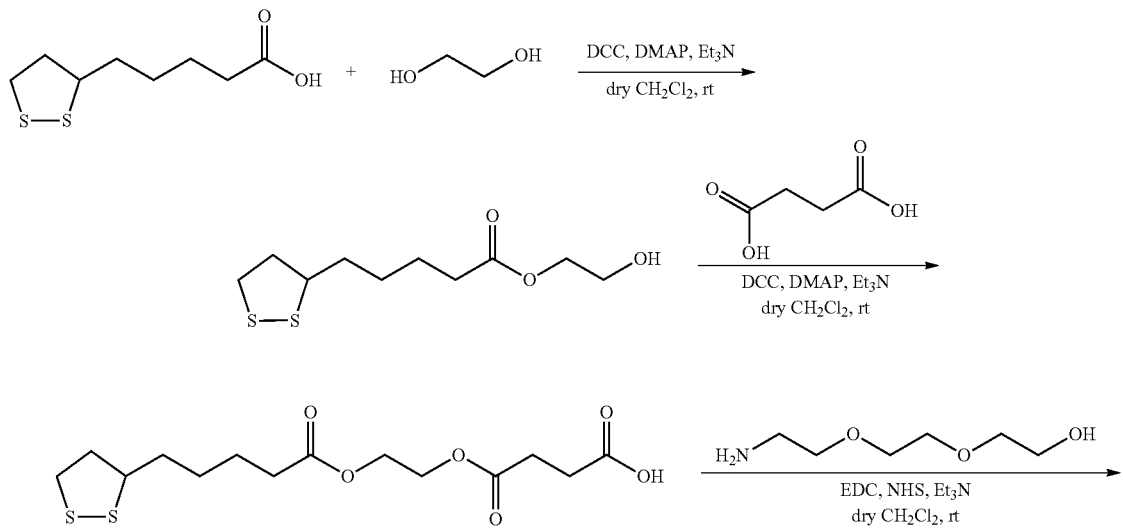

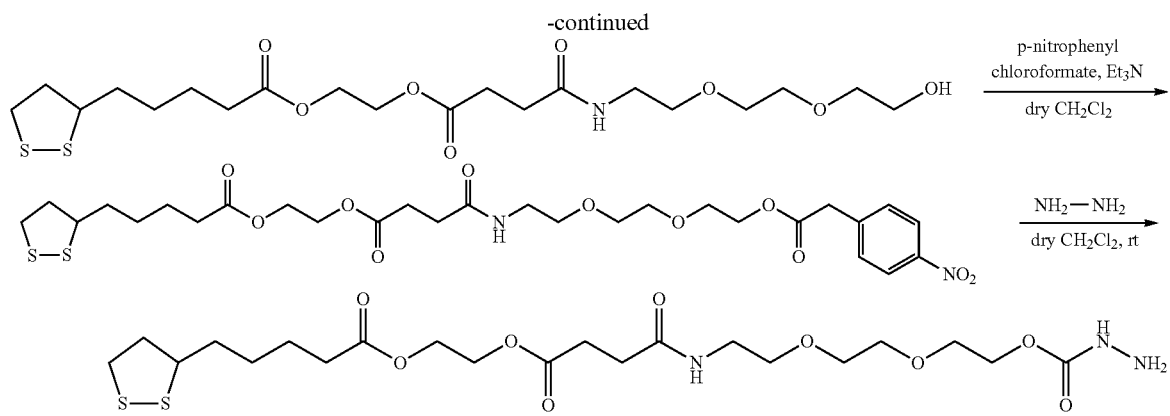

In some embodiments, the linker of the invention has the following formula:

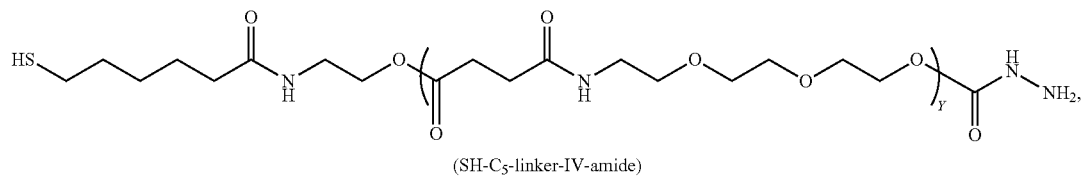

(SH-C₅-linker-IV-amide)

wherein Y is 1 to 12.

SH—C$_5$-linker-IV-amide has formula (I) wherein X is CH$_3$C(O)S—, n is 5, P is —C(O)NH—, R is —CH$_2$CH$_2$O—, Q is —R[—C(O)CH$_2$CH$_2$—C(O)NH—(CH$_2$CH$_2$O)$_m$]Y, m is 3 and Y is 1 to 12. More preferably, Y is an integer of 2.

In other embodiments, n is 2 or 5 and m is 1-12. The linkers of Linker SH—C$_{2-5}$-linker-IV-amide of the present invention can be prepared using methods known to those skilled in the art in view of this disclosure. For example, the preferred linkers of the invention can be prepared as shown in the following scheme.

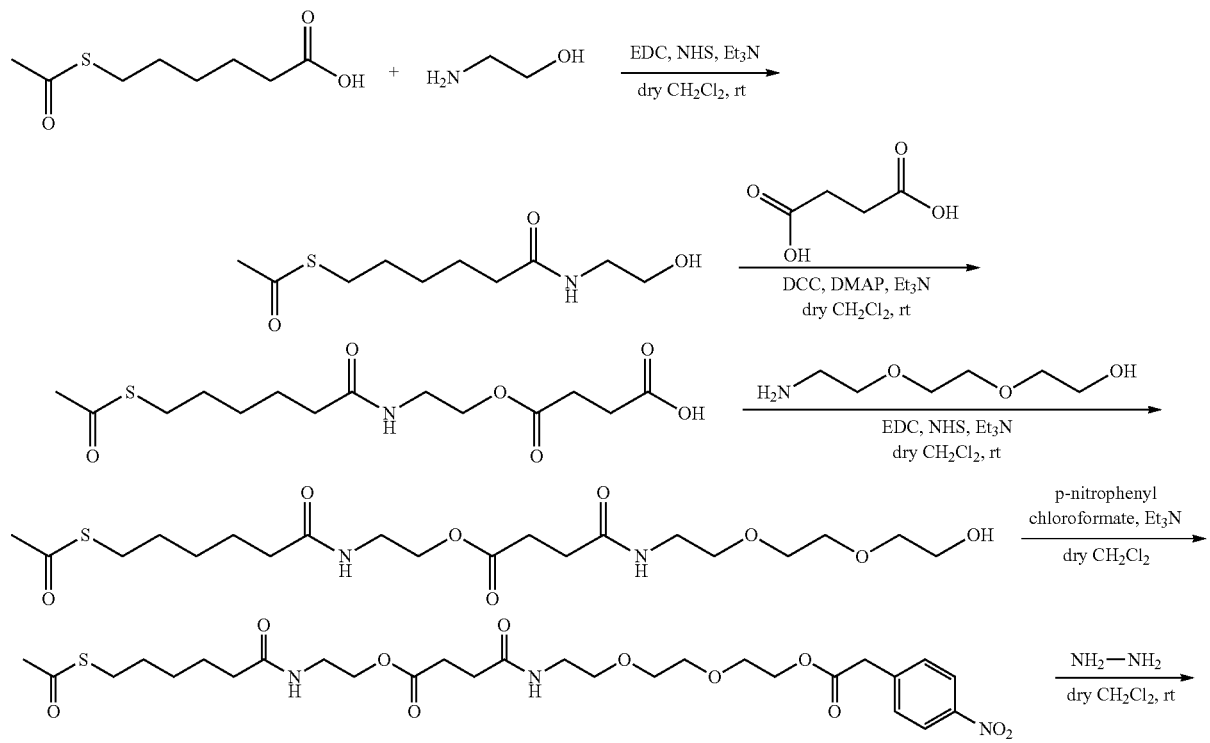

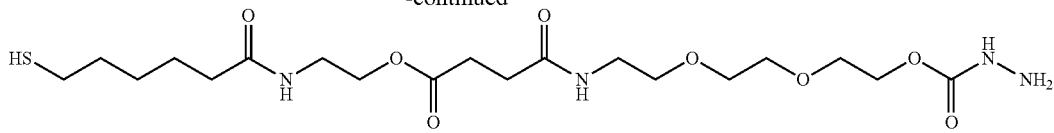

In some embodiments, the linker of the invention has the following formula:

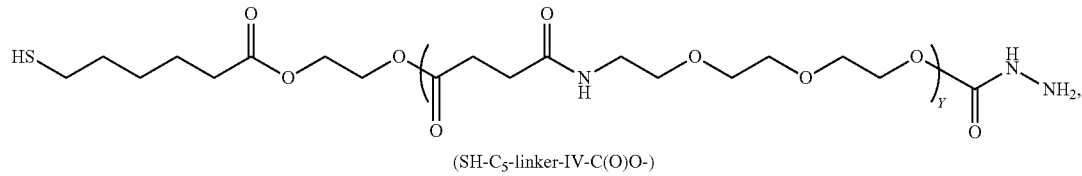

(SH-C$_5$-linker-IV-C(O)O-)

wherein Y is 1 to 12.

SH—C$_5$-linker-IV-C(O)O— has formula (I) wherein X is CH$_3$C(O)S—, n is 5, P is —C(O)O—, R is —CH$_2$CH$_2$O—, Q is —R[—C(O)CH$_2$CH$_2$—C(O)NH—(CH$_2$CH$_2$O)$_m$]Y, m is 3 and Y is 1 to 12. Preferably, Y is an integer of 1 to 6. More preferably, Y is an integer of 2.

In other embodiments, n is 2 or 5 and m is 1-12. The linkers of HS—C$_{2-5}$-linker-IV-C(O)O— of the present invention can be prepared using methods known to those skilled in the art in view of this disclosure. For example, the preferred linkers of the invention can be prepared as shown in the following scheme.

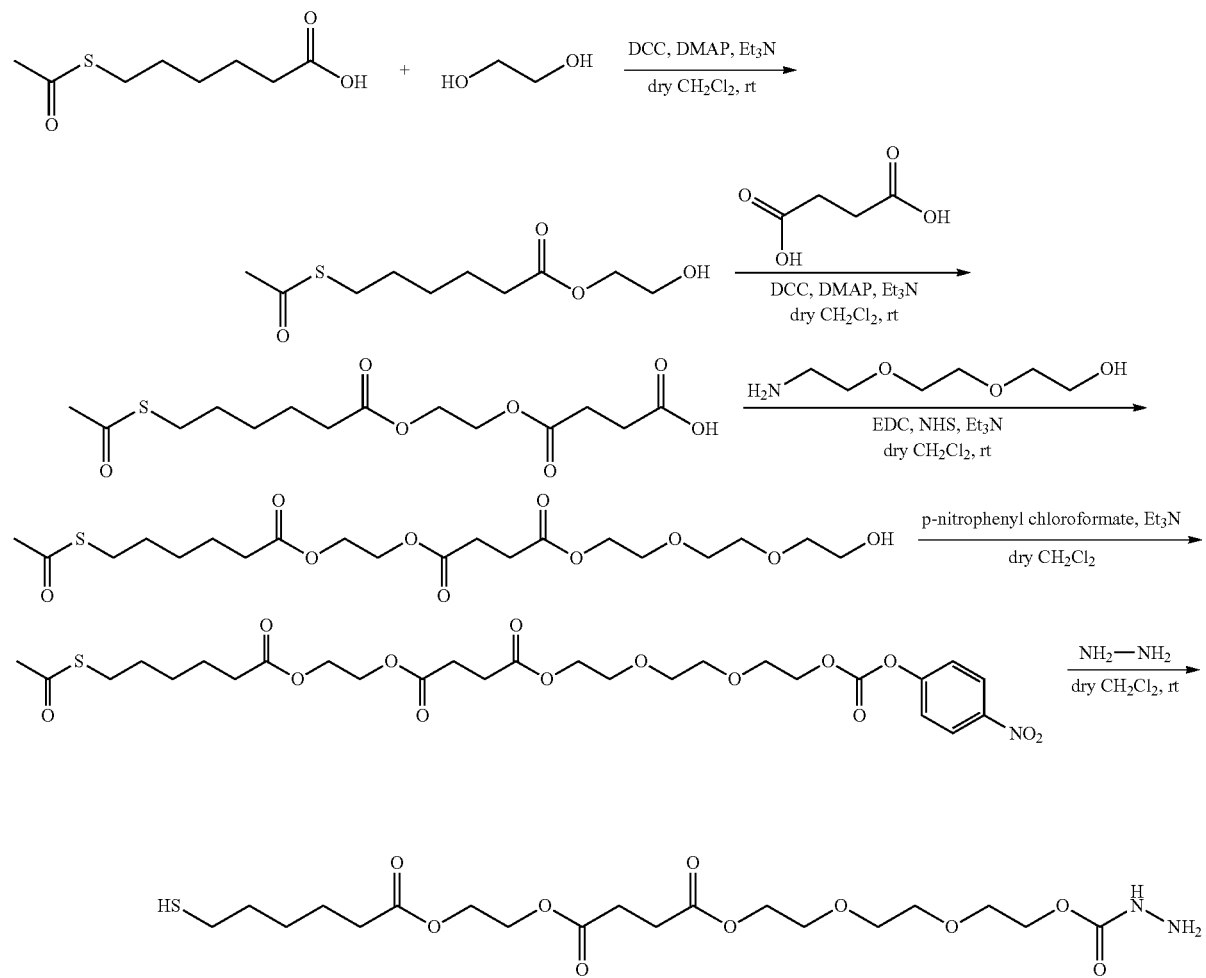

In some embodiments, the linker of the invention has the following formula:

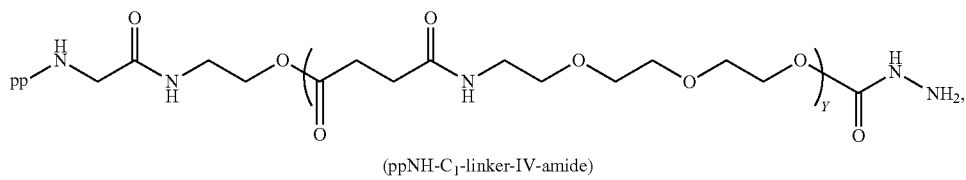

(ppNH-C$_1$-linker-IV-amide)

wherein pp is a protection group (such as Boc or Fmoc; and Y is 1 to 12.

ppNH-C$_1$-linker-IV-amide has formula (I) wherein X is pp-NH—; pp is a protecting group (such as Boc or Fmoc), n is 1, P is —C(O)NH—, R is —CH$_2$CH$_2$O—, Q is —R[—C(O)CH$_2$CH$_2$—C(O)NH—(CH$_2$CH$_2$O)$_m$]Y, m is 3 and Y is 1 to 12. More preferably, Y is an integer of 2.

In other embodiments, m is 1-12. The linkers of ppNH-C$_1$-linker-IV-amide of the present invention can be prepared using methods known to those skilled in the art in view of this disclosure. For example, the preferred linkers of the invention can be prepared as shown in the following scheme.

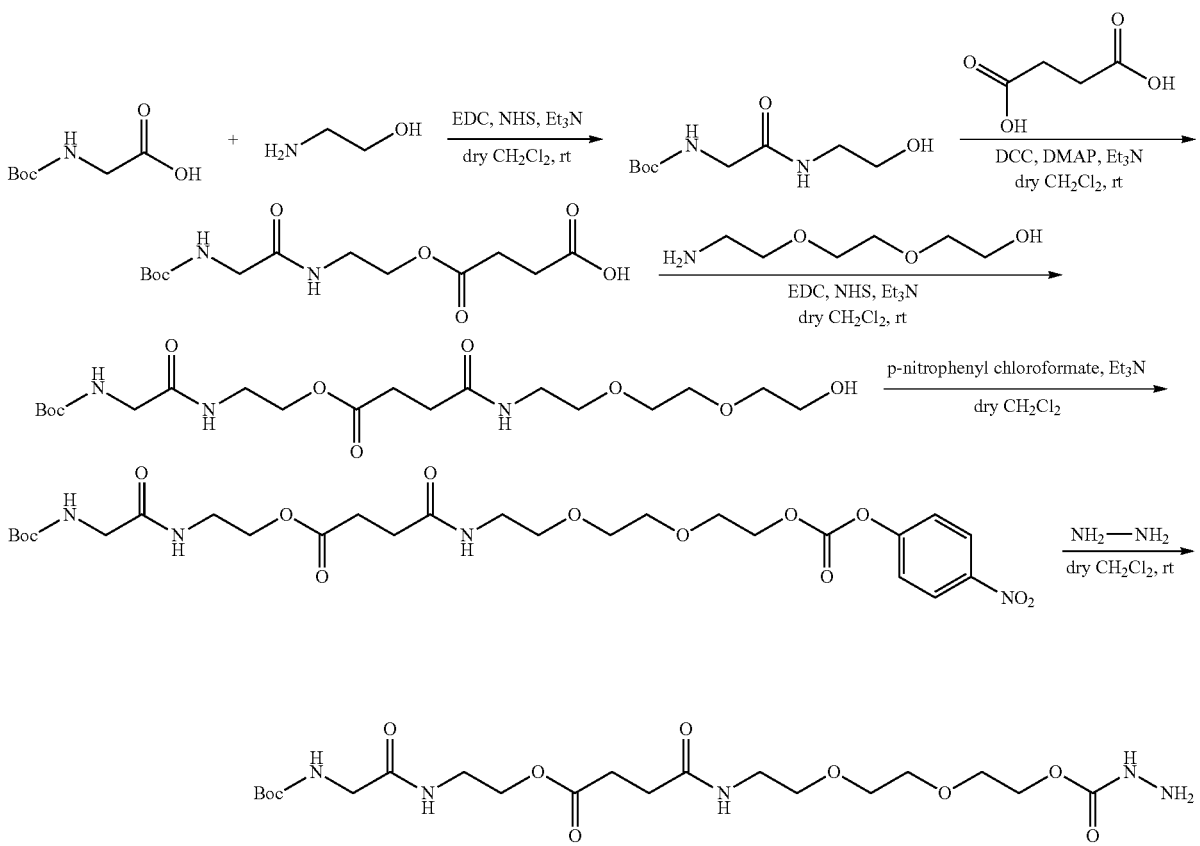

In some embodiments, the linker of the invention has the following formula:

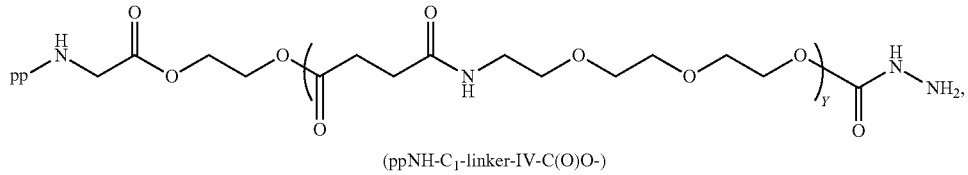

(ppNH-C$_1$-linker-IV-C(O)O-)

wherein pp is a protection group (such as Boc or Fmoc); and Y is 1 to 12.

ppNH-C$_1$-linker-IV-C(O)O— has formula (I) wherein X is pp-NH—; pp is a protection group (such as Boc or Fmoc), n is 1, P is —C(O)O—, R is —CH$_2$CH$_2$O—, Q is —R[—C(O)CH$_2$CH$_2$—C(O)NH—(CH$_2$CH$_2$O)$_m$]Y, m is 3 and Y is 1 to 12. More preferably, Y is an integer of 2.

In other embodiments, m is 1-12. The linkers of ppNH-C$_1$-linker-IV-C(O)O— of the present invention can be prepared using methods known to those skilled in the art in view of this disclosure. For example, the preferred linkers of the invention can be prepared as shown in the following scheme.

(ethylene glycol) repeat units may increase plasma half-life of the polymeric conjugate, for instance, by decreasing the uptake of the polymeric conjugate by the phagocytic system while decreasing transfection/uptake efficiency by cells. Those of ordinary skill in the art will know of methods and techniques for PEGylating a polymer, for example, by using EDC (1-ethyl-3-(3-dimethylaminopropyl) carbodiimide hydrochloride) and NHS(N-hydroxysuccinimide) to react a polymer to a PEG group terminating in an amine, as discussed in the examples below, by ring opening polymerization techniques (ROMP), or the like.

In another one embodiment, the metallic nanoparticle is in a size less than about 100 nm, preferably, less than 80 nm.

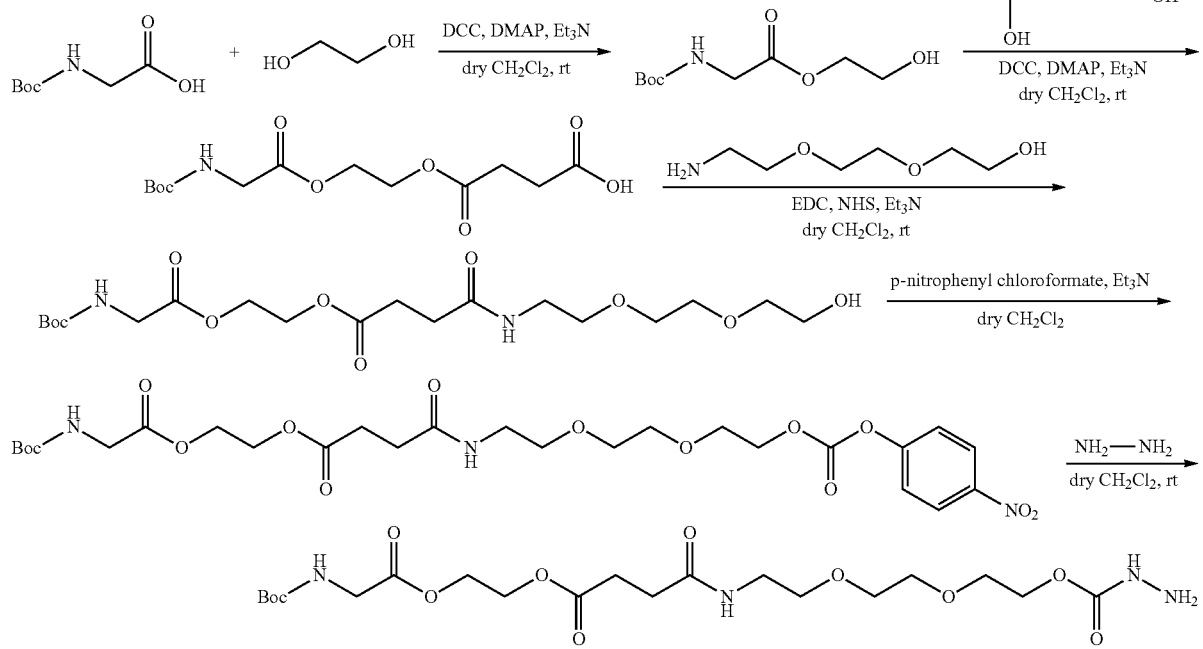

In another aspect, the invention provides a metallic nanoparticle complex, comprising a metallic nanoparticle complexed with one or more linkers of the invention, optionally complexed with one or more PEGs.

In one embodiment, the metallic nanoparticle is Au, Pd, Pt or Ag nanoparticle.

In one embodiment, the linker is same or different. More preferably, the metallic nanoparticle complex comprises plural linkers with different molecular length. The linkers with different molecular length can bind different therapeutic or diagnostic agent depending on the requirement on a target cell or disease to be treated or diagnosed. The linker links to the metallic nanoparticle through the sulfur atoms of 1,2-dithiolane group or —SH group in the linker.

In one embodiment, the molecular weight of PEG used in the invention ranges from about 2000 to 20,000 Da; preferably, 2000 to 5000. PEGylation may also be used, in some cases, to decrease charge interaction between a linker or a nanoparticle and a biological moiety, e.g., by creating a hydrophilic layer on the surface of the linker or nanoparticle, which may shield the polymer from interacting with the biological moiety. In some cases, the addition of poly In some embodiment, the metallic nanoparticle complex further links one or more same of different therapeutic or diagnostic agents. Preferably, the therapeutic agent is anti-tumor drug or an antibody. Preferably, the antibody is an antibody targeted to an antigen specific expression in cell surface such as tumor cells; more preferably, the antibody is possessed a targeting, recognizing, and anti-tumor cell antibody.

In some embodiments, the anti-tumor drug is an anti-cancer drug or anti-cancer antibody useful in the treatment of cancer. Examples of anti-cancer drugs include alkylating agents such as thiotepa and cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol); beta-lapachone; lapachol; colchicines; betulinic acid; a camptothecin (including the synthetic analogue topotecan, CPT-11 (irinotecan), acetylcamptothecin, scopolectin, and 9-aminocamptothecin);

bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed. Engl., 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); thiotepa; taxoids, e.g., paclitaxel (Bristol-Myers Squibb Oncology, Princeton, N.J.), Cremophor-free, albumin-engineered nanoparticle formulation of paclitaxel (American Pharmaceutical Partners, Schaumberg, Ill.), and doxetaxel (Rhone-Poulenc Rorer, Antony, France); chloranbucil; gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; oxaliplatin; leucovovin; vinorelbine; novantrone; edatrexate; daunomycin; aminopterin; ibandronate; topoisomerase inhibitor RFS 2000; difluoromethylornithine (DMFO); retinoids such as retinoic acid; capecitabine; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin combined with 5-FU and leucovovin.

The amount of an anti-cancer drug present in the nanoparticle can vary over a wide range. In some embodiments, the nanoparticle can include an amount of the anticancer drug in the range of about 1% to about 50% (weight/weight) based on the mass ratio of the anticancer drug to the nanoparticle. In other embodiments, the nanoparticle can include an amount of the anticancer drug in the range of about 5% to about 40% (weight/weight) based on the mass ratio of the anticancer drug to the nanoparticle. In still other embodiments, the nanoparticle can include an amount of the anticancer drug in the range of about 10% to about 30% (weight/weight). In yet still other embodiments, the nanoparticle can include an amount of the anticancer drug in the range of about 1% to about 10% (weight/weight), about 1% to about 5% (weight/weight), about 5% to about 10% (weight/weight), about 10% to about 20% (weight/weight), about 15% to about 35% (weight/weight), about 30% to about 40% (weight/weight) and the like, based on the mass ratio of the anticancer drug to the nanoparticle. In some embodiments, the nanoparticle can include an amount of the anticancer drug in about 20% (weight/weight) based on the mass ratio of the anticancer drug to the nanoparticle. In other embodiments, the nanoparticle can include an amount of the anticancer drug of 5% (weight/weight), about 10% (weight/weight) 15% (weight/weight), about 25% (weight/weight), about 30% (weight/weight) and the like based on the mass ratio of the anticancer drug to the nanoparticle.

Some embodiments described herein relate to a composition that can comprise one or more metallic nanoparticle complex linking one or more same of different therapeutic or diagnostic agents and a pharmaceutically acceptable carrier. The pharmaceutical composition facilitates administration of a metallic nanoparticle complex linking one or more same of different therapeutic or diagnostic agents to an organism. Multiple techniques of administering a compound exist in the art including, but not limited to, oral, injection, aerosol, parenteral, and topical administration.

Some embodiment described herein relate to a drug delivery system, comprising one or more metallic nanoparticle complex linking one or more same of different therapeutic or diagnostic agents.

Multiple techniques of administering a metallic nanoparticle complex linking one or more same of different therapeutic or diagnostic agents exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections.

EXAMPLE

Example 1 Preparation of Linker 1-Amide

Step 1. The ethanolamine (1.28 g, 1.05 eq) and Lipoic acid (4.13 g, 1.0 eq) were dissolved in 80 mL DCM, and EDC.HCl (4.98 g, 1.3 eq), hydroxysuccinimide (NHS)(2.30 g, 1.0 eq) and triethylamine (6.4 mL, 2.3 eq) were slowly added. The reaction was carried out at room temperature for at least 5 hrs and the reaction was followed by TLC. Subsequently, the mixture was quenched by adding ddH$_2$O, and was extracted 2-3 times with DCM. The organic layer was collected, dried with anhydrous magnesium sulfate, filtered with MgSO4 and then removal of DCM. The extract is purified with the column by using DCM:MeOH=9.8:0.2. The product was a pale yellow liquid. Yield: 4.04 g; 81.0%.

Step 2. The 4-nitrophenyl chloroformate (3.35 g, 1.15 eq) was placed in two-neck bottle. Under vacuum for 1 hr, the three-way valve was diverted to nitrogen device and 60 mL DCM was added with a syringe. The weighted Step 1 Product 1 was dissolved with 10-15 mL DCM, injected into the reaction flask with a syringe, and then slowly added with triethylamine (4.5 mL, 2.3 eq). The reaction was carried out in an ice bath for about 1 hr and then back to room temperature for overnight. After completion of the reaction, the mixture was quenched by adding ddH₂O, and was extracted 3 times with DCM. The organic layer was collected, dried with anhydrous magnesium sulfate, filtered with MgSO₄ and then removal of DCM. The extract is purified with the column by using EtOAc:Hex:MeOH=1:1:0.2. The product was a pale yellow liquid. After purification yield: 51.6%.

Step 3. The weighted Step 2 Product 2 (3.5 g, 1.0 eq) was dissolved in 120 mL DCM, and then slowly added with Hydrazine hydrate (6.5 mL, 10.0 eq). The reaction was carried out at room temperature for about 24 hrs. The solution color turned from pale yellow to orange. After completion of the reaction, the mixture was quenched by adding ddH₂O, and was extracted 2-3 times with DCM. The organic layer was collected, dried with anhydrous magnesium sulfate, filtered with MgSO₄ and then removal of DCM. The extract was purified with the column by using DCM:MeOH=9.5:0.5. In this step, the product was stuck in the column and the MeOH can be increased to 5% to elute the final product. The product was a pale yellow sticky solid. After purification yield: 19.5%.

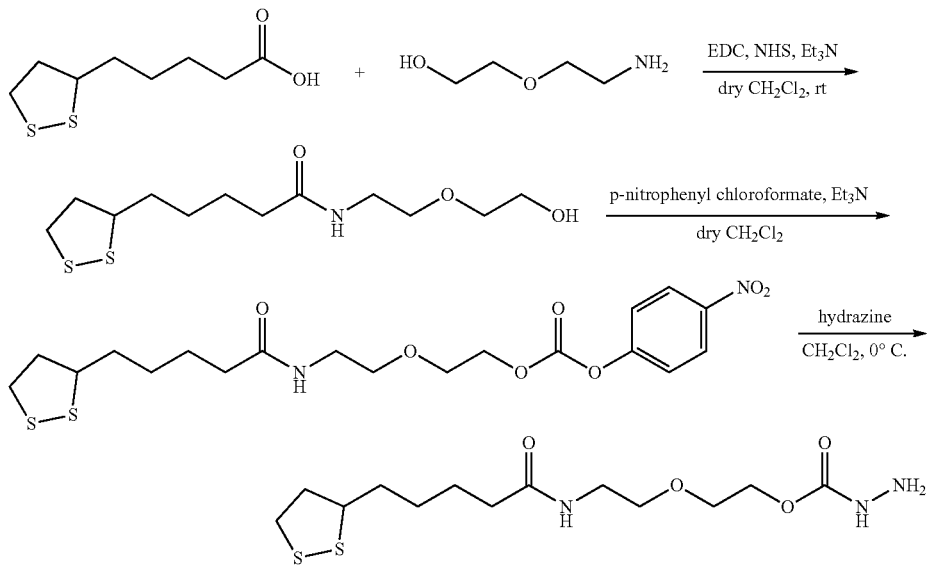

Linker I-1

Linker I-1 (Linker I-amide, m=2). $^1$H (400 MHz) δ1.23-1.31 (2H, m), 1.40-1.51 (3H, m), 1.57-1.64 (1H, m), 1.78-1.86 (1H, m), 2.05 (2H, t), 2.32-2.39 (1H, m), 3.01-3.18 (4H, m), 3.39 (2H, t), 3.52-3.57 (3H, m), 4.03-4.19 (4H, m), 7.94 (1H, s), 8.14 (1H, s). $^{13}$C (100 MHz) δ25.9, 29.0, 34.8, 36.1, 38.9, 39.5, 40.9, 57.2, 64.7, 69.3, 69.6, 159.5, 174.9 ppm. H-Mass (m/z): (M+Na)=374.1171

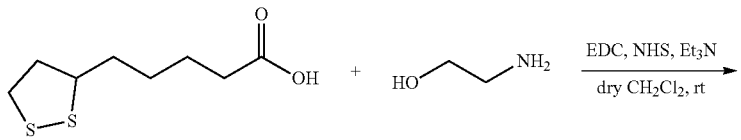

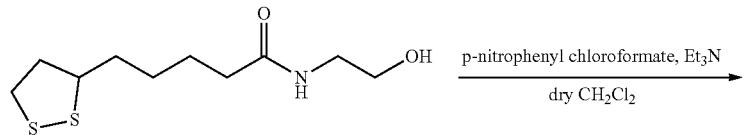

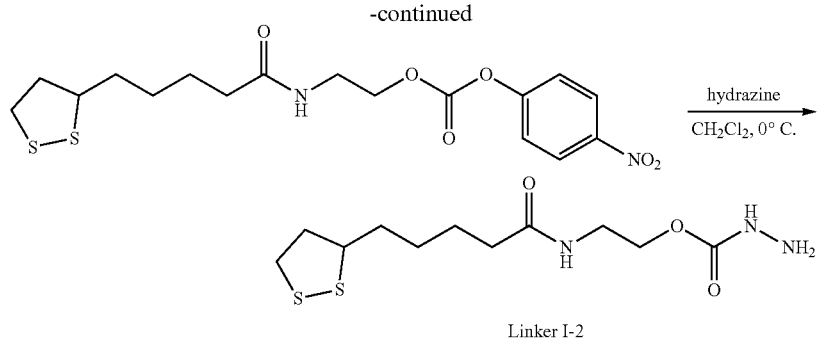
Linker I-2 (Linker I-amide, m=1). $^1$H (300 MHz) δ1.30-1.38 (2H, m), 1.45-1.57 (3H, m), 1.60-1.72 (1H, m), 1.80-1.92 (1H, m), 2.06 (2H, s), 2.36-2.46 (1H, m), 3.07-3.24 (4H, m), 3.56-3.65 (1H, m), 3.95 (2H, t), 4.02 (2H, s), 7.88 (1H, t), 8.11 (1H, s). $^{13}$C (100 MHz) δ25.6, 28.8, 34.6, 35.9, 38.8, 39.4, 40.7, 56.9, 63.7, 163.8, 174.3 ppm. H-Mass (m/z): (M+Na)=330.0894.
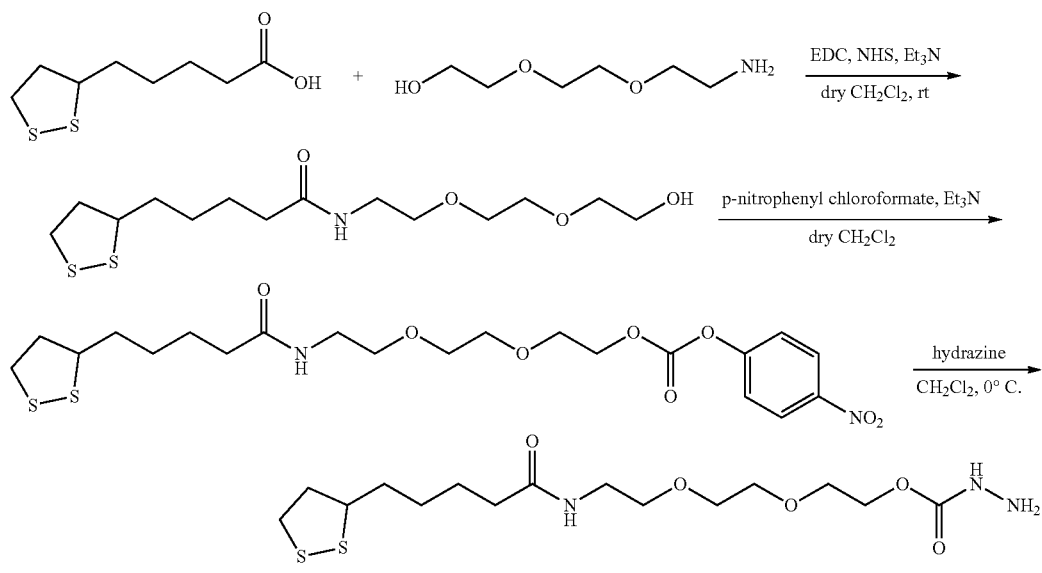
Linker I-3 (Linker I-amide, m=3). $^1$H (300 MHz) δ1.30-1.37 (2H, m), 1.45-1.57 (3H, m), 1.60-1.72 (1H, m), 1.80-1.91 (1H, m), 2.06 (2H, t), 2.35-2.46 (1H, m), 3.07-3.23 (4H, m), 3.39 (2H, t), 3.47-3.65 (7H, m), 4.02 (2H, s), 4.05-4.08 (2H, m), 7.84 (1H, t), 8.18 (1H, s). $^{13}$C (100 MHz) δ25.7, 28.9, 34.7, 35.9, 38.8, 39.4, 40.7, 60.0, 64.4, 69.4, 69.6, 70.1, 70.3, 159.2, 174.2 ppm. H-Mass (m/z): (M+Na)=418.1466.
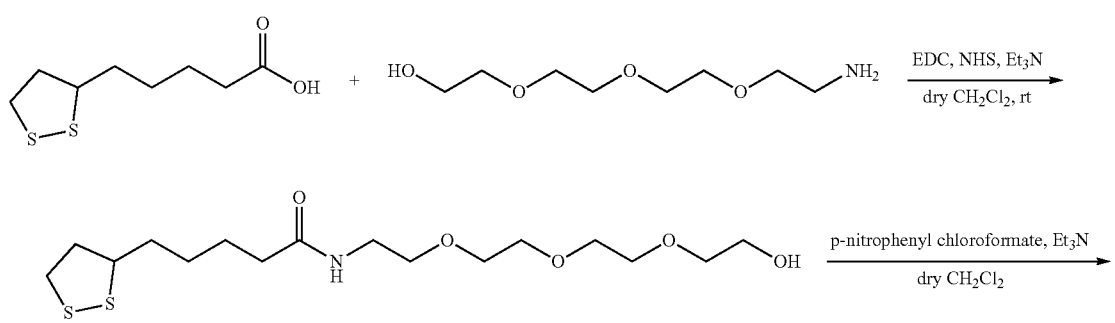

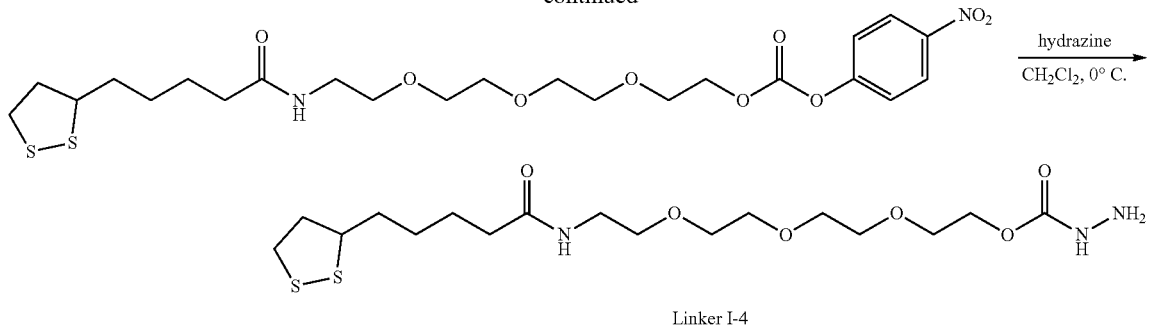

Linker I-4

Linker I-4 (Linker I-amide, m=4). $^1$H (300 MHz) δ1.30-1.38 (2H, m), 1.45-1.57 (3H, m), 1.60-1.72 (1H, m), 1.80-1.91 (1H, m), 2.06 (2H, t), 2.36-2.46 (1H, m), 3.07-3.23 (4H, m), 3.39 (2H, t), 3.49-3.65 (11H, m), 4.02 (2H, s), 4.05-4.08 (2H, m), 7.83 (1H, t), 8.18 (1H, s). $^{13}$C (100 MHz) δ25.7, 28.9, 34.7, 35.9, 38.8, 39.4, 40.7, 56.9, 64.4, 69.4, 69.6, 70.2, 70.3, 70.4, 159.2, 174.1 ppm. H-Mass (m/z): (M+Na)= 440.1875.

reaction was carried out at room temperature for at least 5 hrs and the reaction was followed by TLC. Subsequently, the mixture was quenched by adding ddH$_2$O, and was extracted 2-3 times with DCM. The organic layer was collected, dried with anhydrous magnesium sulfate, filtered with MgSO$_4$ and then removal of DCM. The extract is purified with the column by using DCM:MOH=9.8:0.2. The product was a pale yellow liquid. Yield: 4.00 g; 80.5%.

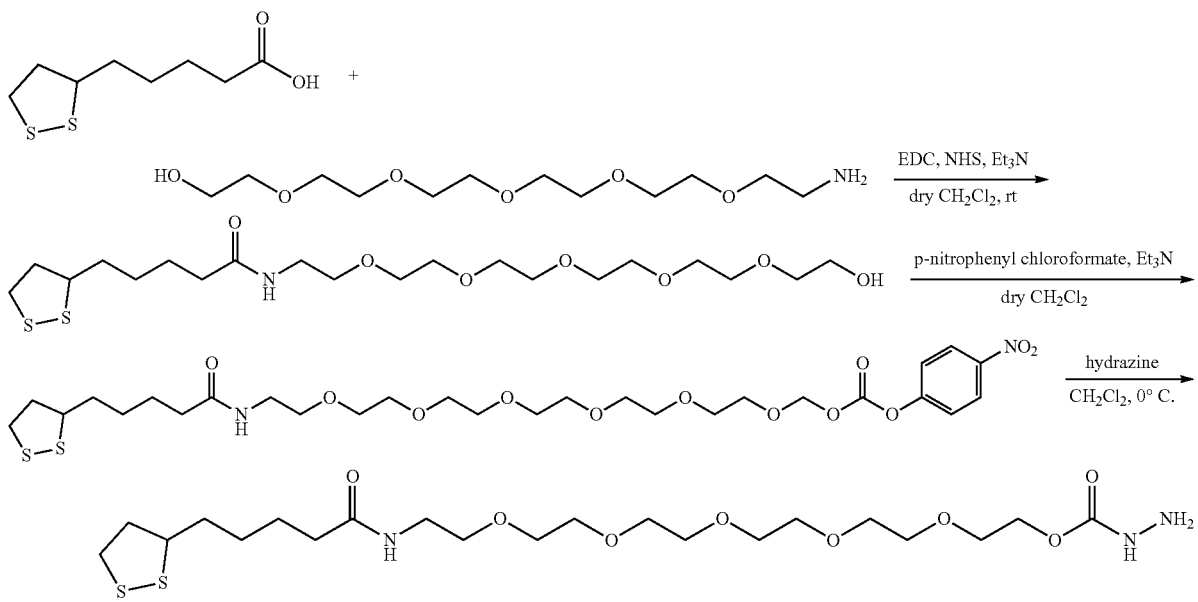

Linker I-5

Linker I-5 (Linker 1-amide, m=5). $^1$H (300 MHz) δ1.30-1.38 (2H, m), 1.45-1.57 (3H, m), 1.60-1.69 (1H, m), 1.80-1.91 (1H, m), 2.06 (2H, t), 2.36-2.46 (1H, m), 3.07-3.23 (4H, m), 3.39 (2H, t), 3.51-3.62 (19H, m), 4.02 (2H, s), 4.05-4.08 (2H, m), 4.83 (1H, t), 8.18 (1H, s). $^{13}$C (100 MHz) δ25.9, 29.0, 34.8, 36.1, 39.0, 39.4, 40.9, 57.2, 64.8, 69.5, 69.7, 70.3, 70.4, 70.5, 159.5, 174.8 ppm. H-Mass (m/z): (M+Na)=550.2234

Example 2 Preparation of Linker I-C(O)O

Step 1. The ethylene glycol (1.30 g, 1.05 eq) and Lipoic acid (4.13 g, 1.0 eq) were dissolved in 80 mL DCM, and N,N'-Dicyclohexylcarbodiimide (DCC) (5.36 g, 1.3 eq), 4-(Dimethylamino)pyridine (DMAP) (0.24 g, 0.1 eq) and triethylamine (6.4 mL, 2.3 eq) were slowly added. The Step 2. The 4-nitrophenyl chloroformate (3.35 g, 1.15 eq) was placed in two-neck bottle. Under vacuum for 1 hr, the three-way valve was diverted to nitrogen device and 60 mL DCM was added with a syringe. The weighted Step 1 Product 1 was dissolved with 10-15 mL DCM, injected into the reaction flask with a syringe, and then slowly added with triethylamine (4.5 mL, 2.3 eq). The reaction was carried out in an ice bath for about 1 hr and then back to room temperature for overnight. After completion of the reaction, the mixture was quenched by adding ddH$_2$O, and was extracted 2-3 times with DCM. The organic layer was collected, dried with anhydrous magnesium sulfate, filtered with MgSO$_4$ and then removal of DCM. The extract is purified with the column by using EtOAc:Hex:MeOH=1:1:0.2. The product was a pale yellow liquid. After purification yield: 50.6%.

Step 3. The weighted Step 2 Product 2 (3.5 g, 1.0 eq) was dissolved in 120 mL DCM, and then slowly added with Hydrazine hydrate (6.5 mL, 10.0 eq). The reaction was carried out at room temperature for about 24 hrs. The solution color turned from pale yellow to orange. After completion of the reaction, the mixture was quenched by adding ddH$_2$O, and extracted 2-3 times with DCM. The organic layer was collected, dried with anhydrous magnesium sulfate, filtered with MgSO$_4$ and then removal of DCM. The extract was purified with the column by using DCM:MeOH=9.5:0.5. In this step, the product was stuck in the column and the MeOH can be increased to 5% to elute the final product. The product was a pale yellow sticky solid. After purification yield: 18.5%.

Example 3 Preparation of HS—C$_2$-Linker-I-Amide

Step 1. The ethanolamine (1.28 g, 1.05 eq) and 3-(Acetylthio)propionic acid (2.96 g, 1.0 eq) were dissolved in 80 mL DCM, and EDC.HCl (4.98 g, 1.3 eq), hydroxysuccinimide (NHS)(2.30 g, 1.0 eq) and triethylamine (6.4 mL, 2.3 eq) were slowly added. The reaction was carried out at room temperature for at least 5 hrs and the reaction was followed by TLC. Subsequently, the mixture was quenched by adding ddH$_2$O, and was extracted 2-3 times with DCM. The organic layer was collected, dried with anhydrous magnesium sulfate, filtered with MgSO$_4$ and then removal of DCM. The extract is purified with the column by using DCM:MeOH=9.8:0.2. The product was a pale yellow liquid. Yield: 4.10 g; 70.0%.

Step 2. The 4-nitrophenyl chloroformate (3.35 g, 1.15 eq) was placed in two-neck bottle. Under vacuum for 1 hr, the three-way valve was diverted to nitrogen device and 60 mL DCM was added with a syringe. The weighted Step 1 Product 1 was dissolved with 10-15 mL DCM, injected into the reaction flask with a syringe, and then slowly added with triethylamine (4.5 mL, 2.3 eq). The reaction was carried out in an ice bath for about 1 hr and then back to room temperature for overnight. After completion of the reaction, the mixture was quenched by adding ddH$_2$O, and was extracted 2-3 times with DCM. The organic layer was collected, dried with anhydrous magnesium sulfate, filtered with MgSO$_4$ and then removal of DCM. The extract is purified with the column by using EtOAc:Hex:MeOH=1:1:0.2. The product was a pale yellow liquid. After purification yield: 48.6%.

Step 3. The weighted Step 2 Product 2 (3.5 g, 1.0 eq) was dissolved in 120 mL DCM, and then slowly added with Hydrazine hydrate (6.5 mL, 10.0 eq). The reaction was carried out at room temperature for about 24 hrs. The solution color turned from pale yellow to orange. After completion of the reaction, the mixture was quenched by adding ddH$_2$O, and extracted 2-3 times with DCM. The organic layer was collected, dried with anhydrous magnesium sulfate, filtered with MgSO$_4$ and then removal of DCM. The extract was purified with the column by using DCM:MeOH=9.5:0.5. In this step, the product was stuck in the column and the MeOH can be increased to 5% to elute the final product. The product was a pale yellow sticky solid. After purification yield: 19.0%.

Example 4 Preparation of HS—C$_5$-Linker-I-Amide

Step 1. The ethanolamine (1.28 g, 1.05 eq) and 6-Acetylthiohexanoic acid (3.81 g, 1.0 eq) were dissolved in 80 mL DCM, and EDC.HCl (4.98 g, 1.3 eq), hydroxysuccinimide (NHS)(2.30 g, 1.0 eq) and triethylamine (6.4 mL, 2.3 eq) were slowly added. The reaction was carried out at room temperature for at least 5 hrs and the reaction was followed by TLC. Subsequently, the mixture was quenched by adding ddH$_2$O, and was extracted 2-3 times with DCM. The organic layer was collected, dried with anhydrous magnesium sulfate, filtered with MgSO$_4$ and then removal of DCM. The extract is purified with the column by using DCM:MOH=9.8:0.2. The product was a pale yellow liquid. Yield: 3.85 g; 78.0%.

Step 2. The 4-nitrophenyl chloroformate (3.35 g, 1.15 eq) was placed in two-neck bottle. Under vacuum for 1 hr, the three-way valve was diverted to nitrogen device and 60 mL DCM was added with a syringe. The weighted Step 1 Product 1 was dissolved with 10-15 mL DCM, injected into the reaction flask with a syringe, and then slowly added with triethylamine (4.5 mL, 2.3 eq). The reaction was carried out in an ice bath for about 1 hr and then back to room temperature for overnight. After completion of the reaction, the mixture was quenched by adding ddH$_2$O, and was extracted 2-3 times with DCM. The organic layer was collected, dried with anhydrous magnesium sulfate, filtered with MgSO$_4$ and then removal of DCM. The extract is purified with the column by using EtOAc:Hex:MeOH=1:1:0.2. The product was a pale yellow liquid. After purification yield: 48.6%.

Step 3. The weighted Step 2 Product 2 (3.5 g, 1.0 eq) was dissolved in 120 mL DCM, and then slowly added with Hydrazine hydrate (6.5 mL, 10.0 eq). The reaction was carried out at room temperature for about 24 hrs. The solution color turned from pale yellow to orange. After completion of the reaction, the mixture was quenched by adding ddH$_2$O, and extracted 2-3 times with DCM. The organic layer was collected, dried with anhydrous magnesium sulfate, filtered with MgSO$_4$ and then removal of DCM. The extract was purified with the column by using DCM:MeOH=9.5:0.5. In this step, the product was stuck in the column and the MeOH can be increased to 5% to elute the final product. The product was a pale yellow sticky solid. After purification yield: 17.0%.

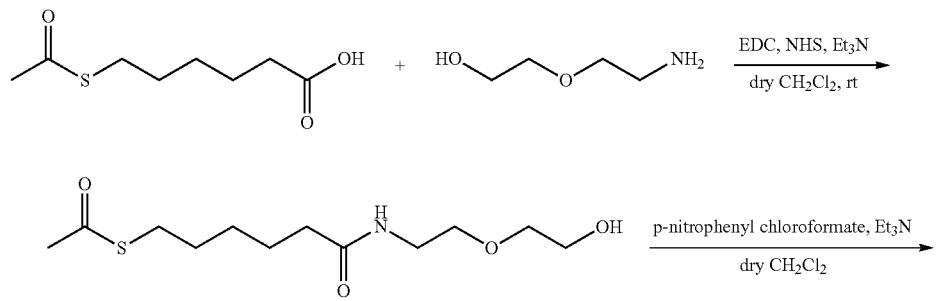

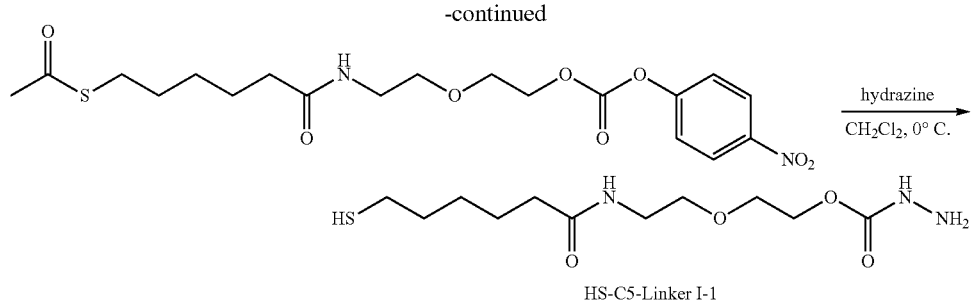

SH—C$_5$-Linker I-1 (SH—C$_5$-Linker-1-amide, m is 2): $^1$H (400 MHz) δ1.26-1.33 (2H, m), 1.43-1.55 (4H, m), 2.05 (2H, t), 2.22 (1H, s), 2.45 (2H, t), 3.15-3.19 (2H, m), 3.37 (2H, t), 3.54 (2H, t), 4.03-4.08 (4H, m), 7.85 (1H, t), 8.19 (1H, s); $^{13}$C (100 MHz) δ23.7, 24.7, 27.4, 33.1, 35.2, 38.4, 63.3, 68.6, 69.1, 158.3, 172.2. H-Mass (m/z): (M+Na)= 316.1336 filtered with MgSO$_4$ and then removal of DCM. The extract is purified with the column by using DCM:MeOH=9.8:0.2. The product was a pale yellow liquid. Yield: 3.88 g; 79.8%.

Step 2. The 4-nitrophenyl chloroformat (3.35 g, 1.15 eq) was placed in two-neck bottle. Under vacuum for 1 hr, the three-way valve was diverted to nitrogen device and 60 mL DCM was added with a syringe. The weighted Step 1 Product 1 was dissolved with 10-15 mL DCM, injected into the reaction flask with a syringe, and then slowly added with triethylamine (4.5 mL, 2.3 eq). The reaction was carried out in an ice bath for about 1 hr and then back to room temperature for overnight. After completion of the reaction, the mixture was quenched by adding ddH$_2$O, and was extracted 2-3 times with DCM. The organic layer was collected, dried with anhydrous magnesium sulfate, filtered with MgSO4 and then removal of DCM. The extract is purified with the column by using EA:Hex:MeOH=1:1:0.2. The product was a pale yellow liquid. After purification yield: 51.6%.

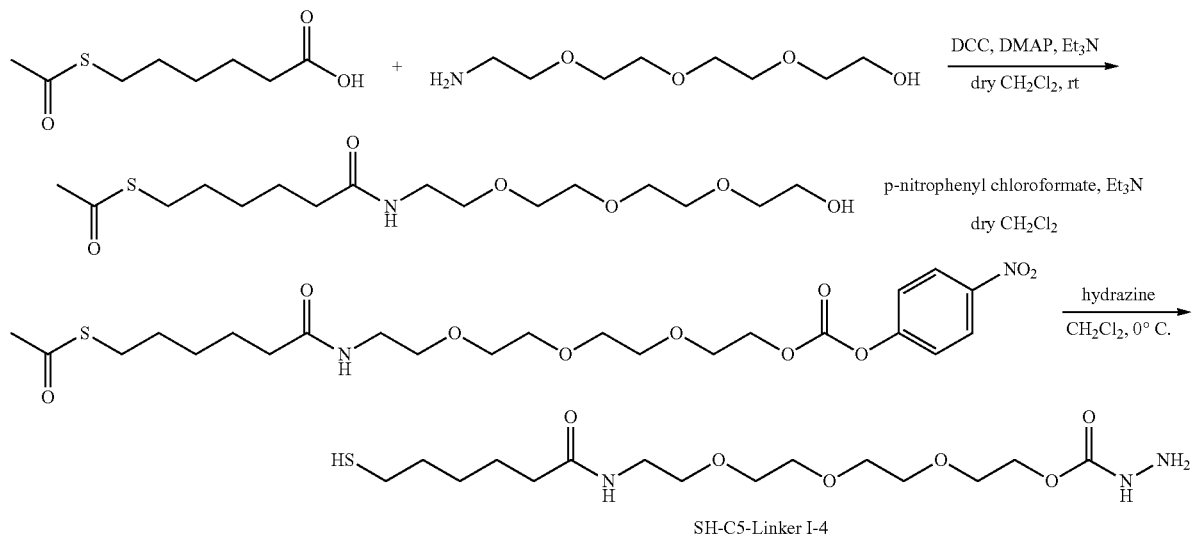

SH—C$_5$-Linker I-4 (SH—C$_5$-Linker-1-amide, m is 4): $^1$H (400 MHz) δ1.26-1.34 (2H, m), 1.43-1.56 (4H, m), 2.05 (2H, t), 2.22 (1H, t), 2.43-2.48 (2H, m), 3.16-3.20 (3H, m), 3.39 (2H, t), 3.48-3.50 (7H, m), 3.56 (2H, m), 4.03-4.08 (4H, m), 7.84 (1H, m), 8.20 (1H, s); $^{13}$C (100 MHz) δ23.7, 24.8, 27.4, 33.1, 35.2, 38.5, 63.4, 68.9, 69.2, 69.6, 69.8, 158.3, 172.2. H-Mass (m/z): (M+Na)=404.1843

Example 5 Preparation of SH—C$_5$-linker-I-C(O)O—

Step 1. The ethylene glycol (1.30 g, 1.05 eq) and 6-Acetylthiohexanoic acid (3.81 g, 1.0 eq) were dissolved in 80 mL DCM, and N,N'-Dicyclohexylcarbodiimide (DCC) (5.36 g, 1.3 eq), 4-(Dimethylamino)pyridine (DMAP) (0.24 g, 0.1 eq) and triethylamine (6.4 mL, 2.3 eq) were slowly added. The reaction was carried out at room temperature for at least 5 hrs and the reaction was followed by TLC. Subsequently, the mixture was quenched by adding ddH$_2$O, and was extracted 2-3 times with DCM. The organic layer was collected, dried with anhydrous magnesium sulfate, Step 3. The weighted Step 2 Product 2 (3.5 g, 1.0 eq) was dissolved in 120 mL DCM, and then slowly added with Hydrazine hydrate (6.5 mL, 10.0 eq). The reaction was carried out at room temperature for about 24 hrs. The solution color turned from pale yellow to orange. After completion of the reaction, the mixture was quenched by adding ddH$_2$O, and extracted 2-3 times with DCM. The organic layer was collected, dried with anhydrous magnesium sulfate, filtered with MgSO$_4$ and then removal of DCM. The extract was purified with the column by using DCM:MeOH=9.5:0.5. In this step, the product was stuck in the column and the MeOH can be increased to 5% to elute the final product. The product was a pale yellow sticky solid. After purification yield: 19.4%.

Example 6 Preparation of $NH_2$—$C_1$-Linker-I-Amide

Step 1. The ethanolamine (1.28 g, 1.05 eq) and Boc-glycine (3.50 g, 1.0 eq) were dissolved in 80 mL DCM, and EDC.HCl (4.98 g, 1.3 eq), hydroxysuccinimide (NHS)(2.30 g, 1.0 eq) and triethylamine (6.4 mL, 2.3 eq) were slowly added. The reaction was carried out at room temperature for at least 5 hrs and the reaction was followed by TLC. Subsequently, the mixture was quenched by adding $ddH_2O$, and was extracted 2-3 times with DCM. The organic layer was collected, dried with anhydrous magnesium sulfate, filtered with $MgSO_4$ and then removal of DCM. The extract is purified with the column by using DCM:MeOH=9.8:0.2. The product was a pale yellow liquid. Yield: 4.10 g; 81.5%.

Step 2. The 4-nitrophenyl chloroformat (3.35 g, 1.15 eq) was placed in two-neck bottle. Under vacuum for 1 hr, the three-way valve was diverted to nitrogen device and 60 mL DCM was added with a syringe. The weighted Step 1 Product 1 was dissolved with 10-15 mL DCM, injected into the reaction flask with a syringe, and then slowly added with triethylamine (4.5 mL, 2.3 eq). The reaction was carried out in an ice bath for about 1 hr and then back to room temperature for overnight. After completion of the reaction, the mixture was quenched by adding $ddH_2O$, and was extracted 2-3 times with DCM. The organic layer was collected, dried with anhydrous magnesium sulfate, filtered with $MgSO_4$ and then removal of DCM. The extract is purified with the column by using EtOAc:Hex:MeOH=1:1:0.2. The product was a pale yellow liquid. After purification yield: 51.6%.

Step 3. The weighted Step 2 Product 2 (3.5 g, 1.0 eq) was dissolved in 120 mL DCM, and then slowly added with Hydrazine hydrate (6.5 mL, 10.0 eq). The reaction was carried out at room temperature for about 24 hrs. The solution color turned from pale yellow to orange. After completion of the reaction, the mixture was quenched by adding $ddH_2O$, and extracted 2-3 times with DCM. The organic layer was collected, dried with anhydrous magnesium sulfate, filtered with $MgSO_4$ and then removal of DCM. The extract was purified with the column by using DCM:MeOH=9.5:0.5. In this step, the product was stuck in the column and the MeOH can be increased to 5% to elute the final product. The product was a pale yellow sticky solid. After purification yield: 17.9%.

Example 7 Preparation of $NH_2$—$C_1$-Linker-I-C(O)O—

Step 1. The ethylene glycol (1.30 g, 1.05 eq) and Boc-glycine (3.50 g, 1.0 eq) were dissolved in 80 mL DCM, and N,N'-Dicyclohexylcarbodiimide (DCC) (5.36 g, 1.3 eq), 4-(Dimethylamino)pyridine (DMAP) (0.24 g, 0.1 eq) and triethylamine (6.4 mL, 2.3 eq) were slowly added. The reaction was carried out at room temperature for at least 5 hrs and the reaction was followed by TLC. Subsequently, the mixture was quenched by adding $ddH_2O$, and was extracted 2-3 times with DCM. The organic layer was collected, dried with anhydrous magnesium sulfate, filtered with $MgSO_4$ and then removal of DCM. The extract is purified with the column by using DCM:MeOH=9.8:0.2. The product was a pale yellow liquid. Yield: 3.60 g; 78.0%.

Step 2. The 4-nitrophenyl chloroformate (3.35 g, 1.15 eq) was placed in two-neck bottle. Under vacuum for 1 hr, the three-way valve was diverted to nitrogen device and 60 mL DCM was added with a syringe. The weighted Step 1 Product 1 was dissolved with 10-15 mL DCM, injected into the reaction flask with a syringe, and then slowly added with triethylamine (4.5 mL, 2.3 eq). The reaction was carried out in an ice bath for about 1 hr and then back to room temperature for overnight. After completion of the reaction, the mixture was quenched by adding $ddH_2O$, and was extracted 2-3 times with DCM. The organic layer was collected, dried with anhydrous magnesium sulfate, filtered with $MgSO_4$ and then removal of DCM. The extract is purified with the column by using EA:Hex:MeOH=1:1:0.2. The product was a pale yellow liquid. After purification yield: 49.7%.

Step 3. The weighted Step 2 Product 2 (3.5 g, 1.0 eq) was dissolved in 120 mL DCM, and then slowly added with Hydrazine hydrate (6.5 mL, 10.0 eq). The reaction was carried out at room temperature for about 24 hrs. The solution color turned from pale yellow to orange. After completion of the reaction, the mixture was quenched by adding $ddH_2O$, and extracted 2-3 times with DCM. The organic layer was collected, dried with anhydrous magnesium sulfate, filtered with $MgSO_4$ and then removal of DCM. The extract was purified with the column by using DCM:MeOH=9.5:0.5. In this step, the product was stuck in the column and the MeOH can be increased to 5% to elute the final product. The product was a pale yellow sticky solid. After purification yield: 20.0%.

Example 8 Preparation of Linker II-amide

Step 1. The glycine (2.36 g, 1.05 eq) and Lipoic acid (6.19 g, 1.0 eq) were dissolved in 80 mL DCM, and EDC.HCl (7.47 g, 1.3 eq), hydroxysuccinimide (NHS) (3.45 g, 1.0 eq) and triethylamine (9.6 mL, 2.3 eq) were slowly added. The reaction was carried out at room temperature for at least 5 hrs and the reaction was followed by TLC. Subsequently, the mixture was quenched by adding $ddH_2O$, and was extracted 2-3 times with DCM. The organic layer was collected, dried with anhydrous magnesium sulfate, filtered with $MgSO_4$ and then removal of DCM. The extract is purified with the column by using DCM:MeOH=9.5:0.5. The product was a pale yellow liquid. Yield: 70.0%.

Step 2. The Step 1 product (5.26 g, 1.0 eq) and ethanolamine (1.28 g, 1.05 eq) were dissolved in 80 mL DCM, and EDC.HCl (4.98 g, 1.3 eq), hydroxysuccinimide (NHS) (2.30 g, 1.0 eq) and triethylamine (6.4 mL, 2.3 eq) were slowly added. The reaction was carried out at room temperature for at least 5 hrs and the reaction was followed by TLC. Subsequently, the mixture was quenched by adding $ddH_2O$, and was extracted 2-3 times with DCM. The organic layer was collected, dried with anhydrous magnesium sulfate, filtered with $MgSO_4$ and then removal of DCM. The extract is purified with the column by using DCM:MeOH=9.8:0.2. The product was a pale yellow liquid. Yield: 81.0%.

Step 3. The 4-nitrophenyl chloroformat (3.35 g, 1.15 eq) was placed in two-neck bottle. Under vacuum for 1 hr, the three-way valve was diverted to nitrogen device and 60 mL DCM was added with a syringe. The weighted Step 1 Product 1 was dissolved with 10-15 mL DCM, injected into the reaction flask with a syringe, and then slowly added with triethylamine (4.5 mL, 2.3 eq). The reaction was carried out in an ice bath for about 1 hr and then back to room temperature for overnight. After completion of the reaction, the mixture was quenched by adding ddH$_2$O, and was extracted 2-3 times with DCM. The organic layer was collected, dried with anhydrous magnesium sulfate, filtered with MgSO$_4$ and then removal of DCM. The extract is purified with the column by using EtOAc:Hex:MeOH=1:2:0.2. The product was a pale yellow liquid. After purification yield: 51.6%.

Step 4. The weighted Step 2 Product 2 (3.5 g, 1.0 eq) was dissolved in 120 mL DCM, and then slowly added with Hydrazine hydrate (6.5 mL, 10.0 eq). The reaction was carried out at room temperature for about 24 hrs. The solution color turned from pale yellow to orange. After completion of the reaction, the mixture was quenched by adding ddH$_2$O, and extracted 2-3 times with DCM. The organic layer was collected, dried with anhydrous magnesium sulfate, filtered with MgSO$_4$ and then removal of DCM. The extract was purified with the column by using DCM:MeOH=9.5:0.5. In this step, the product was stuck in the column and the MeOH can be increased to 5% to elute the final product. The product was a pale yellow sticky solid. After purification yield: 30.0%.

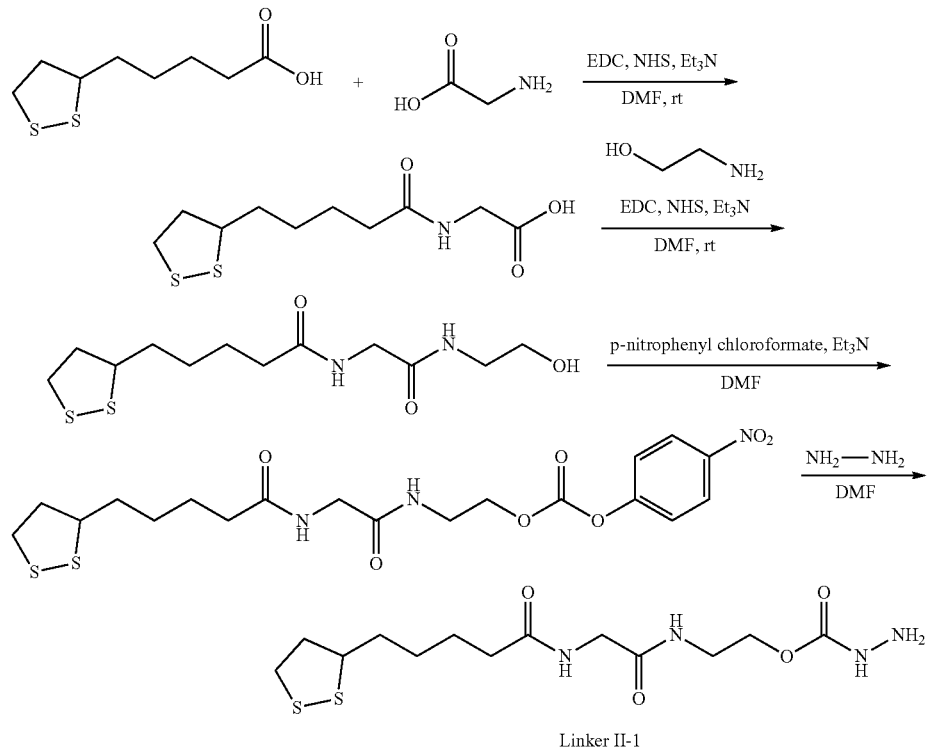

Linker II-1 (Linker II-amide, z=1). $^1$H (400 MHz) δ1.32-1.39 (2H, m), 1.46-1.57 (2H, m), 1.63-1.69 (1H, m), 1.83-1.91 (1H, m), 2.08 (1H, s), 2.13 (2H, t), 2.36-2.46 (1H, m), 3.07-3.19 (2H, m), 3.22-3.28 (2H, m), 3.62-3.65 (3H, m), 3.95 (3H, t), 7.01 (1H, s), 7.91 (1H, t), 8.01 (1H, t), 8.14 (1H, s). $^{13}$C (100 MHz) δ25.2, 28.8, 34.6, 35.4, 38.6, 38.7, 39.5, 42.4, 56.60, 62.85, 135.63, 169.72, 172.83 ppm. H-Mass (m/z): (M+Na)=387.1102

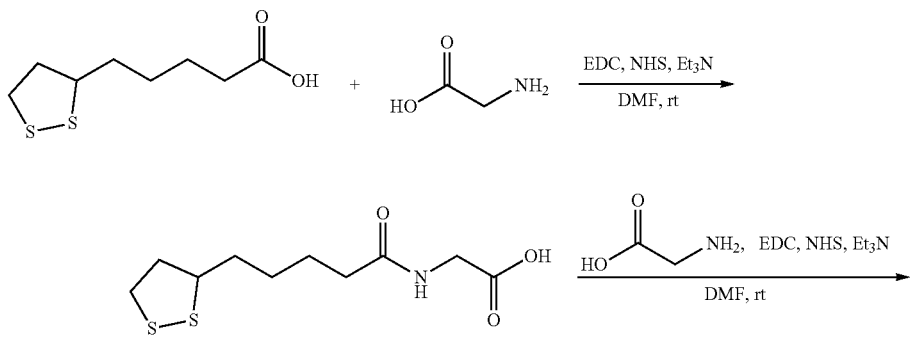

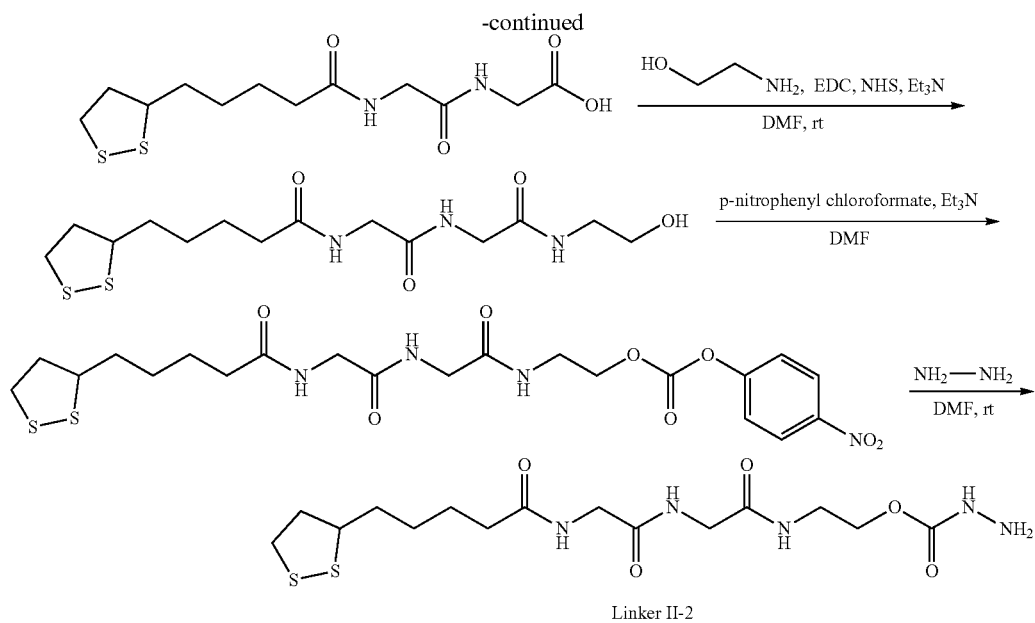
Linker II-2
Linker II-2 (Linker II-amide, z=2). $^1$H (300 MHz) δ1.32-1.39 (2H, m), 1.47-1.57 (3H, m), 1.61-1.73 (1H, m), 1.81-1.92 (1H, m), 2.14 (2H, t), 2.35-2.46 (2H, m), 3.09-3.21 (3H, m), 3.23-3.31 (3H, m), 3.65-3.71 (4H, m), 3.97 (2H, t), 7.78 (1H, t), 7.89 (1H, t), 8.12 (2H, t). $^{13}$C (100 MHz) δ25.3, 28.8, 34.6, 35.4, 38.6, 38.7, 39.5, 42.4, 42.6, 56.6, 60.2, 62.8, 169.4, 169.9, 173.1 ppm. H-Mass (m/z): (M+Na)=444.1345
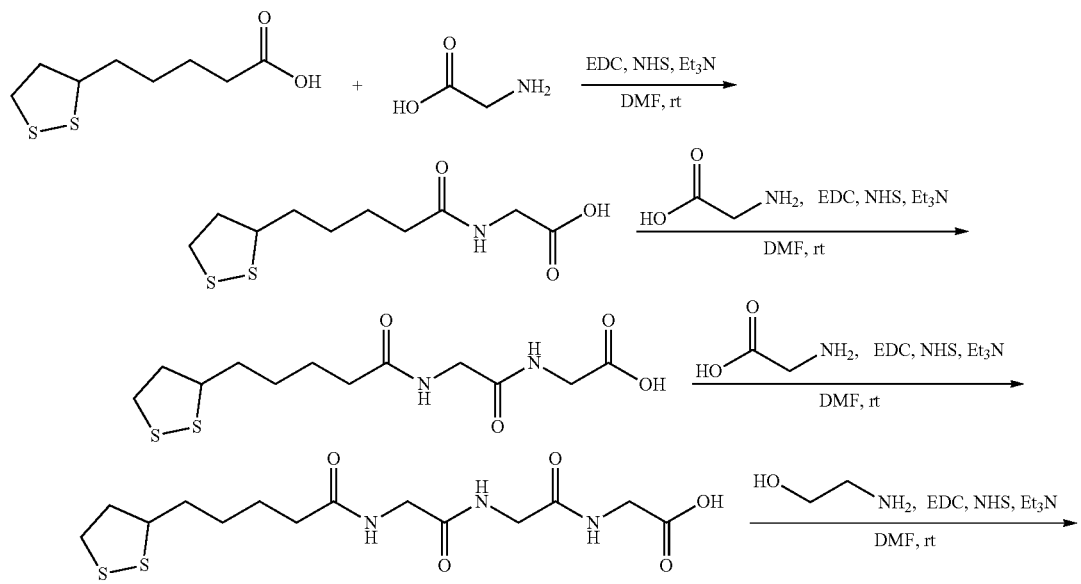
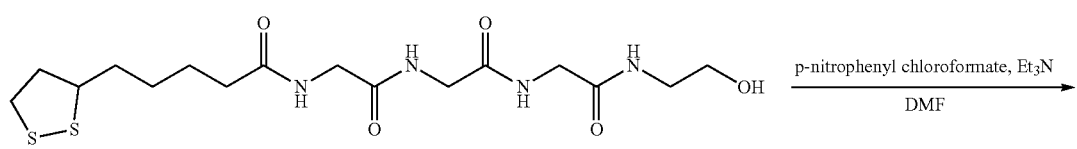

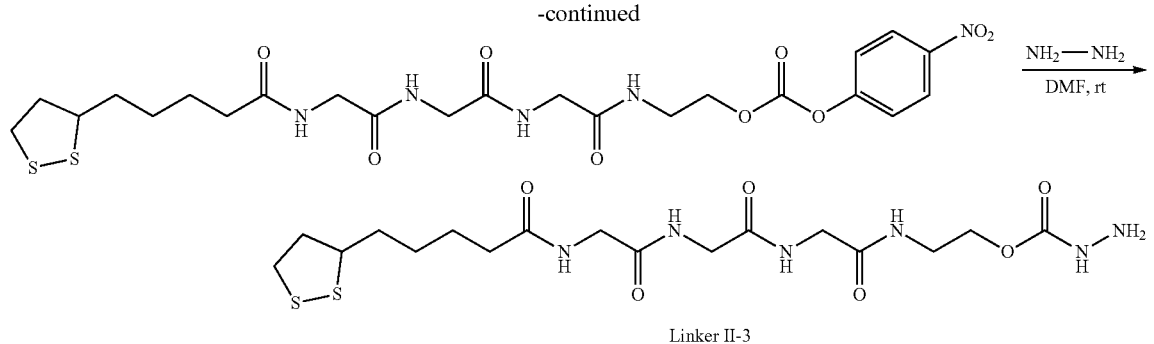
Linker II-3 (Linker II-amide, z=3). $^1$H (300 MHz) δ1.23 (1H, s), 1.32-1.40 (2H, m), 1.46-1.57 (4H, m), 1.63-1.70 (1H, m), 1.80-1.92 (2H, t), 1.96 (1H, s), 2.04 (1H, s), 2.14 (3H, t), 3.07-3.19 (3H, m), 3.58-3.66 (3H, m), 3.72 (3H, t), 3.96 (1H, t), 4.05 (1H, s), 7.86 (1H, s), 8.10 (3H, s). $^{13}$C (100 MHz) δ25.3, 28.8, 34.6, 35.4, 38.6, 39.5, 39.7, 40.5, 42.4, 42.6, 56.6, 60.2, 62.8, 169.4, 169.6, 170.1, 173.1 ppm. H-Mass (m/z): (M+Na)=501.1606
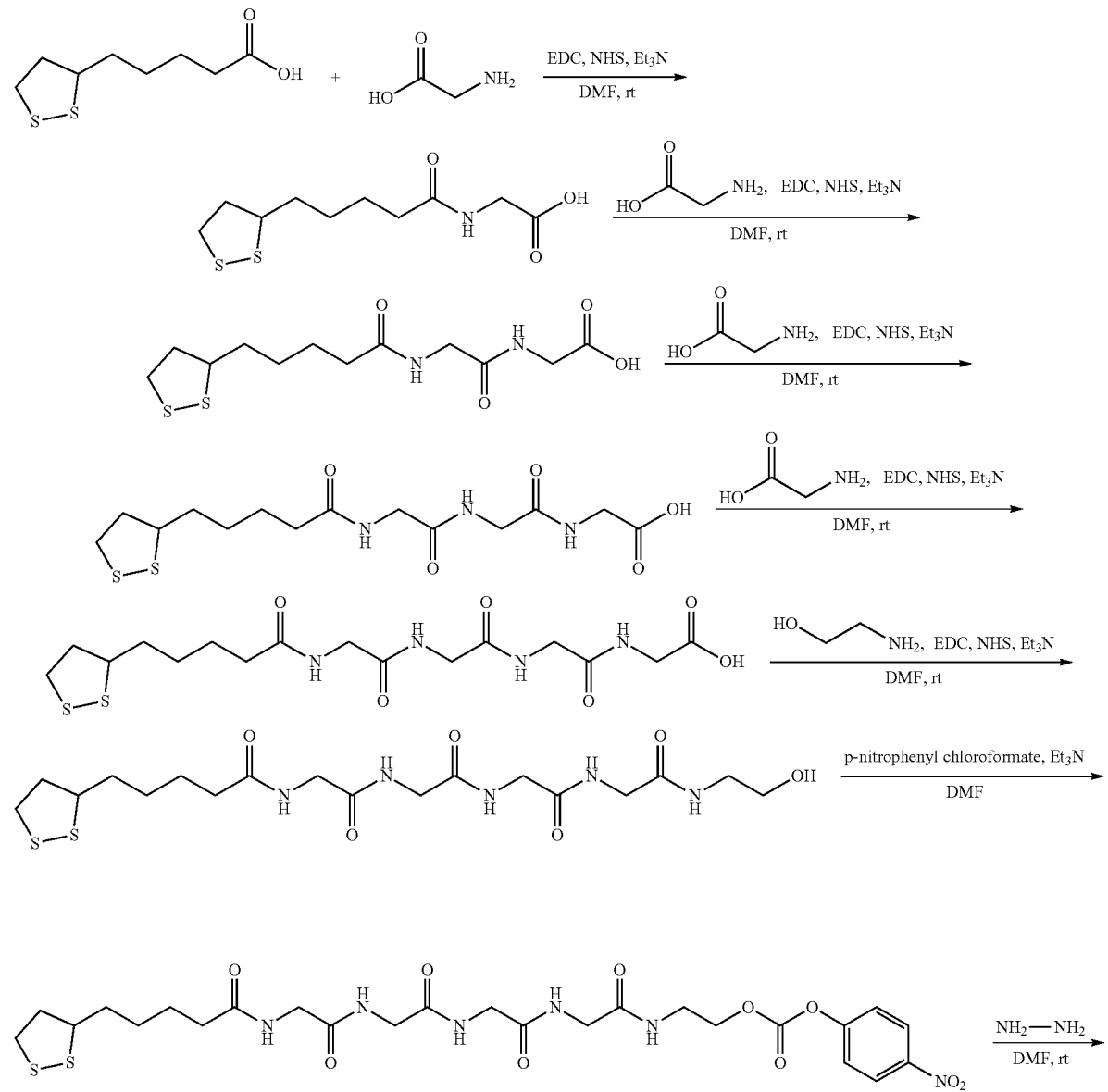

-continued

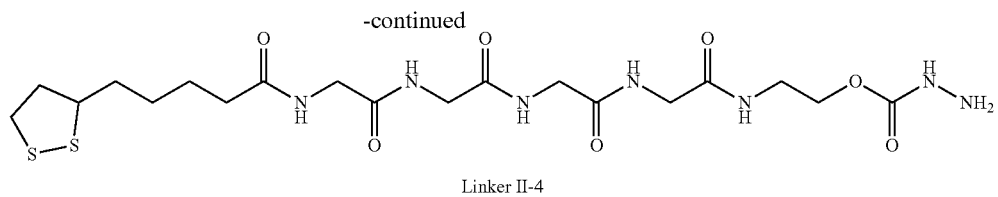

Linker II-4

Linker II-4 (Linker II-amide, z=4). $^1$H (300 MHz) δ1.26 (3H, s), 1.35-1.42 (2H, m), 1.47-1.70 (4H, m), 1.82-1.94 (2H, m), 2.03-2.20 (8H, m), 2.26-2.33 (2H, m), 3.66-3.81 (7H, m), 3.95-4.01 (1H, m), 7.86-7.94 (1H, m), 8.80-8.22 (3H, m). $^{13}$C (100 MHz) δ25.3, 28.8, 29.4, 31.2, 34.6, 35.4, 38.5, 38.6, 42.4, 42.6, 56.6, 66.0, 125.8, 128.7, 129.4, 169.4, 169.8, 170.0, 173.1 ppm. H-Mass (m/z): (M+Na)=558.1768

Example 9 Preparation of Linker II-C(O)O—

Step 1. The glycolic acid (2.40 g, 1.05 eq) and Lipoic acid (6.19 g, 1.0 eq) were dissolved in 80 mL DCM, and N,N'-Dicyclohexylcarbodiimide (DCC) (8.05 g, 1.3 eq), 4-(Dimethylamino)pyridine (DMAP) (0.37 g, 0.1 eq) and triethylamine (9.6 mL, 2.3 eq) were slowly added. The reaction was carried out at room temperature for at least 5 hrs and the reaction was followed by TLC. Subsequently, the mixture was quenched by adding ddH$_2$O, and was extracted 2-3 times with DCM. The organic layer was collected, dried with anhydrous magnesium sulfate, filtered with MgSO$_4$ and then removal of DCM. The extract is purified with the column by using DCM:MeOH=9.5:0.5. The product was a pale yellow liquid. Yield: 85%.

Step 2. The Step 1 product (5.26 g, 1.0 eq) and ethanolamine (1.28 g, 1.05 eq) were dissolved in 80 mL DCM, and EDC.HCl (4.98 g, 1.3 eq), hydroxysuccinimide (NHS) (2.30 g, 1.0 eq) and triethylamine (6.4 mL, 2.3 eq) were slowly added. The reaction was carried out at room temperature for at least 5 hrs and the reaction was followed by TLC. Subsequently, the mixture was quenched by adding ddH$_2$O, and was extracted 2-3 times with DCM. The organic layer was collected, dried with anhydrous magnesium sulfate, filtered with MgSO$_4$ and then removal of DCM. The extract is purified with the column by using DCM:MeOH=9.8:0.2. The product was a pale yellow liquid. Yield: 80.5%.

Step 3. The 4-nitrophenyl chloroformate (3.35 g, 1.15 eq) was placed in two-neck bottle. Under vacuum for 1 hr, the three-way valve was diverted to nitrogen device and 60 mL DCM was added with a syringe. The weighted Step 1 Product 1 was dissolved with 10-15 mL DCM, injected into the reaction flask with a syringe, and then slowly added with triethylamine (4.5 mL, 2.3 eq). The reaction was carried out in an ice bath for about 1 hr and then back to room temperature for overnight. After completion of the reaction, the mixture was quenched by adding ddH$_2$O, and was extracted 2-3 times with DCM. The organic layer was collected, dried with anhydrous magnesium sulfate, filtered with MgSO$_4$ and then removal of DCM. The extract is purified with the column by using EtOAc:Hex:MeOH=1:2: 0.2. The product was a pale yellow liquid. After purification yield: 47.8%.

Step 4. The weighted Step 2 Product 2 (3.5 g, 1.0 eq) was dissolved in 120 mL DCM, and then slowly added with Hydrazine hydrate (6.5 mL, 10.0 eq). The reaction was carried out at room temperature for about 24 hrs. The solution color turned from pale yellow to orange. After completion of the reaction, the mixture was quenched by adding ddH$_2$O, and extracted 2-3 times with DCM. The organic layer was collected, dried with anhydrous magnesium sulfate, filtered with MgSO$_4$ and then removal of DCM. The extract was purified with the column by using DCM:MeOH=9.5:0.5. In this step, the product was stuck in the column and the MeOH can be increased to 5% to elute the final product. The product was a pale yellow sticky solid. After purification yield: 19.3%.

Example 10 Preparation of Linker SH—C$_5$-Linker-II-Amide

Step 1. The 6-Acetylthiohexanoic acid (5.71 g, 1.0 eq) and glycine (2.36 g, 1.05 eq) were dissolved in 80 mL DCM, and EDC.HCl (7.47 g, 1.3 eq), hydroxysuccinimide (NETS) (3.45 g, 1.0 eq) and triethylamine (9.6 mL, 2.3 eq) were slowly added. The reaction was carried out at room temperature for at least 5 hrs and the reaction was followed by TLC. Subsequently, the mixture was quenched by adding ddH$_2$O, and was extracted 2-3 times with DCM. The organic layer was collected, dried with anhydrous magnesium sulfate, filtered with MgSO$_4$ and then removal of DCM. The extract is purified with the column by using DCM:MeOH=9.5:0.5. The product was a pale yellow liquid. Yield: 68.8%.

Step 2. The Step 1 product (5.26 g, 1.0 eq) and ethanolamine (1.28 g, 1.05 eq) were dissolved in 80 mL DCM, and EDC.HCl (4.98 g, 1.3 eq), hydroxysuccinimide (NHS) (2.30 g, 1.0 eq) and triethylamine (6.4 mL, 2.3 eq) were slowly added. The reaction was carried out at room temperature for at least 5 hrs and the reaction was followed by TLC. Subsequently, the mixture was quenched by adding ddH$_2$O, and was extracted 2-3 times with DCM. The organic layer was collected, dried with anhydrous magnesium sulfate, filtered with MgSO$_4$ and then removal of DCM. The extract is purified with the column by using DCM:MeOH=9.8:0.2. The product was a pale yellow liquid. Yield: 80.5%.

Step 3. The 4-nitrophenyl chloroformat (3.35 g, 1.15 eq) was placed in two-neck bottle. Under vacuum for 1 hr, the three-way valve was diverted to nitrogen device and 60 mL DCM was added with a syringe. The weighted Step 1 Product 1 was dissolved with 10-15 mL DCM, injected into the reaction flask with a syringe, and then slowly added with triethylamine (4.5 mL, 2.3 eq). The reaction was carried out in an ice bath for about 1 hr and then back to room temperature for overnight. After completion of the reaction, the mixture was quenched by adding ddH$_2$O, and was extracted 2-3 times with DCM. The organic layer was collected, dried with anhydrous magnesium sulfate, filtered with MgSO$_4$ and then removal of DCM. The extract is purified with the column by using EtOAc:Hex:MeOH=1:2: 0.2. The product was a pale yellow liquid. After purification yield: 50.6%.

Step 4. The weighted Step 2 Product 2 (3.5 g, 1.0 eq) was dissolved in 120 mL DCM, and then slowly added with Hydrazine hydrate (6.5 mL, 10.0 eq). The reaction was carried out at room temperature for about 24 hrs. The solution color turned from pale yellow to orange. After completion of the reaction, the mixture was quenched by adding ddH$_2$O, and extracted 2-3 times with DCM. The organic layer was collected, dried with anhydrous magnesium sulfate, filtered with MgSO$_4$ and then removal of DCM. The extract was purified with the column by using DCM:MeOH=9.5:0.5. In this step, the product was stuck in the column and the MeOH can be increased to 5% to elute the final product. The product was a pale yellow sticky solid. After purification yield: 18.3%.

Example 11 Preparation of LinkerSH-C$_5$-linker-II-C(O)O—

Step 1. The 6-Acetylthiohexanoic acid (5.71 g, 1.0 eq) and glycolic acid (2.40 g, 1.05 eq) were dissolved in 80 mL DCM, and N,N'-Dicyclohexylcarbodiimide (DCC) (8.05 g, 1.3 eq), 4-(Dimethylamino)pyridine (DMAP) (0.37 g, 0.1 eq) and triethylamine (9.6 mL, 2.3 eq) were slowly added. The reaction was carried out at room temperature for at least 5 hrs and the reaction was followed by TLC. Subsequently, the mixture was quenched by adding ddH$_2$O, and was extracted 2-3 times with DCM. The organic layer was collected, dried with anhydrous magnesium sulfate, filtered with MgSO$_4$ and then removal of DCM. The extract is purified with the column by using DCM:MeOH=9.5:0.5. The product was a pale yellow liquid. Yield: 78%.

Step 2. The Step 1 product (5.26 g, 1.0 eq) and ethanolamine (1.28 g, 1.05 eq) were dissolved in 80 mL DCM, and EDC.HCl (4.98 g, 1.3 eq), hydroxysuccinimide (NHS) (2.30 g, 1.0 eq) and triethylamine (6.4 mL, 2.3 eq) were slowly added. The reaction was carried out at room temperature for at least 5 hrs and the reaction was followed by TLC. Subsequently, the mixture was quenched by adding ddH$_2$O, and was extracted 2-3 times with DCM. The organic layer was collected, dried with anhydrous magnesium sulfate, filtered with MgSO$_4$ and then removal of DCM. The extract is purified with the column by using DCM:MeOH=9.8:0.2. The product was a pale yellow liquid. Yield: 80.5%.

Step 3. The 4-nitrophenyl chloroformat (3.35 g, 1.15 eq) was placed in two-neck bottle. Under vacuum for 1 hr, the three-way valve was diverted to nitrogen device and 60 mL DCM was added with a syringe. The weighted Step 1 Product 1 was dissolved with 10-15 mL DCM, injected into the reaction flask with a syringe, and then slowly added with triethylamine (4.5 mL, 2.3 eq). The reaction was carried out in an ice bath for about 1 hr and then back to room temperature for overnight. After completion of the reaction, the mixture was quenched by adding ddH$_2$O, and was extracted 2-3 times with DCM. The organic layer was collected, dried with anhydrous magnesium sulfate, filtered with MgSO$_4$ and then removal of DCM. The extract is purified with the column by using EtOAc:Hex:MeOH=1:2:0.2. The product was a pale yellow liquid. After purification yield: 51.6%.

Step 4. The weighted Step 2 Product 2 (3.5 g, 1.0 eq) was dissolved in 120 mL DCM, and then slowly added with Hydrazine hydrate (6.5 mL, 10.0 eq). The reaction was carried out at room temperature for about 24 hrs. The solution color turned from pale yellow to orange. After completion of the reaction, the mixture was quenched by adding ddH$_2$O, and extracted 2-3 times with DCM. The organic layer was collected, dried with anhydrous magnesium sulfate, filtered with MgSO$_4$ and then removal of DCM. The extract was purified with the column by using DCM:MeOH=9.5:0.5. In this step, the product was stuck in the column and the MeOH can be increased to 5% to elute the final product. The product was a pale yellow sticky solid. After purification yield: 19.0%.

Example 12 Preparation of LinkerNH2-C$_1$-Linker-II-Amide

Step 1. The Boc-glycine (5.26 g, 1.0 eq) and glycine (2.36 g, 1.05 eq) were dissolved in 80 mL DCM, and EDC.HCl (7.47 g, 1.3 eq), hydroxysuccinimide (NHS) (3.45 g, 1.0 eq) and triethylamine (9.6 mL, 2.3 eq) were slowly added. The reaction was carried out at room temperature for at least 5 hrs and the reaction was followed by TLC. Subsequently, the mixture was quenched by adding ddH$_2$O, and was extracted 2-3 times with DCM. The organic layer was collected, dried with anhydrous magnesium sulfate, filtered with MgSO$_4$ and then removal of DCM. The extract is purified with the column by using DCM:MeOH=9.5:0.5. The product was a pale yellow liquid. Yield: 70%.

Step 2. The Step 1 product (5.26 g, 1.0 eq) and ethanolamine (1.28 g, 1.05 eq) were dissolved in 80 mL DCM, and EDC.HCl (4.98 g, 1.3 eq), hydroxysuccinimide (NHS) (2.30 g, 1.0 eq) and triethylamine (6.4 mL, 2.3 eq) were slowly added. The reaction was carried out at room temperature for at least 5 hrs and the reaction was followed by TLC. Subsequently, the mixture was quenched by adding ddH$_2$O, and was extracted 2-3 times with DCM. The organic layer was collected, dried with anhydrous magnesium sulfate, filtered with MgSO$_4$ and then removal of DCM. The extract is purified with the column by using DCM:MeOH=9.8:0.2. The product was a pale yellow liquid. Yield: 77.8%.

Step 3. The 4-nitrophenyl chloroformat (3.35 g, 1.15 eq) was placed in two-neck bottle. Under vacuum for 1 hr, the three-way valve was diverted to nitrogen device and 60 mL DCM was added with a syringe. The weighted Step 1 Product 1 was dissolved with 10-15 mL DCM, injected into the reaction flask with a syringe, and then slowly added with triethylamine (4.5 mL, 2.3 eq). The reaction was carried out in an ice bath for about 1 hr and then back to room temperature for overnight. After completion of the reaction, the mixture was quenched by adding ddH$_2$O, and was extracted 2-3 times with DCM. The organic layer was collected, dried with anhydrous magnesium sulfate, filtered with MgSO$_4$ and then removal of DCM. The extract is purified with the column by using EtOAc:Hex:MeOH=1:2:0.2. The product was a pale yellow liquid. After purification yield: 51.6%.

Step 4. The weighted Step 2 Product 2 (3.5 g, 1.0 eq) was dissolved in 120 mL DCM, and then slowly added with Hydrazine hydrate (6.5 mL, 10.0 eq). The reaction was carried out at room temperature for about 24 hrs. The solution color turned from pale yellow to orange. After completion of the reaction, the mixture was quenched by adding ddH$_2$O, and extracted 2-3 times with DCM. The organic layer was collected, dried with anhydrous magnesium sulfate, filtered with MgSO$_4$ and then removal of DCM. The extract was purified with the column by using DCM:MeOH=9.5:0.5. In this step, the product was stuck in the column and the MeOH can be increased to 5% to elute the final product. The product was a pale yellow sticky solid. After purification yield: 18.8%.

Example 13 Preparation of NH$_2$—C$_1$-Linker-II-C(O)O—

Step 1. The Boc-glycine (5.26 g, 1.0 eq) and glycolic acid (2.40 g, 1.05 eq) were dissolved in 80 mL DCM, and N,N'-Dicyclohexylcarbodiimide (DCC) (8.05 g, 1.3 eq), 4-(Dimethylamino)pyridine (DMAP) (0.37 g, 0.1 eq) and triethylamine (9.6 mL, 2.3 eq) were slowly added. The reaction was carried out at room temperature for at least 5 hrs and the reaction was followed by TLC. Subsequently, the mixture was quenched by adding ddH$_2$O, and was extracted 2-3 times with DCM. The organic layer was collected, dried with anhydrous magnesium sulfate, filtered with MgSO$_4$ and then removal of DCM. The extract is purified with the column by using DCM:MOH=9.5:0.5. The product was a pale yellow liquid. Yield: 82.0%.

Step 2. The Step 1 product (5.26 g, 1.0 eq) and ethanolamine (1.28 g, 1.05 eq) were dissolved in 80 mL DCM, and EDC.HCl (4.98 g, 1.3 eq), hydroxysuccinimide (NHS) (2.30 g, 1.0 eq) and triethylamine (6.4 mL, 2.3 eq) were slowly added. The reaction was carried out at room temperature for at least 5 hrs and the reaction was followed by TLC. Subsequently, the mixture was quenched by adding ddH$_2$O, and was extracted 2-3 times with DCM. The organic layer was collected, dried with anhydrous magnesium sulfate, filtered with MgSO$_4$ and then removal of DCM. The extract is purified with the column by using DCM:MeOH=9.8:0.2. The product was a pale yellow liquid. Yield: 78.5%.

Step 3. The 4-nitrophenyl chloroformate (3.35 g, 1.15 eq) was placed in two-neck bottle. Under vacuum for 1 hr, the three-way valve was diverted to nitrogen device and 60 mL DCM was added with a syringe. The weighted Step 1 Product 1 was dissolved with 10-15 mL DCM, injected into the reaction flask with a syringe, and then slowly added with triethylamine (4.5 mL, 2.3 eq). The reaction was carried out in an ice bath for about 1 hr and then back to room temperature for overnight. After completion of the reaction, the mixture was quenched by adding ddH$_2$O, and was extracted 2-3 times with DCM. The organic layer was collected, dried with anhydrous magnesium sulfate, filtered with MgSO$_4$ and then removal of DCM. The extract is purified with the column by using EtOAc:Hex:MeOH=1:2:0.2. The product was a pale yellow liquid. After purification yield: 51.0%.

Step 4. The weighted Step 2 Product (3.5 g, 1.0 eq) was dissolved in 120 mL DCM, and then slowly added with Hydrazine hydrate (6.5 mL, 10.0 eq). The reaction was carried out at room temperature for about 24 hrs. The solution color turned from pale yellow to orange. After completion of the reaction, the mixture was quenched by adding ddH$_2$O, and extracted 2-3 times with DCM. The organic layer was collected, dried with anhydrous magnesium sulfate, filtered with MgSO$_4$ and then removal of DCM. The extract was purified with the column by using DCM:MeOH=9.5:0.5. In this step, the product was stuck in the column and the MeOH can be increased to 5% to elute the final product. The product was a pale yellow sticky solid. After purification yield: 19.5%.

Example 14 Preparation of Linker IV-Amide

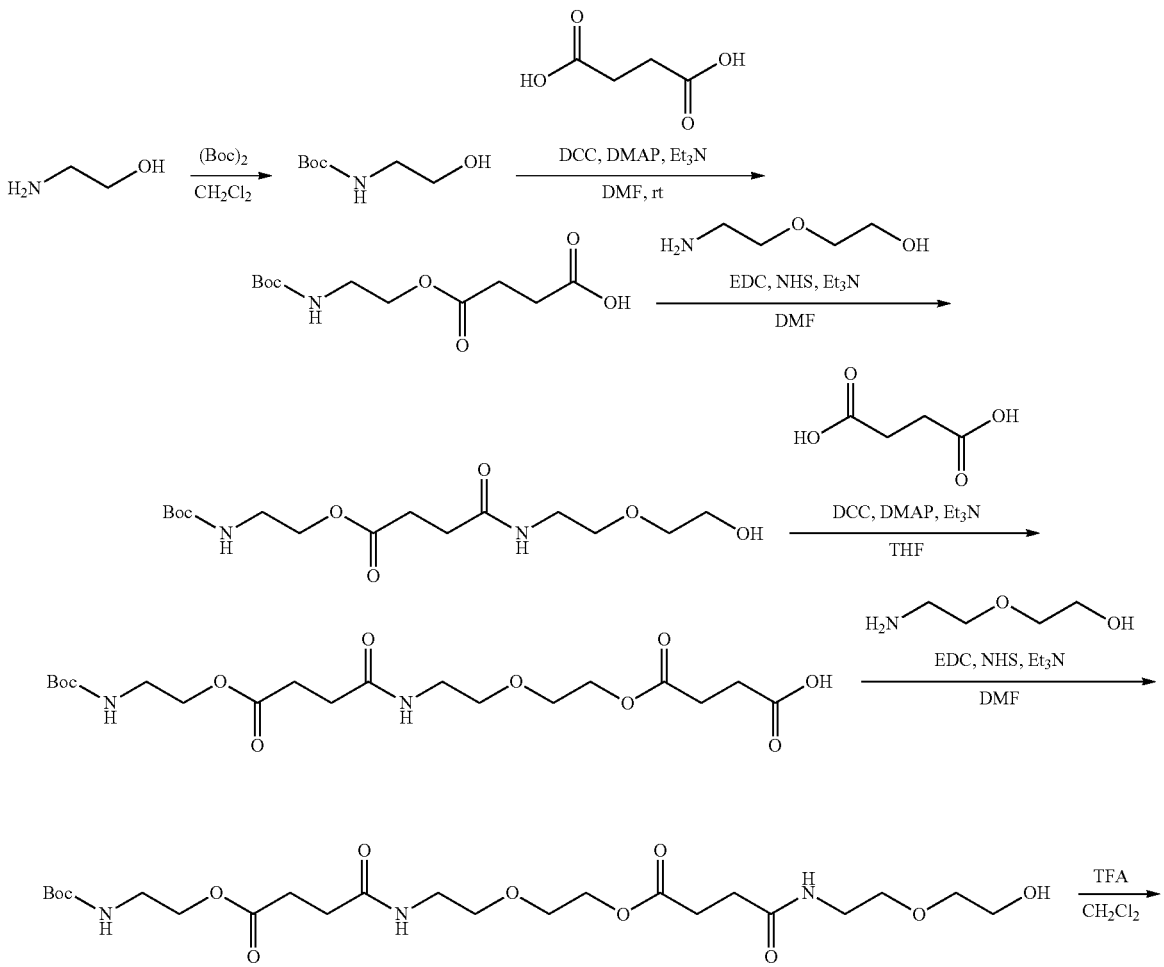

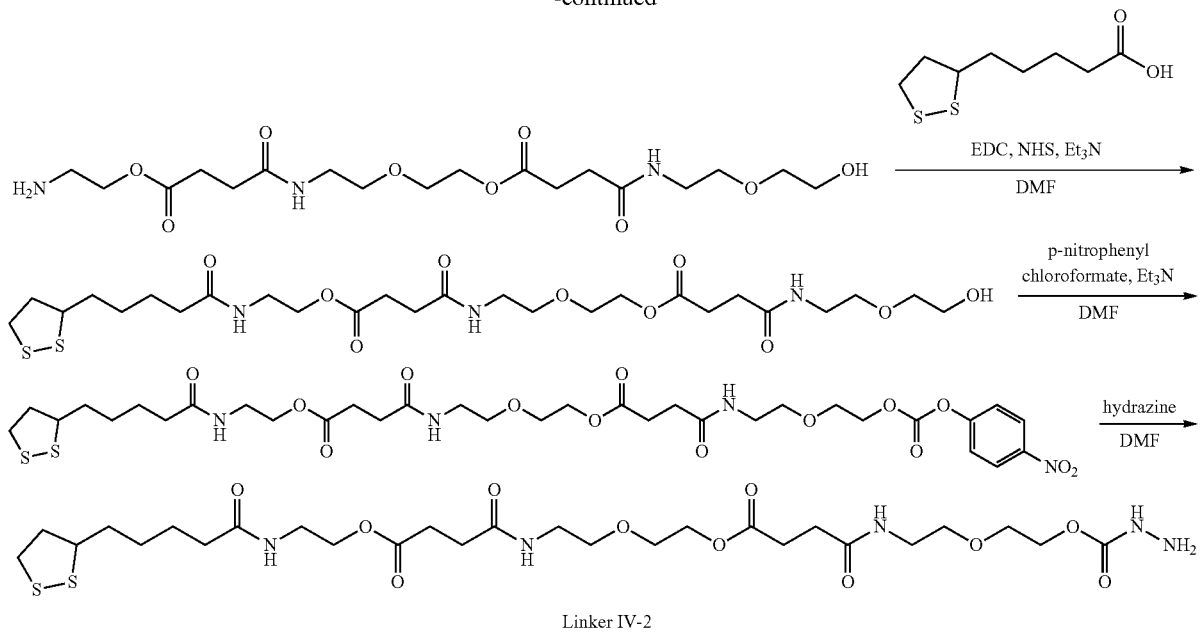

Linker IV-2

Step 1. The ethanolamine (1.92 g, 1.05 eq) and Lipoic acid (6.19 g, 1.0 eq) were dissolved in 80 mL DCM, and EDC.HCl (7.47 g, 1.3 eq), hydroxysuccinimide (NETS) (3.45 g, 1.0 eq) and triethylamine (9.6 mL, 2.3 eq) were slowly added. The reaction was carried out at room temperature for at least 5 hrs and the reaction was followed by TLC. Subsequently, the mixture was quenched by adding ddH$_2$O, and was extracted 2-3 times with DCM. The organic layer was collected, dried with anhydrous magnesium sulfate, filtered with MgSO$_4$ and then removal of DCM. The extract is purified with the column by using DCM:MeOH=9.8:0.2. The product was a pale yellow liquid. Yield: 66.0%.

Step 2. The Step 1 product (4.98 g, 1.0 eq) and succinic acid (2.48 g, 1.05 eq) were dissolved in 80 mL DCM, and N,N'-Dicyclohexylcarbodiimide (DCC) (5.36 g, 1.3 eq), 4-(Dimethylamino)pyridine (DMAP) (0.24 g, 0.1 eq) and triethylamine (6.4 mL, 2.3 eq) were slowly added. The reaction was carried out at room temperature for at least 5 hrs and the reaction was followed by TLC. Subsequently, the mixture was quenched by adding ddH$_2$O, and was extracted 2-3 times with DCM. The organic layer was collected, dried with anhydrous magnesium sulfate, filtered with MgSO$_4$ and then removal of DCM. The extract is purified with the column by using DCM:MeOH=9.5:0.5. The product was a pale yellow liquid. Yield: 80.7%.

Step 3. The Step 2 product (3.49 g, 1.0 eq) and 2-[2-(2-Aminoethoxy)ethoxy]ethanol (1.57 g, 1.05 eq) were dissolved in 80 mL DCM, and EDC.HCl (2.49 g, 1.3 eq), hydroxysuccinimide (NETS) (1.15 g, 1.0 eq) and triethylamine (3.2 mL, 2.3 eq) were slowly added. The reaction was carried out at room temperature for at least 5 hrs and the reaction was followed by TLC. Subsequently, the mixture was quenched by adding ddH$_2$O, and was extracted 2-3 times with DCM. The organic layer was collected, dried with anhydrous magnesium sulfate, filtered with MgSO$_4$ and then removal of DCM. The extract is purified with the column by using DCM:MeOH=9.8:0.2. The product was a pale yellow liquid. Yield: 81.2%.

Step 4. The 4-nitrophenyl chloroformate (3.35 g, 1.15 eq) was placed in two-neck bottle. Under vacuum for 1 hr, the three-way valve was diverted to nitrogen device and 60 mL DCM was added with a syringe. The weighted Step 3 Product was dissolved with 10-15 mL DCM, injected into the reaction flask with a syringe, and then slowly added with triethylamine (4.5 mL, 2.3 eq). The reaction was carried out in an ice bath for about 1 hr and then back to room temperature for overnight. After completion of the reaction, the mixture was quenched by adding ddH$_2$O, and was extracted 2-3 times with DCM. The organic layer was collected, dried with anhydrous magnesium sulfate, filtered with MgSO$_4$ and then removal of DCM. The extract is purified with the column by using EtOAc:Hex:MeOH=1:2:0.2. The product was a pale yellow liquid. After purification yield: 48.6%.

Step 5. The weighted Step 4 Product (3.5 g, 1.0 eq) was dissolved in 120 mL DCM, and then slowly added with Hydrazine hydrate (6.5 mL, 10.0 eq). The reaction was carried out at room temperature for about 24 hrs. The solution color turned from pale yellow to orange. After completion of the reaction, the mixture was quenched by adding ddH$_2$O, and extracted 2-3 times with DCM. The organic layer was collected, dried with anhydrous magnesium sulfate, filtered with MgSO$_4$ and then removal of DCM. The extract was purified with the column by using DCM:MeOH=9.5:0.5. In this step, the product was stuck in the column and the MeOH can be increased to 5% to elute the final product. The product (Linker IV-2) was a pale yellow sticky solid. After purification yield: 30.0%.

$^1$H (300 MHz) δ1.30-1.34 (2H, m), 1.47-1.56 (3H, m), 1.60-1.67 (1H, m), 1.82-1.87 (1H, m), 2.23 (2H, t), 2.54-2.56 (4H, m), 2.63-2.66 (4H, m), 3.07-3.25 (2H, m), 3.33-3.39 (3H, m), 3.40-3.43 (2H, m), 3.46-3.50 (5H, m), 3.54-3.58 (5H, m), 4.03-4.05 (2H, m), 4.07-4.10 (2H, m), 4.13-4.15 (2H, m)

$^{13}$C (100 MHz) δ24.5, 24.6, 27.5, 33.7, 34.7, 38.1, 41.0, 55.7, 55.8, 59.6, 59.7, 59.8, 65.7, 65.8, 65.9, 71.5, 71.7, 171.7, 171.9, 172.0, 177.1, 177.2, 177.3

Example 15 Preparation of Linker IV-C(O)O—

Step 1. The ethylene glycol (1.96 g, 1.05 eq) and Lipoic acid (6.19 g, 1.0 eq) were dissolved in 80 mL DCM, and N,N'-Dicyclohexylcarbodiimide (DCC) (8.04 g, 1.3 eq), 4-(Dimethylamino)pyridine (DMAP) (0.37 g, 0.1 eq) and triethylamine (9.6 mL, 2.3 eq) were slowly added. The reaction was carried out at room temperature for at least 5 hrs and the reaction was followed by TLC. Subsequently, the mixture was quenched by adding $ddH_2O$, and was extracted 2-3 times with DCM. The organic layer was collected, dried with anhydrous magnesium sulfate, filtered with $MgSO_4$ and then removal of DCM. The extract is purified with the column by using DCM:MeOH=9.8:0.2. The product was a pale yellow liquid. Yield: 66.0%.

Step 2. The Step 1 product (4.98 g, 1.0 eq) and succinic acid (2.48 g, 1.05 eq) were dissolved in 80 mL DCM, and N,N'-Dicyclohexylcarbodiimide (DCC) (5.36 g, 1.3 eq), 4-(Dimethylamino)pyridine (DMAP) (0.24 g, 0.1 eq) and triethylamine (6.4 mL, 2.3 eq) were slowly added. The reaction was carried out at room temperature for at least 5 hrs and the reaction was followed by TLC. Subsequently, the mixture was quenched by adding $ddH_2O$, and was extracted 2-3 times with DCM. The organic layer was collected, dried with anhydrous magnesium sulfate, filtered with $MgSO_4$ and then removal of DCM. The extract is purified with the column by using DCM:MeOH=9.5:0.5. The product was a pale yellow liquid. Yield: 81.2%.

Step 3. The Step 2 product (3.49 g, 1.0 eq) and 2-[2-(2-Aminoethoxy)ethoxy]ethanol (1.57 g, 1.05 eq) were dissolved in 80 mL DCM, and EDC.HCl (2.49 g, 1.3 eq), hydroxysuccinimide (NETS) (1.15 g, 1.0 eq) and triethylamine (3.2 mL, 2.3 eq) were slowly added. The reaction was carried out at room temperature for at least 5 hrs and the reaction was followed by TLC. Subsequently, the mixture was quenched by adding $ddH_2O$, and was extracted 2-3 times with DCM. The organic layer was collected, dried with anhydrous magnesium sulfate, filtered with $MgSO_4$ and then removal of DCM. The extract is purified with the column by using DCM:MeOH=9.8:0.2. The product was a pale yellow liquid. Yield: 80.5%.

Step 4. The 4-nitrophenyl chloroformat (3.35 g, 1.15 eq) was placed in two-neck bottle. Under vacuum for 1 hr, the three-way valve was diverted to nitrogen device and 60 mL DCM was added with a syringe. The weighted Step 3 Product was dissolved with 10-15 mL DCM, injected into the reaction flask with a syringe, and then slowly added with triethylamine (4.5 mL, 2.3 eq). The reaction was carried out in an ice bath for about 1 hr and then back to room temperature for overnight. After completion of the reaction, the mixture was quenched by adding $ddH_2O$, and was extracted 2-3 times with DCM. The organic layer was collected, dried with anhydrous magnesium sulfate, filtered with $MgSO_4$ and then removal of DCM. The extract is purified with the column by using EtOAc:Hex:MeOH=1:2:0.2. The product was a pale yellow liquid. After purification yield: 50.3%.

Step 5. The weighted Step 4 Product (3.5 g, 1.0 eq) was dissolved in 120 mL DCM, and then slowly added with Hydrazine hydrate (6.5 mL, 10.0 eq). The reaction was carried out at room temperature for about 24 hrs. The solution color turned from pale yellow to orange. After completion of the reaction, the mixture was quenched by adding $ddH_2O$, and extracted 2-3 times with DCM. The organic layer was collected, dried with anhydrous magnesium sulfate, filtered with $MgSO_4$ and then removal of DCM. The extract was purified with the column by using DCM:MeOH=9.5:0.5. In this step, the product was stuck in the column and the MeOH can be increased to 5% to elute the final product. The product was a pale yellow sticky solid. After purification yield: 31.0%.

Example 16 Preparation of SH—$C_5$-Linker-IV-Amide

Step 1. The ethanolamine (1.92 g, 1.05 eq) and 6-Acetyl-thiohexanoic acid (5.71 g, 1.0 eq) were dissolved in 80 mL DCM, and EDC.HCl (7.47 g, 1.3 eq), hydroxysuccinimide (NETS) (3.45 g, 1.0 eq) and triethylamine (9.6 mL, 2.3 eq) were slowly added. The reaction was carried out at room temperature for at least 5 hrs and the reaction was followed by TLC. Subsequently, the mixture was quenched by adding $ddH_2O$, and was extracted 2-3 times with DCM. The organic layer was collected, dried with anhydrous magnesium sulfate, filtered with $MgSO_4$ and then removal of DCM. The extract is purified with the column by using DCM:MeOH=9.8:0.2. The product was a pale yellow liquid. Yield: 74.0%.

Step 2. The Step 1 product (4.98 g, 1.0 eq) and succinic acid (2.48 g, 1.05 eq) were dissolved in 80 mL DCM, and N,N'-Dicyclohexylcarbodiimide (DCC) (5.36 g, 1.3 eq), 4-(Dimethylamino)pyridine (DMAP) (0.24 g, 0.1 eq) and triethylamine (6.4 mL, 2.3 eq) were slowly added. The reaction was carried out at room temperature for at least 5 hrs and the reaction was followed by TLC. Subsequently, the mixture was quenched by adding $ddH_2O$, and was extracted 2-3 times with DCM. The organic layer was collected, dried with anhydrous magnesium sulfate, filtered with $MgSO_4$ and then removal of DCM. The extract is purified with the column by using DCM:MeOH=9.5:0.5. The product was a pale yellow liquid. Yield: 80.2%.

Step 3. The Step 2 product (3.49 g, 1.0 eq) and 2-[2-(2-Aminoethoxy)ethoxy]ethanol (1.57 g, 1.05 eq) were dissolved in 80 mL DCM, and EDC.HCl (2.49 g, 1.3 eq), hydroxysuccinimide (NETS) (1.15 g, 1.0 eq) and triethylamine (3.2 mL, 2.3 eq) were slowly added. The reaction was carried out at room temperature for at least 5 hrs and the reaction was followed by TLC. Subsequently, the mixture was quenched by adding $ddH_2O$, and was extracted 2-3 times with DCM. The organic layer was collected, dried with anhydrous magnesium sulfate, filtered with $MgSO_4$ and then removal of DCM. The extract is purified with the column by using DCM:MeOH=9.8:0.2. The product was a pale yellow liquid. Yield: 80.0%.

Step 4. The 4-nitrophenyl chloroformate (3.35 g, 1.15 eq) was placed in two-neck bottle. Under vacuum for 1 hr, the three-way valve was diverted to nitrogen device and 60 mL DCM was added with a syringe. The weighted Step 3 Product was dissolved with 10-15 mL DCM, injected into the reaction flask with a syringe, and then slowly added with triethylamine (4.5 mL, 2.3 eq). The reaction was carried out in an ice bath for about 1 hr and then back to room temperature for overnight. After completion of the reaction, the mixture was quenched by adding $ddH_2O$, and was extracted 2-3 times with DCM. The organic layer was collected, dried with anhydrous magnesium sulfate, filtered with $MgSO_4$ and then removal of DCM. The extract is purified with the column by using EtOAc:Hex:MeOH=1:2:0.2. The product was a pale yellow liquid. After purification yield: 51.1%.

Step 5. The weighted Step 4 Product (3.5 g, 1.0 eq) was dissolved in 120 mL DCM, and then slowly added with Hydrazine hydrate (6.5 mL, 10.0 eq). The reaction was carried out at room temperature for about 24 hrs. The solution color turned from pale yellow to orange. After completion of the reaction, the mixture was quenched by adding ddH$_2$O, and extracted 2-3 times with DCM. The organic layer was collected, dried with anhydrous magnesium sulfate, filtered with MgSO$_4$ and then removal of DCM. The extract was purified with the column by using DCM:MeOH=9.5:0.5. In this step, the product was stuck in the column and the MeOH can be increased to 5% to elute the final product. The product was a pale yellow sticky solid. After purification yield: 28.0%.

Example 17 Preparation of SH—C$_5$-linker-IV-C(O)O—

Step 1. The ethylene glycol (1.96 g, 1.05 eq) and 6-Acetylthiohexanoic acid (5.71 g, 1.0 eq) were dissolved in 80 mL DCM, and N,N'-Dicyclohexylcarbodiimide (DCC) (8.04 g, 1.3 eq), 4-(Dimethylamino)pyridine (DMAP) (0.37 g, 0.1 eq) and triethylamine (9.6 mL, 2.3 eq) were slowly added. The reaction was carried out at room temperature for at least 5 hrs and the reaction was followed by TLC. Subsequently, the mixture was quenched by adding ddH$_2$O, and was extracted 2-3 times with DCM. The organic layer was collected, dried with anhydrous magnesium sulfate, filtered with MgSO$_4$ and then removal of DCM. The extract is purified with the column by using DCM:MeOH=9.8:0.2. The product was a pale yellow liquid. Yield: 71.5%.

Step 2. The Step 1 product (4.98 g, 1.0 eq) and succinic acid (2.48 g, 1.05 eq) were dissolved in 80 mL DCM, and N,N'-Dicyclohexylcarbodiimide (DCC) (5.36 g, 1.3 eq), 4-(Dimethylamino)pyridine (DMAP) (0.24 g, 0.1 eq) and triethylamine (6.4 mL, 2.3 eq) were slowly added. The reaction was carried out at room temperature for at least 5 hrs and the reaction was followed by TLC. Subsequently, the mixture was quenched by adding ddH$_2$O, and was extracted 2-3 times with DCM. The organic layer was collected, dried with anhydrous magnesium sulfate, filtered with MgSO$_4$ and then removal of DCM. The extract is purified with the column by using DCM:MeOH=9.5:0.5. The product was a pale yellow liquid. Yield: 81.4%.

Step 3. The Step 2 product (3.49 g, 1.0 eq) and 2-[2-(2-Aminoethoxy)ethoxy]ethanol (1.57 g, 1.05 eq) were dissolved in 80 mL DCM, and EDC.HCl (2.49 g, 1.3 eq), hydroxysuccinimide (NETS) (1.15 g, 1.0 eq) and triethylamine (3.2 mL, 2.3 eq) were slowly added. The reaction was carried out at room temperature for at least 5 hrs and the reaction was followed by TLC. Subsequently, the mixture was quenched by adding ddH$_2$O, and was extracted 2-3 times with DCM. The organic layer was collected, dried with anhydrous magnesium sulfate, filtered with MgSO$_4$ and then removal of DCM. The extract is purified with the column by using DCM:MOH=9.8:0.2. The product was a pale yellow liquid. Yield: 78.8%.

Step 4. The 4-nitrophenyl chloroformate (3.35 g, 1.15 eq) was placed in two-neck bottle. Under vacuum for 1 hr, the three-way valve was diverted to nitrogen device and 60 mL DCM was added with a syringe. The weighted Step 3 Product was dissolved with 10-15 mL DCM, injected into the reaction flask with a syringe, and then slowly added with triethylamine (4.5 mL, 2.3 eq). The reaction was carried out in an ice bath for about 1 hr and then back to room temperature for overnight. After completion of the reaction, the mixture was quenched by adding ddH$_2$O, and was extracted 2-3 times with DCM. The organic layer was collected, dried with anhydrous magnesium sulfate, filtered with MgSO$_4$ and then removal of DCM. The extract is purified with the column by using EtOAc:Hex:MeOH=1:2:0.2. The product was a pale yellow liquid. After purification yield: 51.1%.

Step 5. The weighted Step 4 Product (3.5 g, 1.0 eq) was dissolved in 120 mL DCM, and then slowly added with Hydrazine hydrate (6.5 mL, 10.0 eq). The reaction was carried out at room temperature for about 24 hrs. The solution color turned from pale yellow to orange. After completion of the reaction, the mixture was quenched by adding ddH$_2$O, and extracted 2-3 times with DCM. The organic layer was collected, dried with anhydrous magnesium sulfate, filtered with MgSO$_4$ and then removal of DCM. The extract was purified with the column by using DCM:MeOH=9.5:0.5. In this step, the product was stuck in the column and the MeOH can be increased to 5% to elute the final product. The product was a pale yellow sticky solid. After purification yield: 27.8%.

Example 18 Preparation of NH$_2$—C$_1$-Linker-IV-Amide

Step 1. The ethanolamine (1.92 g, 1.05 eq) and Boc-glycine (5.26 g, 1.0 eq) were dissolved in 80 mL DCM, and EDC.HCl (7.47 g, 1.3 eq), hydroxysuccinimide (NETS) (3.45 g, 1.0 eq) and triethylamine (9.6 mL, 2.3 eq) were slowly added. The reaction was carried out at room temperature for at least 5 hrs and the reaction was followed by TLC. Subsequently, the mixture was quenched by adding ddH$_2$O, and was extracted 2-3 times with DCM. The organic layer was collected, dried with anhydrous magnesium sulfate, filtered with MgSO$_4$ and then removal of DCM. The extract is purified with the column by using DCM:MeOH=9.8:0.2. The product was a pale yellow liquid. Yield: 62.0%.

Step 2. The Step 1 product (4.98 g, 1.0 eq) and succinic acid (2.48 g, 1.05 eq) were dissolved in 80 mL DCM, and N,N'-Dicyclohexylcarbodiimide (DCC) (5.36 g, 1.3 eq), 4-(Dimethylamino)pyridine (DMAP) (0.24 g, 0.1 eq) and triethylamine (6.4 mL, 2.3 eq) were slowly added. The reaction was carried out at room temperature for at least 5 hrs and the reaction was followed by TLC. Subsequently, the mixture was quenched by adding ddH$_2$O, and was extracted 2-3 times with DCM. The organic layer was collected, dried with anhydrous magnesium sulfate, filtered with MgSO$_4$ and then removal of DCM. The extract is purified with the column by using DCM:MeOH=9.5:0.5. The product was a pale yellow liquid. Yield: 80.4%.

Step 3. The Step 2 product (3.49 g, 1.0 eq) and 2-[2-(2-Aminoethoxy)ethoxy]ethanol (1.57 g, 1.05 eq) were dissolved in 80 mL DCM, and EDC.HCl (2.49 g, 1.3 eq), hydroxysuccinimide (NHS) (1.15 g, 1.0 eq) and triethylamine (3.2 mL, 2.3 eq) were slowly added. The reaction was carried out at room temperature for at least 5 hrs and the reaction was followed by TLC. Subsequently, the mixture was quenched by adding ddH$_2$O, and was extracted 2-3 times with DCM. The organic layer was collected, dried with anhydrous magnesium sulfate, filtered with MgSO$_4$ and then removal of DCM. The extract is purified with the column by using DCM:MeOH=9.8:0.2. The product was a pale yellow liquid. Yield: 71.0%.

Step 4. The 4-nitrophenyl chloroformat (3.35 g, 1.15 eq) was placed in two-neck bottle. Under vacuum for 1 hr, the three-way valve was diverted to nitrogen device and 60 mL DCM was added with a syringe. The weighted Step 3 Product was dissolved with 10-15 mL DCM, injected into the reaction flask with a syringe, and then slowly added with triethylamine (4.5 mL, 2.3 eq). The reaction was carried out in an ice bath for about 1 hr and then back to room temperature for overnight. After completion of the reaction, the mixture was quenched by adding ddH$_2$O, and was extracted 2-3 times with DCM. The organic layer was collected, dried with anhydrous magnesium sulfate, filtered with MgSO$_4$ and then removal of DCM. The extract is purified with the column by using EtOAc:Hex:MeOH=1:2:0.2. The product was a pale yellow liquid. After purification yield: 51.9%.

Step 5. The weighted Step 4 Product (3.5 g, 1.0 eq) was dissolved in 120 mL DCM, and then slowly added with Hydrazine hydrate (6.5 mL, 10.0 eq). The reaction was carried out at room temperature for about 24 hrs. The solution color turned from pale yellow to orange. After completion of the reaction, the mixture was quenched by adding ddH$_2$O, and extracted 2-3 times with DCM. The organic layer was collected, dried with anhydrous magnesium sulfate, filtered with MgSO$_4$ and then removal of DCM. The extract was purified with the column by using DCM:MeOH=9.5:0.5. In this step, the product was stuck in the column and the MeOH can be increased to 5% to elute the final product. The product was a pale yellow sticky solid. After purification yield: 29.0%.

Example 19 Preparation of NH$_2$—C$_1$-Linker-IV-C(O)O—

Step 1. The ethylene glycol (1.96 g, 1.05 eq) and Boc-glycine (5.26 g, 1.0 eq) were dissolved in 80 mL DCM, and N,N'-Dicyclohexylcarbodiimide (DCC) (8.04 g, 1.3 eq), 4-(Dimethylamino)pyridine (DMAP) (0.37 g, 0.1 eq) and triethylamine (9.6 mL, 2.3 eq) were slowly added. The reaction was carried out at room temperature for at least 5 hrs and the reaction was followed by TLC. Subsequently, the mixture was quenched by adding ddH$_2$O, and was extracted 2-3 times with DCM. The organic layer was collected, dried with anhydrous magnesium sulfate, filtered with MgSO$_4$ and then removal of DCM. The extract is purified with the column by using DCM:MeOH=9.8:0.2. The product was a pale yellow liquid. Yield: 75.0%.

Step 2. The Step 1 product (4.98 g, 1.0 eq) and succinic acid (2.48 g, 1.05 eq) were dissolved in 80 mL DCM, and N,N'-Dicyclohexylcarbodiimide (DCC) (5.36 g, 1.3 eq), 4-(Dimethylamino)pyridine (DMAP) (0.24 g, 0.1 eq) and triethylamine (6.4 mL, 2.3 eq) were slowly added. The reaction was carried out at room temperature for at least 5 hrs and the reaction was followed by TLC. Subsequently, the mixture was quenched by adding ddH$_2$O, and was extracted 2-3 times with DCM. The organic layer was collected, dried with anhydrous magnesium sulfate, filtered with MgSO$_4$ and then removal of DCM. The extract is purified with the column by using DCM:MeOH=9.5:0.5. The product was a pale yellow liquid. Yield: 80.5%.

Step 3. The Step 2 product (3.49 g, 1.0 eq) and 2-[2-(2-Aminoethoxy)ethoxy]ethanol (1.57 g, 1.05 eq) were dissolved in 80 mL DCM, and EDC.HCl (2.49 g, 1.3 eq), hydroxysuccinimide (NETS) (1.15 g, 1.0 eq) and triethylamine (3.2 mL, 2.3 eq) were slowly added. The reaction was carried out at room temperature for at least 5 hrs and the reaction was followed by TLC. Subsequently, the mixture was quenched by adding ddH$_2$O, and was extracted 2-3 times with DCM. The organic layer was collected, dried with anhydrous magnesium sulfate, filtered with MgSO$_4$ and then removal of DCM. The extract is purified with the column by using DCM:MeOH=9.8:0.2. The product was a pale yellow liquid. Yield: 81.0%.

Step 4. The 4-nitrophenyl chloroformat (3.35 g, 1.15 eq) was placed in two-neck bottle. Under vacuum for 1 hr, the three-way valve was diverted to nitrogen device and 60 mL DCM was added with a syringe. The weighted Step 3 Product was dissolved with 10-15 mL DCM, injected into the reaction flask with a syringe, and then slowly added with triethylamine (4.5 mL, 2.3 eq). The reaction was carried out in an ice bath for about 1 hr and then back to room temperature for overnight. After completion of the reaction, the mixture was quenched by adding ddH$_2$O, and was extracted 2-3 times with DCM. The organic layer was collected, dried with anhydrous magnesium sulfate, filtered with MgSO$_4$ and then removal of DCM. The extract is purified with the column by using EtOAc:Hex:MeOH=1:2:0.2. The product was a pale yellow liquid. After purification yield: 50.6%.

Step 5. The weighted Step 4 Product (3.5 g, 1.0 eq) was dissolved in 120 mL DCM, and then slowly added with Hydrazine hydrate (6.5 mL, 10.0 eq). The reaction was carried out at room temperature for about 24 hrs. The solution color turned from pale yellow to orange. After completion of the reaction, the mixture was quenched by adding ddH$_2$O, and extracted 2-3 times with DCM. The organic layer was collected, dried with anhydrous magnesium sulfate, filtered with MgSO$_4$ and then removal of DCM. The extract was purified with the column by using DCM:MeOH=9.5:0.5. In this step, the product was stuck in the column and the MeOH can be increased to 5% to elute the final product. The product was a pale yellow sticky solid. After purification yield: 31.2%.

Example 20 Cytotoxicity Assay of Linkers of the Invention

We examined the cytotoxicity of 9 linkers and the IC$_{50}$ value for each linker was calculated. The human brast adenocarcinoma MCF7, MDA-MB-453 and MDA-MB-231 and human mammary epithelial cell H184B5F5/M10 were choosed for cytotoxicity test. Cells were seeded in 6-well plates and treated Linker I-1 (Linker I-amide, m=2), Linker I-2 (Linker I-amide, m=1), Linker I-3 (Linker I-amide, m=3), Linker I-4 (Linker I-amide, m=4), Linker I-5 (Linker I-amide, m=5), Linker II-1 (Linker II-amide, z=1), Linker II-2 (Linker II-amide, z=2), Linker II-3 (Linker II-amide, z=3), and Linker II-4 (Linker II-amide, z=4), and further incubated for 72 hours at 37° C. After took photos, cells were counted by using hemocytometer. Growth inhibition was compared with untreated controls to find the linker concentration which inhibited growth by 50% (IC$_{50}$). The summary of IC$_{50}$ is showed in Table. 1. The IC$_{50}$ value were 300 to 700 μM in linker I-1 to linker I-5 and linker II-1. The IC$_{50}$ value of linker II-2 to II-4 is more than 800 μM. These data suggesting that the cellular toxicity is low to as a linker for conjugate drug and gold nanoparticles for drug delivery.

Table. 1 Summary of IC$_{50}$ value of linkers cytotoxicity in human brast adenocarcinoma MCF7, MDA-MB-453 and MDA-MB-231 and human mammary epithelial cell H184B5F5/M10 for 72 hrs.

| IC$_{50}$ value for linker cytotoxicity (μM) | MCF7 | MDA-MB-231 | M10 | MDA-MB-453 |
|---|---|---|---|---|
| Linker I-1 | 692.0 ± 51.9 | 528.9 ± 52.1 | 584.4 ± 62.7 | 298.6 ± 23 |
| Linker I-2 | 730 ± 36.7 | 535.6 ± 21.6 | 685.7 ± 105.5 | 432.5 ± 96.6 |
| Linker I-3 | 538.2 ± 39.6 | 453.7 ± 141.7 | 555 ± 33.5 | 332.9 ± 9.8 |
| Linker I-4 | 569.2 ± 14.1 | 575.6 ± 81.9 | 560 ± 45.1 | 342.3 ± 11 |
| Linker I-5 | 418.9 ± 23.8 | 484.3 ± 64.6 | 569.3 ± 54.7 | 460 ± 87.9 |
| Linker II-1 | 500.8 | 474.3 | 500.4 | >800 |
| Linker II-2 | >800 | >800 | >800 | >800 |
| Linker II-3 | >800 | 428.3 ± 116.2 | 585.3 ± 132.2 | >800 |
| Linker II-4 | >800 | >800 | >800 | >800 |
| Linker IV-2 | >800 | 655.5 | >800 | 708.4 ± 35.3 |
| Linker SHI-1 | >800 | 558.9 ± 23.3 | >800 | 128.3 ± 15.1 |
| Linker SHI-4 | >800 | 532.7 ± 63.9 | >800 | 129.7 ± 13.4 |

Example 21 Preparations of Complexes of Gold Nanoparticles, Linker and Anti-Cancer Drug and/or Antibody 1. Au/LKI-1/mAb-p24 Complex Preparation of Au/LKI-1/mAb-p24 Complex To conjugate antibody onto gold nanoparticles, anti-HIV-1 p24 (HIV-1 p24) (GeneTex, GTX41595) antibody was concentrated using 10 kDa MWCO centrifugal filter (Millipore, UFC501024) and was dissolved in 100 mM Na$_2$HPO$_4$, pH 7.4 buffer at 1 mg/mL. Then, 5 μL of 100 mM NaIO$_4$ in water was added to 50 μL of antibody solution and the mixture was incubated in dark for 30 minutes. The reaction was quenched by adding 250 μL of 1×PBS.

At this point the carbohydrate moieties on the Fc portion of the antibody were oxidized to aldehyde groups. Then, Linker I-1 (Linker I-amide, m=2) was added to the antibody solution. The linker has hydrazide and dithiol groups on opposing sites of the molecule. The hydrazide moiety interacts with aldehyde groups of the Fc portion of the modified antibody molecules. The reaction mixture was incubated at room temperature for 2 hours and then the thiolated antibodies were collected using centrifugal filters and resuspended in 0.1 M sodium phosphate buffer, pH 7.4. One hundred microliters of the thiolated antibodies at concentration of 0.1 mg/ml were mixed with 0.5 mL of gold nanoparticles and the suspension was incubated at room temperature for 1 hr. Keep the antibody-gold nanoparticles complexes at 4° C. for storage for further use.

Characterization of Au/LKI-1/mAb-p24 Complex

Figure 1B:
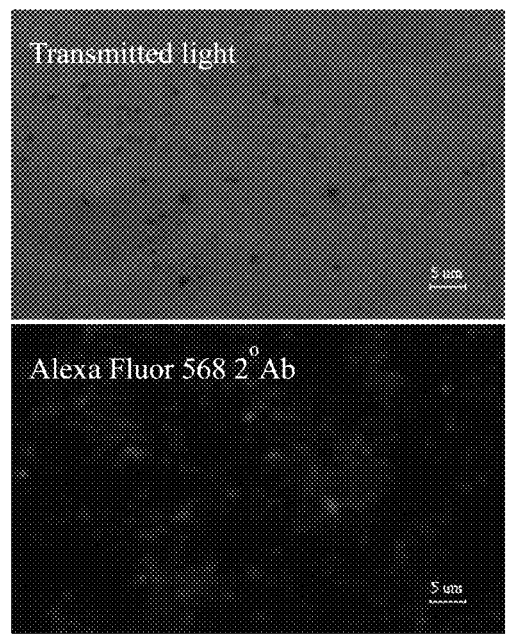
Figure 1C:
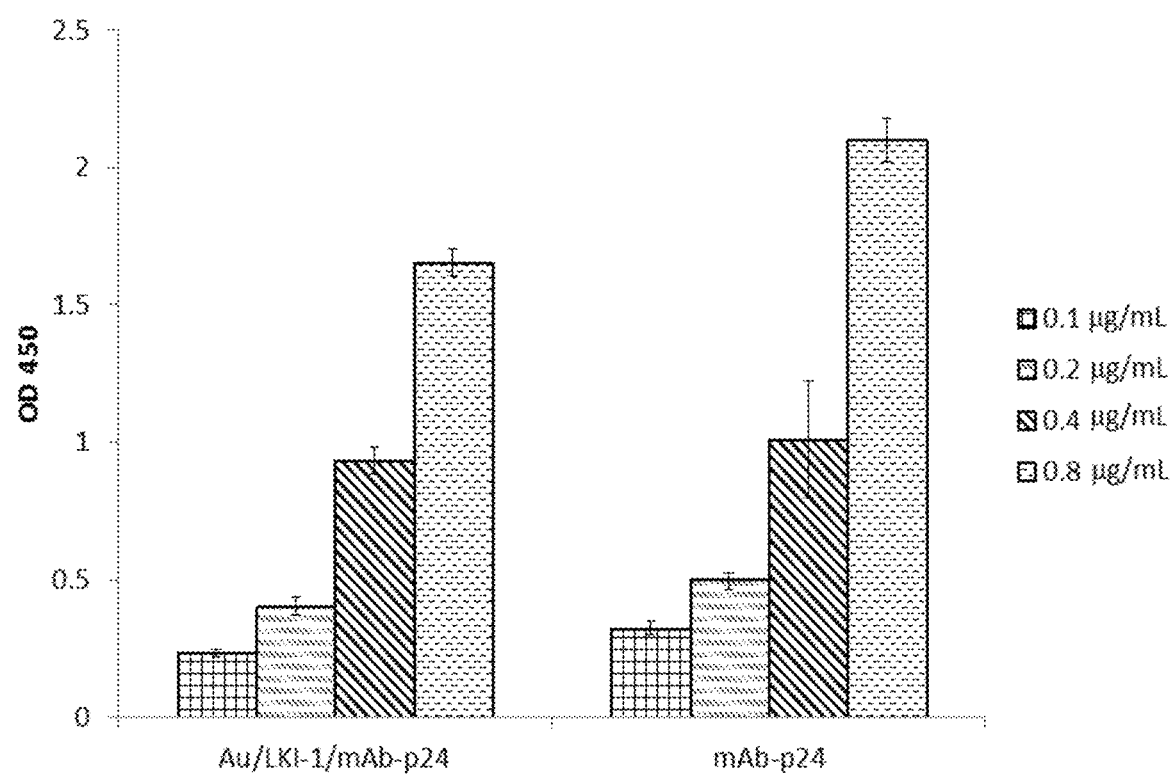

The formulation of Au/LKI-1/mAb-p24 complex was analyzed with a UV-Vis spectrophotometer (Beckman, DU 800). The surface plasmon resonance spectra recorded showed a 2 nm red shift in the plasmon peak ($\lambda_{max}$) of the antibody-conjugated gold nanoparticles (FIG. 1A). Red fluorescence images of Alex Fluor 568 secondary antibodies labeled Au/LKI-1/mAb-p24 complex was measured using an inverted microscope (Nikon, TE2000-U). Each gold nanoparticle showed red fluorescence suggesting that each gold nanoparticle conjugated with anti-HIV-1 P24 antibodies on surface (FIG. 1B). Furthermore, we investigated the binding affinity of anti-HIV-1 P24 antibodies on gold nanoparticles. From ELISA, we could confirm the binding affinity of Au/LKI-1/mAb-p24 complexes to anti-HIV-1 P24 proteins (FIG. 1C).

2. Au/LKI-1 or LK I-5/Ab-EGFR Complex

Preparation of Au/LKI-1 or LK I-5/Ab-EGFR Complex

To conjugate antibody onto gold nanoparticles, anti-human EGFR clone H11 (Thermo, MA1-12693) was concentrated using 10 kDa MWCO centrifugal filter (Millipore, UFC501024) and was dissolved in 100 mM Na$_2$HPO$_4$, pH 7.4 buffer at 1 mg/mL. Then, 5 μL of 100 mM NaIO$_4$ in water was added to 50 μL of antibody solution and the mixture was incubated in dark for 30 minutes. The reaction was quenched by adding 250 μL of 1×PBS. At this point the carbohydrate moieties on the Fc portion of the antibody were oxidized to aldehyde groups. Then, Linker I-1 (Linker I-amide, m=2) or Linker I-5 (Linker I-amide, m=5) was added to the antibody solution. The linker has hydrazide and dithiol groups on opposing sites of the molecule. The hydrazide moiety interacts with aldehyde groups of the Fc portion of the modified antibody molecules. The reaction mixture was incubated at room temperature for 2 hours and then the thiolated antibodies were collected using centrifugal filters and resuspended in 0.1 M sodium phosphate buffer, pH 7.4. One hundred microliters of the thiolated antibodies at concentration of 0.1 mg/ml were mixed with 0.5 mL of gold nanoparticles and the suspension was incubated at room temperature for 1 hr. Keep the antibody-gold nanoparticles complexes at 4° C. for storage for further use.

Characterization of Au/LKI-1 or LK I-5/Ab-EGFR Complex

Figure 2:
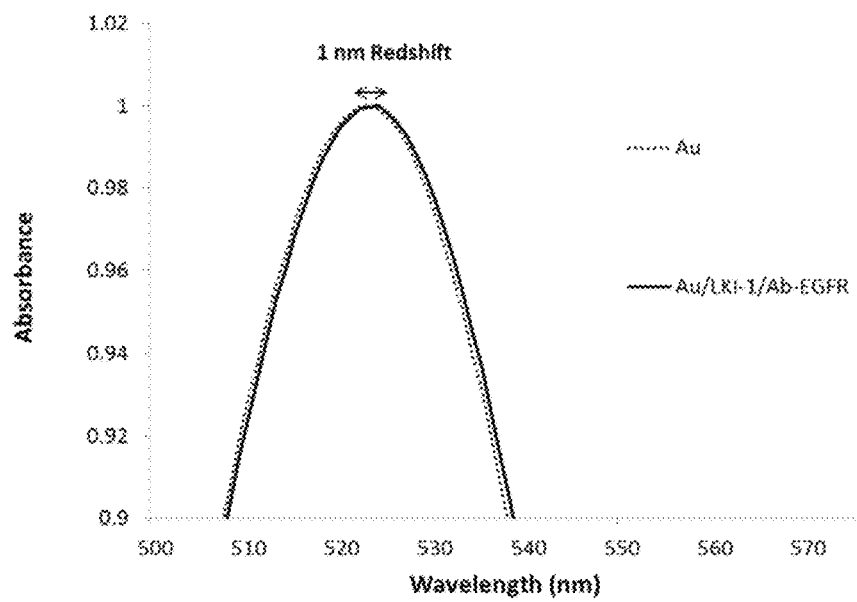
FIGS. 2 (A) to (B) show the absorption spectrum of EGFR (epidermal growth factor receptor) antibodies conjugated onto gold nanoparticles (Au/LKI-1/Ab-EGFR and Au/LKI-5/Ab-EGFR) and Au. (A) The Au/LKI-1/Ab-EGFR complex shows a 1 nm red shift in the plasmon peak. (B) The Au/LKI-5/Ab-EGFR complex shows a 1 nm red shift in the plasmon peak.
Figure 2:
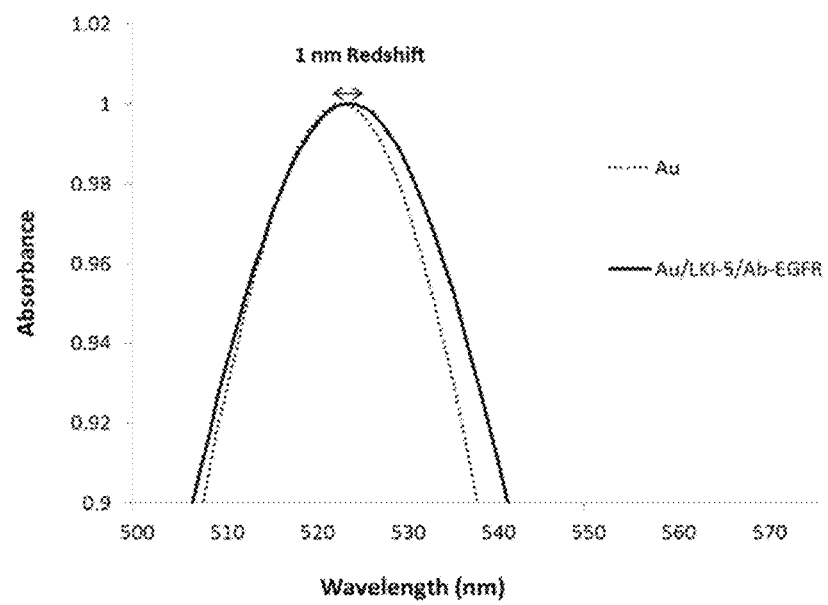

The formulation of Au/LKI-1/Ab-EGFR complex or Au/LK I-5/Ab-EGFR complex was analyzed with a UV-Vis spectrophotometer (Beckman, DU 800). The surface plasmon resonance spectra recorded showed a 2 nm red shift in the plasmon peak ($\lambda_{max}$) of the antibody-conjugated gold nanoparticles (FIG. 2). We examined two linkers, Linker I-1 (Linker I-amide (m=2)) and linker I-5 (Linker I-amide (m=5)), for EGFR antibody and gold nanoparticles conjugation. Flow cytometry analysis of Au/LKI-1/Ab-EGFR complex and Au/LKI-5/Ab-EGFR complex were demonstrated targeting affinity on human breast adenocarcinoma MCF-7 cells. Both Au/LKI-1/Ab-EGFR complex and Au/LKI-5/Ab-EGFR complex were showed similar targeting ability comparing to EGFR antibody (Table. 2). These data were suggested that linker is suitable for antibody and gold nanoparticles conjugation and keep the binding affinity for antibody.

TABLE 2

Flow cytometric analysis of the targeting effect of Ab-EGFR, Au/LKI-1/Ab-EGFR complex and Au/LKI-5/Ab-EGFR complex on EFGR of the surface in MCF-7 breast tumor cells.

|  | Ab-EGFR | Au/LKI-1/Ab-EGFR complex | Au/LKI-5/Ab-EGFR complex |
|---|---|---|---|
| % EGFR to target on cell surface (cell line: MCF-7) | 71.5 | 68 | 67 |

3. Au/LKI-1/Trastuzumab (Tras) Complex

Preparation of Au/LKI-1/Tras Complex

To conjugate antibody onto gold nanoparticles, Tras (JHL biotech, JHL1188) antibody was concentrated using 10 kDa MWCO centrifugal filter (Millipore, UFC501024) and was dissolved in 100 mM $Na_2HPO_4$, pH 7.4 buffer at 1 mg/mL. Then, 5 μL of 100 mM $NaIO_4$ in water was added to 50 μL of antibody solution and the mixture was incubated in dark for 30 minutes. The reaction was quenched by adding 250 μL of 1×PBS. At this point the carbohydrate moieties on the Fc portion of the antibody were oxidized to aldehyde groups. Then, Linker I-1 (Linker I-amide (m=2)) were added to the antibody solution. The linker has hydrazide and dithiol groups on opposing sites of the molecule. The hydrazide moiety interacts with aldehyde groups of the Fc portion of the modified antibody molecules. The reaction mixture was incubated at room temperature for 2 hours and then the thiolated antibodies were collected using centrifugal filters and resuspended in 0.1 M sodium phosphate buffer, pH 7.4. One hundred microliters of the thiolated antibodies at concentration of 0.1 mg/ml were mixed with 0.5 mL of gold nanoparticles and the suspension was incubated at room temperature for 1 hr. Keep Au/LKI-1/Tras complex at 4° C. for storage for further use.

Characterization of Au/LKI-1/Tras Complex

Figure 3:
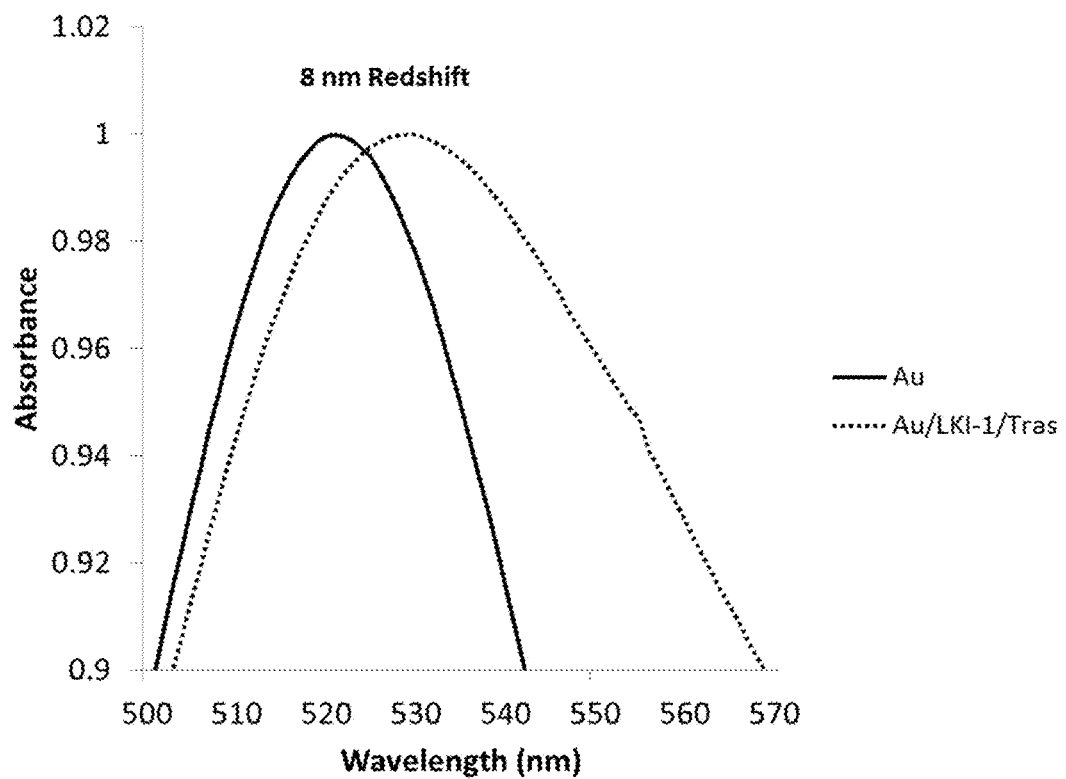
FIG. 3 shows the absorption spectrum of Trastuzumab (Tras) antibodies conjugated onto gold nanoparticles (Au/LKI-1/Tras) and Au. The Au/LKI-1/Tras complex shows a 8 nm red shift in the plasmon peak.

The formulation of Au/LKI-1/Tras complex was analyzed with a UV-Vis spectrophotometer (Beckman, DU 800). The surface plasmon resonance spectra recorded showed a 8 nm red shift in the plasmon peak ($\lambda_{max}$) of the antibody-conjugated gold nanoparticles (FIG. 3). We examined Au/LKI-1/Tras complex. Flow cytometry analysis of Au/LKI-1/Tras complex were demonstrated targeting affinity on human breast adenocarcinoma cells. Au/LKI-1/Tras complex were showed similar targeting ability comparing to Trastuzumab (Table. 3).

TABLE 3

Flow cytometric analysis of the targeting effect of Tras and Au/LKI-1/Tras complex on Her2/neu of the surface in MDA-MB-453 breast tumor cells.

|  | Ab-EGFR | Au/LKI-1/Ab-EGFR complex |
|---|---|---|
| % Trastuzumab to Her2/neu on cell surface (cell line: MDA-MB-453) | 99.89 | 99.98 |

4. Au/LKI-1/Etanercept (ETA) Complex

Preparation of Au/LKI-1/ETA Complex

To conjugate antibody onto gold nanoparticles, Etanercept (ETA) (Mycenax biotech, TuNEX) was concentrated using 10 kDa MWCO centrifugal filter (Millipore, UFC501024) and was dissolved in 100 mM $Na_2HPO_4$, pH 7.4 buffer at 1 mg/mL. Then, 5 μL of 100 mM $NaIO_4$ in water was added to 50 μL of antibody solution and the mixture was incubated in dark for 30 minutes. The reaction was quenched by adding 250 μL of 1×PBS. At this point the carbohydrate moieties on the Fc portion of the antibody were oxidized to aldehyde groups. Then, linker I-1 was added to the antibody solution. The linker has hydrazide and dithiol groups on opposing sites of the molecule. The hydrazide moiety interacts with aldehyde groups of the Fc portion of the modified antibody molecules. The reaction mixture was incubated at room temperature for 2 hours and then the thiolated antibodies were collected using centrifugal filters and resuspended in 0.1 M sodium phosphate buffer, pH 7.4. One hundred microliters of the thiolated antibodies at concentration of 0.1 mg/ml were mixed with 0.5 mL of gold nanoparticles and the suspension was incubated at room temperature for 1 hr. Keep Au/LKI-1/ETA complex at 4° C. for storage for further use.

Characterization of Au/LKI-1/ETA Complex

Figure 4:
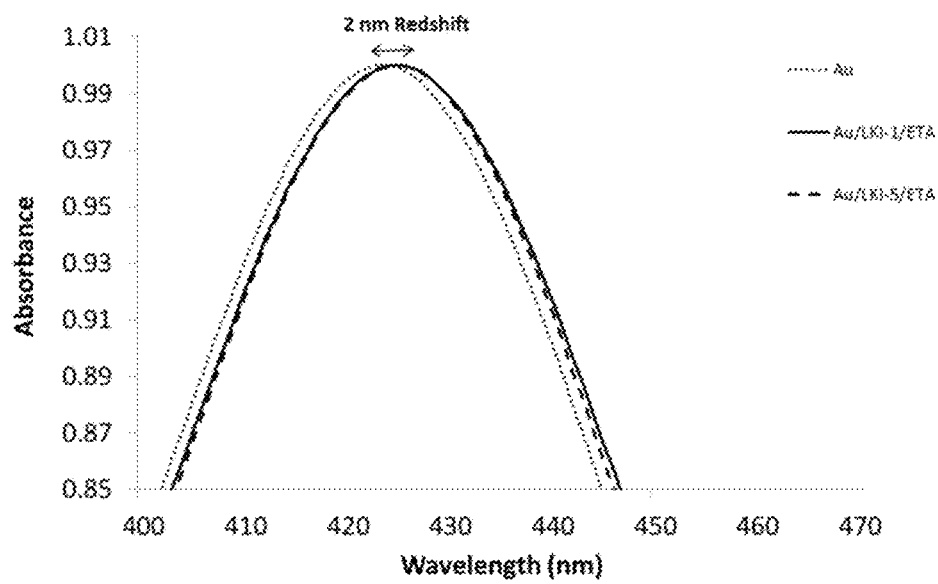
FIG. 4 (A) to (C) show Etanecept (ETA) conjugated onto gold nanoparticles (Au/LKI-1/ETA) still showed the binding affinity. (A) The absorption spectrum of Au/LKI-1/ETA complex and Au. The Au/LKI-1/ETA complex shows a 2 nm red shift in the plasmon peak. (B) The Au/LKI-1/ETA complex showed fluorescence by detected with Alexa Fluor 568 secondary antibodies. (C) TEM images of Au/LKI-1/ETA complex, binding of 1-5 nm gold-labeled secondary anti-human IgG antibodies to ETA located on the Au surface was observed.
Figure 4:
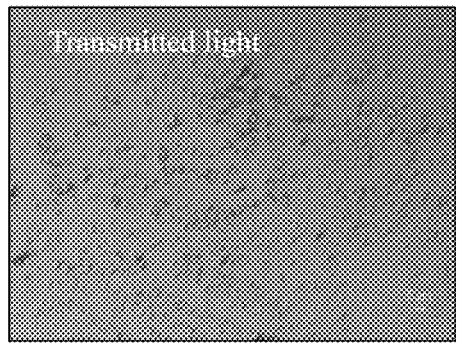
Figure 4:
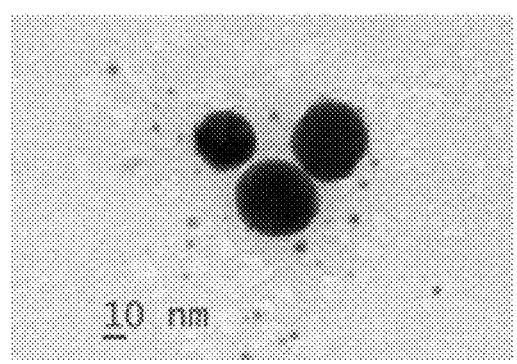

The formulation of Au/LKI-1/ETA complex was analyzed with a UV-Vis spectrophotometer (Beckman, DU 800). The surface plasmon resonance spectra recorded showed a 2 nm red shift in the plasmon peak ($\lambda_{max}$) of Au/LKI-1/ETA (FIG. 4A). Red fluorescence images of Alex Fluor 568 secondary antibodies labeled Au/LKI-1/ETA complex was measured using an inverted microscope (Nikon, TE2000-U). Each gold nanoparticle showed red fluorescence suggesting that each gold nanoparticle conjugated with ETA antibodies on surface (FIG. 4B). We further examined Au/LKI-1/ETA complex by binding with secondary antibody conjugated with 1-5 nm AuNPs. In TEM images of Au/LKI-1/ETA complex, binding of 1-5 nm gold-labeled secondary anti-human IgG antibodies to ETA located on the AuNP surface was observed (FIG. 4C). We further investigated the TNFα blocking ability of ETA and Au/LKI-1/ETA. MCF-7 cells ($5 \times 10^5$) were treated with the mixtures of 12.5 ng/mL TNFα and 62.5, 125, 250, 500 ng/mL ETA or Au/LKI-1/ETA complex for 2 hours, respectively. The treated cells were incubated at 37° C. for 72 hours and then the cell numbers were counted by MTS [(3-(4,5-dimethylthiazol-2-yl)-5-(3-carboxymethoxyphenyl)-2-(4-sulfophenyl)-2H-tetrazolium)] assay. The TNFα blocking ability was observed in both ETA only and Au/LKI-1/ETA complex. ETA and Au/LKI-1/ETA complex were used to test their abilities in blocking TNFα induced MCF-7 cell apoptosis, Table 4. Au/LKI-1/ETA complex was showed similar blocking TNFα ability comparing to ETA

TABLE 4

The ability of Au/LKI-1/ETA complex to block TNFα-induced MCF-7 cell apoptosis

| TNFα 12.5 ng/mL | Relative cell survival % | |
|---|---|---|
| Dose (ng/mL) | ETA | Au/LKI-1/ETA Complex |
| 62.5 | 36.7 ± 1.4 | 35.6 ± 4.9 |
| 125 | 68.5 ± 2.3 | 54.9 ± 3.1 |
| 250 | 82.1 ± 6.5 | 67.2 ± 2.2 |
| 500 | 103.3 ± 0.9 | 100.9 ± 5.4 |

5. Au/LKI-1/Doxorubicin (Dox) Complex

Preparation of Au/LKI-1/Dox Complex 1 eq. doxorubicin and 2 eq. linker I-1 (Linker I-amide (m=2)) were added to dry MeOH and mixed at room temperature. TFA (1.3 eq.) was added to the resulting mixture for reaction overnight. The resulting mixture was filtered to obtain clear solution. The clear solution was added to a flask with 50 mL EtOAc by dropper, stirred for 20 minutes and filtered to obtain Dox-Linker-1 solid. The resulting solid was wash with EtOAc and then dried. 400 μL Dox/LKI-1 (2000 ppm) and 2 μL NaOH were added to 1 mL AuNPs (50 ppm) and then mixed for 21 hours. The mixture was centrifuged at 1400 rpm for 20 minutes. The resulting precipitate was washed by DI water and the resulting precipitate was resuspended in DI water. PEGs (2K, 2000 Da) were added to the suspension and mixed for overnight to obtain Au/LKI-1/Dox complex.

Characterization of Au/LKI-1/Dox Complex

Figure 5:
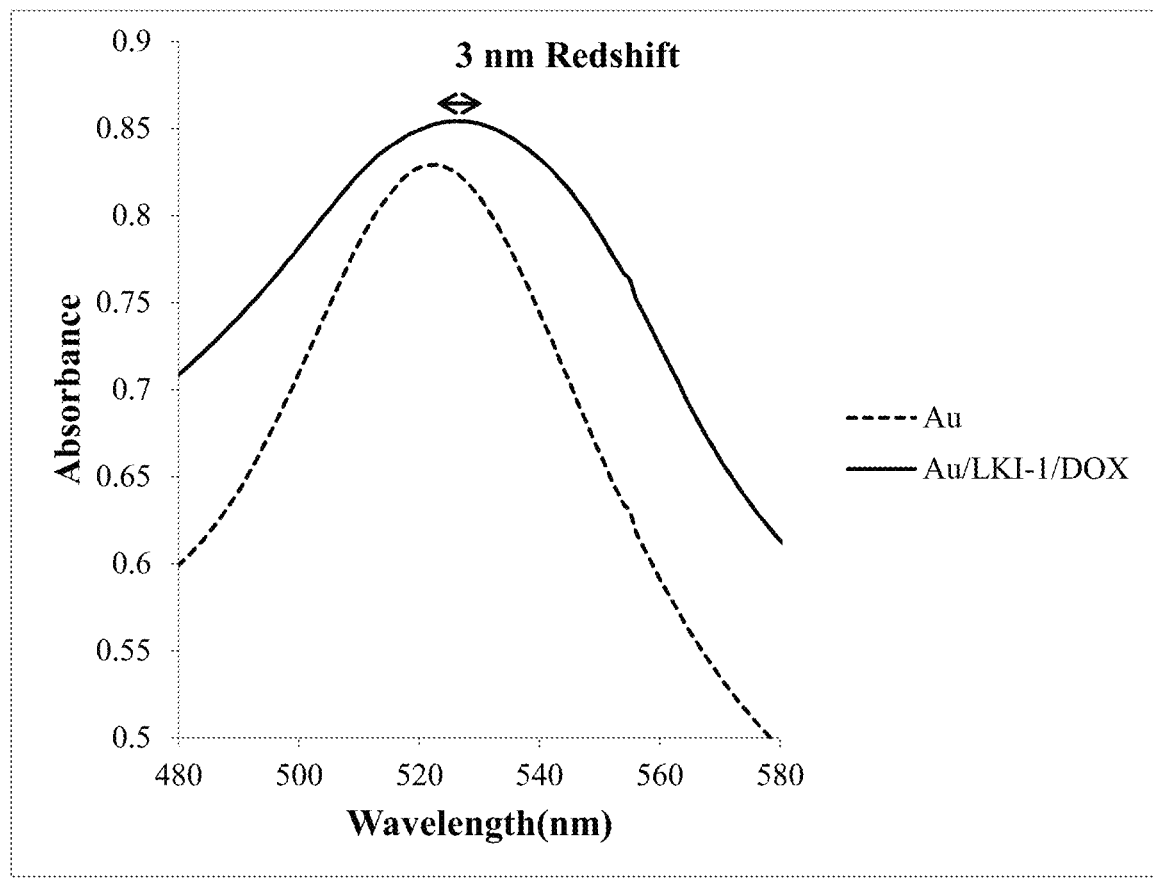
FIG. 5 shows the absorption spectrum of Au/LKI-1/Dox complex and Au. The UV/vis data, the wavelength, shows a 3 nm red shift in Au/LKI-1/Dox complex.

The Au/LKI-1/DOX complex was analyzed with a UV-Vis spectrophotometer (Beckman, DU 800). The surface plasmon resonance spectra recorded showed a 3 nm red shift in the plasmon peak ($\lambda_{max}$) of the Au/LKI-1/Dox complex (FIG. 5).

Others linkers, I-2, I-3, I-4, I-5, II-1, II-2, II-3, II-4, IV-2, SHI-1 and SHI-4, were used to conjugate DOX and gold nanoparticles to obtain various complexes according to the above-mentioned process.

Example 22 Cytotoxicity Assay of Au/Linkers(LKs)/Dox Complexes

We examined the cytotoxicity of Au/LKs/Dox complexes and the $IC_{50}$ value was calculated. The human brast adenocarcinoma MCF7, MDA-MB-453 and MDA-MB-231 and human mammary epithelial cell H184B5F5/M10 were choosed for cytotoxicity test. Cells were seeded in 96-well plates and treated 2 µM doxorubicin (Dox), 20-50 nm gold nanoparticles conjugated with doxorubicin using various linkers as shown in the table below and capped with SH-PEG (Au/LK/Dox, contained 2 µM doxorubicin) and further incubated for 72 hours at 37° C. The CellTiter 96® AQueous One Solution Cell Proliferation Assay (MTS) reagent was purchased from Promega (Madison, Wis., USA) and the assay was performed according to the manufacturer's instructions. Absorbance was measured at 490 nm using a microplate reader (Bio-tek, Powerwave X340, Winooski, Vt., USA). Growth inhibition was compared with untreated controls to find the Au/LKs/Dox complexes concentration which inhibited growth by 50% ($IC_{50}$).

TABLE 5

Summary of $IC_{50}$ value of Au/LKs/Dox complexes cytotoxicity in human brast adenocarcinoma MCF7, MDA-MB-453 and MDA-MB-231 and human mammary epithelial cell H184B5F5/M10 for 72 hrs.

| $IC_{50}$ value for complex cytotoxicity (µM) | MCF7 | MDA-MB-231 | MDA-MB-453 | M10 |
|---|---|---|---|---|
| Au/Linker I-1/Dox | 0.54 ± 0.03 | 0.5 ± 0.082 | 1.93 ± 0.2 | 0.49 ± 0.0138 |
| Au/Linker I-2/Dox | 0.7 ± 0.0096 | 0.86 ± 0.056 | 0.7 ± 0.05 | 0.46 ± 0.058 |
| Au/Linker I-3/Dox | >2.0 | >2.0 | >2.0 | >2.0 |
| Au/Linker I-4/Dox | >2.0 | >2.0 | >2.0 | >2.0 |
| Au/Linker I-5/Dox | >2.0 | >2.0 | >2.0 | >2.0 |
| Au/Linker II-1/Dox | 0.65 ± 0.037 | 0.83 ± 0.027 | 0.69 ± 0.026 | 0.56 ± 0.015 |
| Au/Linker II-2/Dox | >2.0 | 0.98 ± 0.26 | >2.0 | 0.67 ± 0.1 |
| Au/Linker II-3/Dox | 0.76 ± 0.03 | 0.46 ± 0.035 | 0.85 ± 0.319 | 0.19 ± 0.03 |
| Au/Linker II-4/Dox | >2.0 | >2.0 | 1.9 ± 0.12 | 0.7 ± 0.137 |
| Au/Linker IV-2/Dox | 0.77 ± 0.02 | 0.57 ± 0.048 | 0.73 ± 0.073 | 0.49 ± 0.031 |
| Au/Linker SHI-1/Dox | 0.82 ± 0.09 | >2.0 | >2.0 | >2.0 |
| Au/Linker SHI-4/Dox | 0.75 ± 0.15 | >2.0 | >2.0 | >2.0 |
| Dox | 0.41 ± 0.055 | 0.67 ± 0.088 | 0.65 ± 0.072 | 0.14 ± 0.034 |

The $IC_{50}$ value were 0.46~1.93 µM in Au/LK/Dox complex (LKI-1, LKI-2, LKII-1, LKII-3 and LKIV-2) for cancer cells (MCF-7, MDA-MB-231, MDA-MB-453) similar to Dox. For the normal cell, M10, the cellular toxicity of complexes are lower than Dox. The data suggests that the Au/LKs/Dox complexes are more safety than Dox.

Example 23 pH-Sensitive LKI-1 Release Test of Au/LKI-1/Dox Complex 1 mL of Au/LKI-1/Dox complex solution was centrifuged at 14000 rpm for 20 minutes. The supernatant was discarded and a buffer with pH 5.5 or a buffer with pH 7.4 was added thereto. After different time points, the complex solution was centrifuged at 14000 rpm for 20 minutes and then the supernatant was taken to subjected to fluorescence scan at 557.6 nm (F-4500 FL Spectrophotometer) to obtain OD values. The Dox amounts released from the complex can be obtained by interpolating from a Dox standard curve (X hours Dox release amount).

1 mL of Au/LKI-1/Dox complex solution was centrifuged at 14000 rpm for 20 minutes. The supernatant was discarded and a buffer with pH 1.0 was added thereto. After one hour, the complex solution was centrifuged at 14000 rpm for 20 minutes and then the supernatant was taken to subjected to fluorescence scan at 557.6 nm (F-4500 FL Spectrophotometer) to obtain OD values. The Dox 100% release can be obtained by interpolating from a Dox standard curve (pH=1 incubation 1 h Dox release amount). The Dox cumulative release percentage is calculated according to the following formula.

Dox cumulative release %=($X$ hours Dox release amount/pH=1 incubation 1 h Dox release amount)*100%

TABLE 6 pH-sensitive LKI-1 release test of Au/LKI-1/Dox complex

| | Dox release of Au/LKI-1/Dox, (%) | |
|---|---|---|
| Incubation time (h) | pH = 5.5 | pH = 7.4 |
| 1 | 23.40 | 6.12 |
| 3 | 27.87 | 7.30 |

TABLE 6-continued pH-sensitive LKI-1 release test of Au/LKI-1/Dox complex

| | Dox release of Au/LKI-1/Dox, (%) | |
|---|---|---|
| Incubation time (h) | pH = 5.5 | pH = 7.4 |
| 5 | 27.80 | 7.39 |
| 7 | 32.11 | 7.54 |
| 12 | 37.16 | 7.51 |
| 24 | 46.01 | 7.91 |
| 48 | 55.39 | 8.96 |
| 72 | 70.45 | 8.88 |

The data shows LKI-1 could release more Dox at pH5.5 than at pH 7.4. In Au/LKI-1/Dox, Dox was more and more released in time-dependent.

Example 24 Efficacy Study Design

Figure 6A:
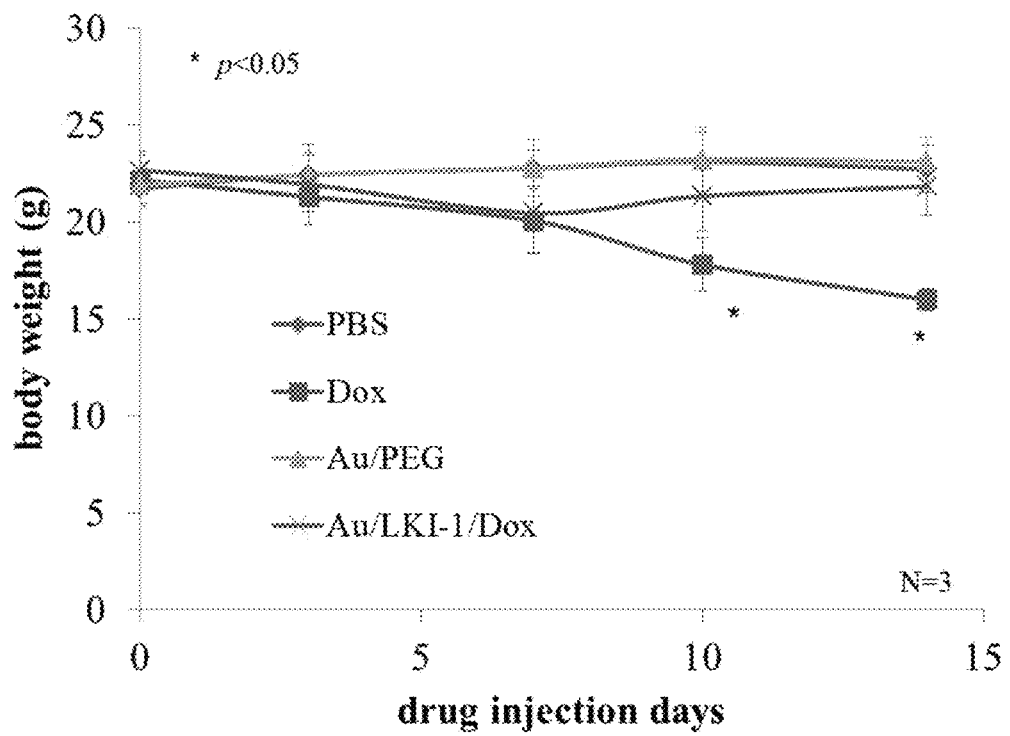
FIG. 6 (A) to (D) show the treatment of MDA-MB-231 breast tumors. (A) Net animal weight change (g) during the treatment. From the data, doxorubicin and Au/LKI-1/Dox was cause the weight loss over 20% and 3% in nude mice (N=3), respectively. That means Au/LKI-1/Dox complex in comparison with doxorubicin were much less toxicity in nude mice. (B) The inhibition of MDA-MD-231 breast tumor growth (N=3): Dox>Au/LKI-1/Dox>Au/PEG=PBS. (C) TEM images of MDA-MB-231 breast tumor cells treated with Au/LKI-1/Dox complex was easy determined the Au/LKI-1/Dox complex in the tumor in xenograft model. (D) Immunohistochemistry of tumor specimens. Breast tumor specimens were taken from the mice, embedded in paraffin and stained with hematoxylineosin. The more necrosis was observed in tumor from mice treated with doxorubicin than in tumors from mice treated with Au/LKI-1/Dox complex.
Figure 6B:
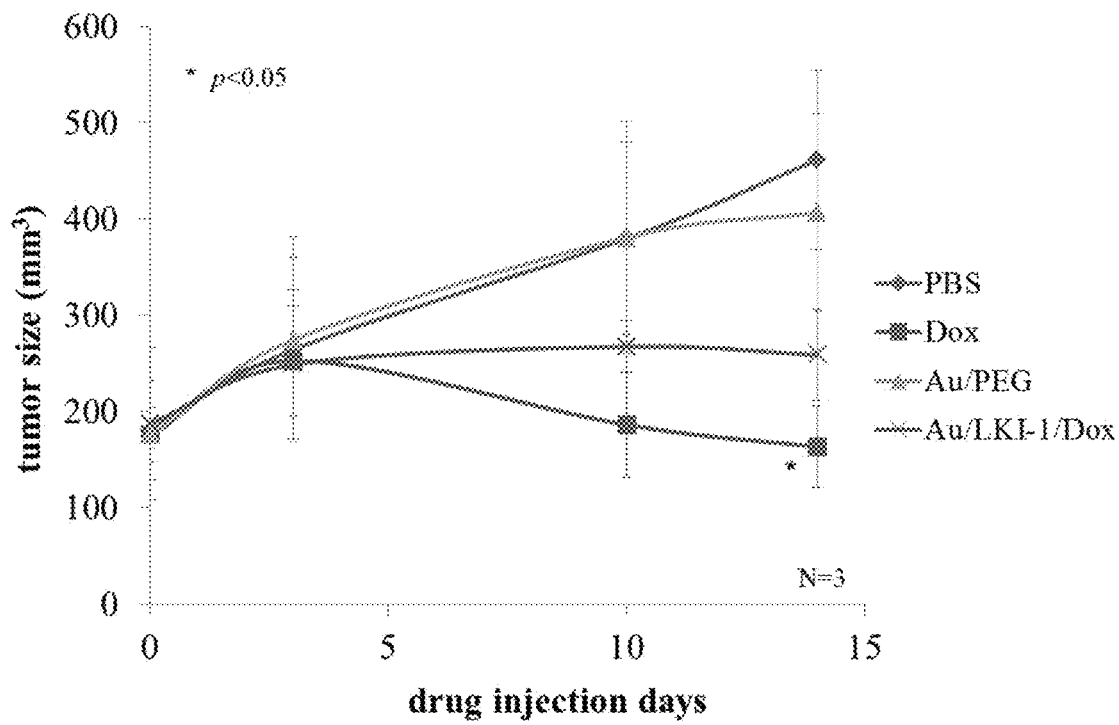
Figure 6C:
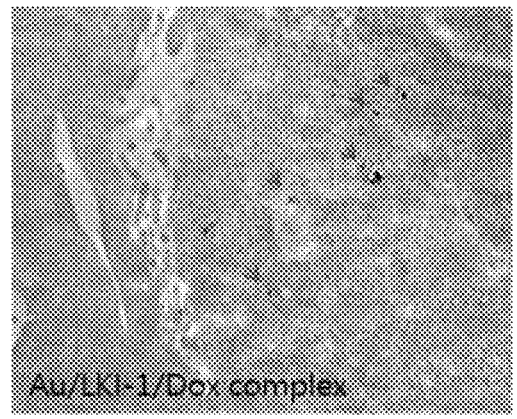
Figure 6D:
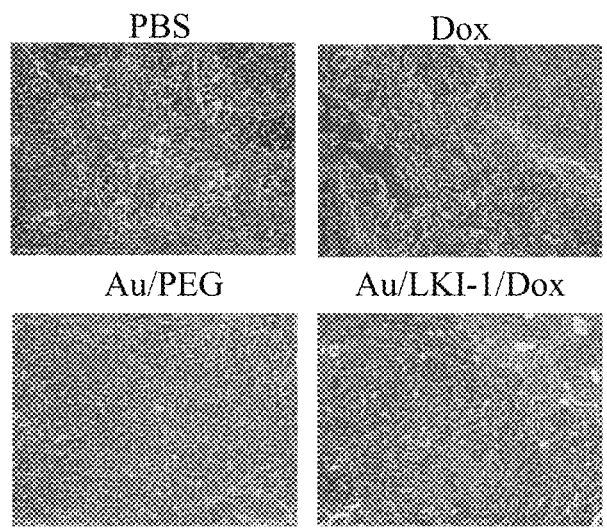

BALB/c-nu/nu mice were purchased from BioLASCO Taiwan. Eight week old male mice were injected unilaterally with 1.0×10⁷ MDA-MB-231 breast tumor cells in 200 μL of 50:50 Matrigel/Leibovitz's (L-15) into the dorsum by subcutaneous injection. (1) Vehicle-PBS (negative control), (2) Doxorubicin (positive control), 5 mg/kg, (3) Au/PEG, (4) Au/LKI-1/Dox complex, 5 mg/kg of Dox. Treatment was ongoing until clinical symptoms necessitated sacrifice. Mice were weighed a minimum of two times/weekly and were monitored tumor size until clinical symptoms necessitated sacrifice (see FIG. 6A, 6B). TEM images of MDA-MB-231 breast tumor cells treated with Au/LKI-1/Dox complex in xenograft model. The arrows in the figure show that the Au/LKI-1/Dox complex exist inside the MDA-MB-231 breast tumor cells. (see FIG. 6C) H&E stain of MDA-MB-231 tumor cells treated with Au/LKI-1/Dox complex in xenograft model. (see FIG. 6D)

We claim:

1. A metallic nanoparticle complex, comprising a metallic nanoparticle complexed with one or more linkers having the following Formula (I),

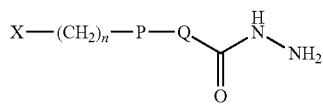

wherein
X is

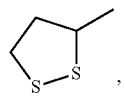

—SH, —NH$_2$, Fmoc-NH—, or —COOH;
n is 1 to 6;
P is —C(O)NH— or —C(O)O—;
Q is —R(CH$_2$CH$_2$O)m-, R(—C(O)NH-)z or —R[—C(O)CH$_2$CH$_2$—C(O)NH—(CH$_2$CH$_2$O)m]Y;
R is a bond, —C$_{1-12}$alkyl or C$_{1-10}$alkoxy;
m is 1 to 12;
z is 1 to 4; and
Y is 1 or 2,
complexed with one or more polyethylene glycol molecules (PEGs).

2. The metallic nanoparticle complex of claim 1, wherein the linker has the following formula:

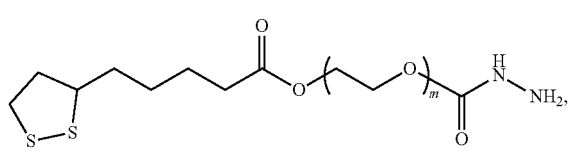

(Linker I-C(O)O; Linker III)

wherein m is 1 to 12.

3. The metallic nanoparticle complex of claim 1, wherein the linker has the following formula:

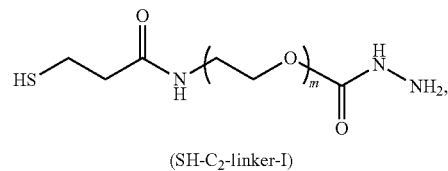

(SH-C$_2$-linker-I)

wherein m is 1 to 12.

4. The metallic nanoparticle complex of claim 1, wherein the linker has the following formula:

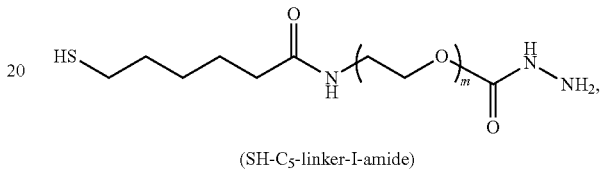

(SH-C$_5$-linker-I-amide)

wherein m is 1 to 12.

5. The metallic nanoparticle complex of claim 1, wherein the linker has the following formula:

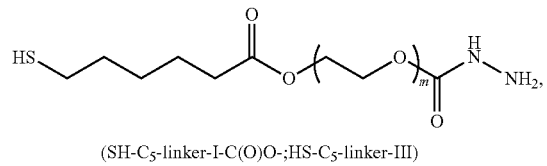

(SH-C$_5$-linker-I-C(O)O-;HS-C$_5$-linker-III)

wherein m is 1 to 12.

6. The metallic nanoparticle complex of claim 1, wherein the linker has the following formula:

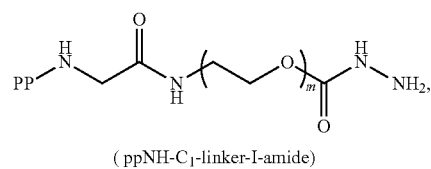

(ppNH-C$_1$-linker-I-amide)

wherein pp is a protection group selected from Boc or Fmoc; and m is 1 to 12.

7. The metallic nanoparticle complex of claim 1, wherein the linker has the following formula:

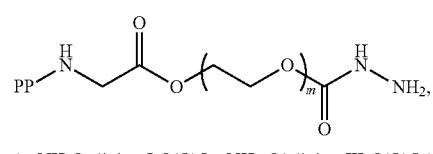

(ppNH-C$_1$-linker-I-C(O)O-; NH$_2$-C1-linker-III-C(O)O-)

wherein pp is a protection group (such as Boc or Fmoc); and m is 1 to 12.

8. The metallic nanoparticle complex of claim 1, wherein the linker has the following formula:

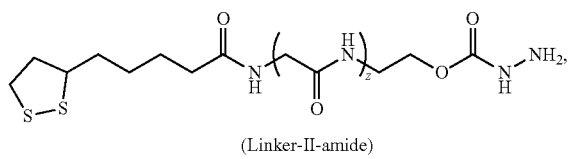
(Linker-II-amide)

wherein z is 1 to 4.

9. The metallic nanoparticle complex of claim 1, wherein the linker has the following formula:

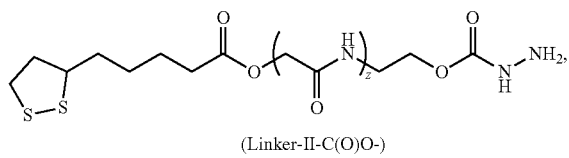
(Linker-II-C(O)O-)

wherein z is 1 to 4.

10. The metallic nanoparticle complex of claim 1, wherein the linker has the following formula:

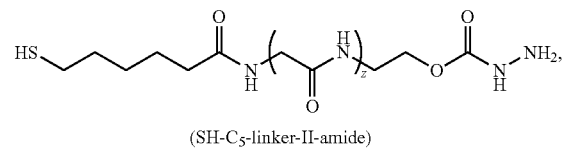
(SH-C$_5$-linker-II-amide)

wherein z is 1 to 4.

11. The metallic nanoparticle complex of claim 1, wherein the linker has the following formula:

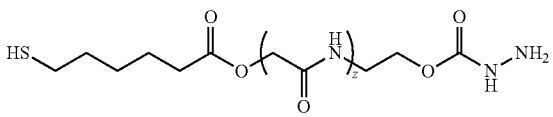

wherein z is 1 to 4.

12. The metallic nanoparticle complex of claim 1, wherein the linker has the following formula:

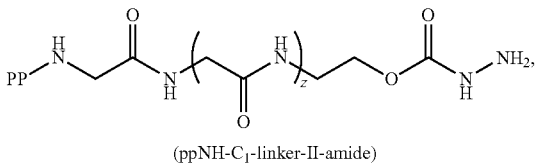
(ppNH-C$_1$-linker-II-amide)

wherein pp is a protection group selected from Boc or Fmoc; and
z is 1 to 4.

13. The metallic nanoparticle complex of claim 1, wherein the linker has the following formula:

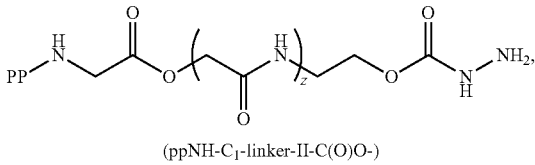
(ppNH-C$_1$-linker-II-C(O)O-)

wherein pp is a protection group selected from Boc or Fmoc; and
z is 1 to 4.

14. The metallic nanoparticle complex of claim 1, wherein the linker has the following formula:

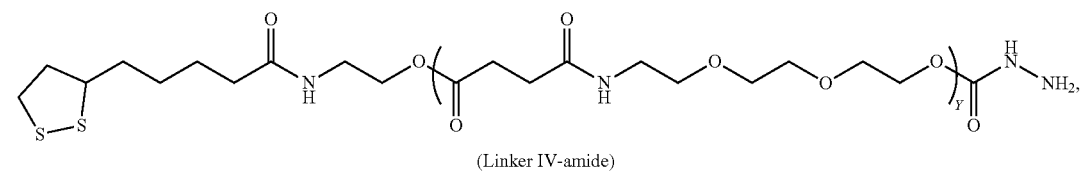
(Linker IV-amide)

wherein Y is 1 or 2.

15. The metallic nanoparticle complex of claim 1, wherein the linker has the following formula:

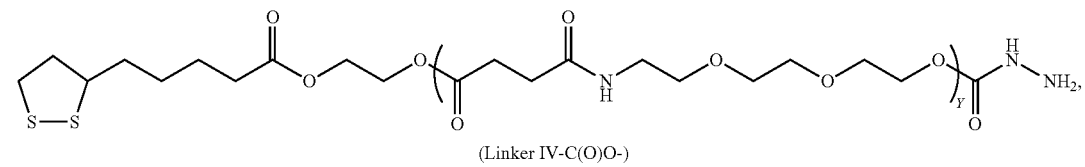
(Linker IV-C(O)O-)

wherein Y is 1 or 2.

16. The metallic nanoparticle complex of claim 1, wherein the linker has the following formula:

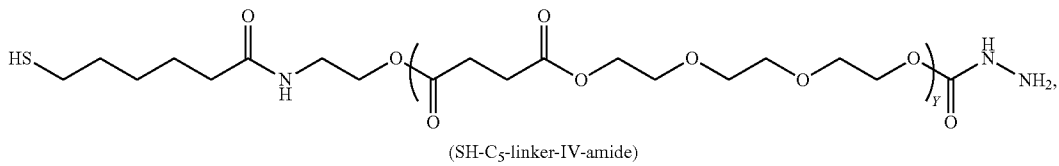

(SH-C$_5$-linker-IV-amide)

wherein Y is 1 or 2.

17. The metallic nanoparticle complex of claim 1, wherein the linker has the following formula:

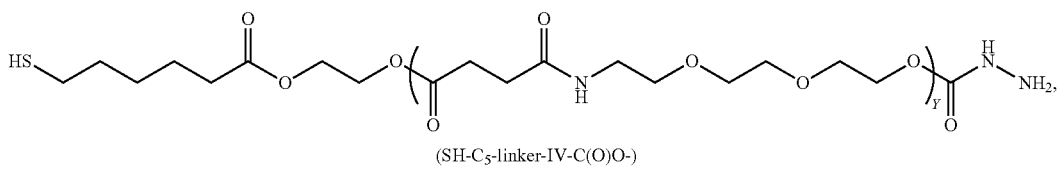

(SH-C$_5$-linker-IV-C(O)O-)

wherein Y is 1 or 2.

18. The metallic nanoparticle complex of claim 1, wherein the linker has the following formula:

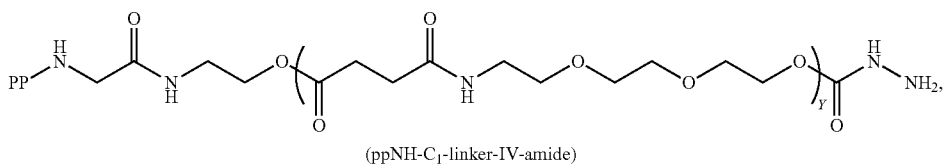

(ppNH-C$_1$-linker-IV-amide)

wherein pp is a protection group selected from Boc or Fmoc; and Y is 1 or 2.

19. The metallic nanoparticle complex of claim 1, wherein the linker has the following formula:

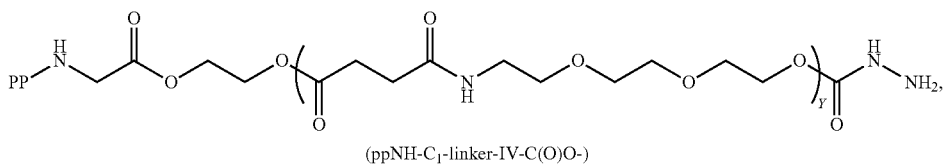

(ppNH-C$_1$-linker-IV-C(O)O-)

wherein pp is a protection group selected from Boc or Fmoc; and Y is 1 or 2.

20. The metallic nanoparticle complex of claim 1, wherein the linker has the following formula:

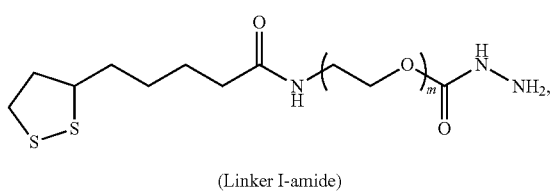

(Linker I-amide)

wherein m is 1 to 12.

21. The metallic nanoparticle complex of claim 1, wherein the metallic nanoparticle is Au nanoparticle, Pd nanoparticle, Pt nanoparticle or Ag nanoparticle.

22. The metallic nanoparticle complex of claim 1, wherein the more linkers are same or different.

23. The metallic nanoparticle complex of claim 1, wherein the metallic nanoparticle complex comprises plural linkers with different molecular length.

24. The metallic nanoparticle complex of claim 1, wherein the molecular weight of PEG used in the invention ranges from about 2000 to 20,000 Da.

25. The metallic nanoparticle complex of claim 1, wherein the metallic nanoparticle is in a size less than about 80 nm.

26. The metallic nanoparticle complex of claim 1, wherein the metallic nanoparticle complex further links one or more same of different therapeutic or diagnostic agents.

27. The metallic nanoparticle complex of claim 26, wherein the therapeutic agent is anti-tumor drug or an antibody; preferably, the antibody is an antibody targeted to a specific cell such as tumor cell or an anti-tumor antibody.

28. The metallic nanoparticle complex of claim 27, wherein the anti-tumor drug is an anti-cancer drug.

29. The metallic nanoparticle complex of claim 28, wherein the anti-cancer drug is an alkylating agent, an alkyl sulfonate, an aziridine, a purine analog, a pyrimidine analog, camptothecin or doxorubicin, cisplatin.

30. The metallic nanoparticle complex of claim 28, wherein the amount of the anticancer accounts for about 1% to about 50% (weight/weight) of the metallic nanoparticle complex.

31. A pharmaceutical composition, comprising one or more metallic nanoparticle complex of claim 1 linking one or more same of different therapeutic or diagnostic agents and a pharmaceutically acceptable carrier.

32. A method of delivering a therapeutic or diagnostic agent to a subject, comprising administering the metallic nanoparticle complex of claim 26 to the subject.

* * * * *